US009611313B2

(12) United States Patent
Shin et al.

(10) Patent No.: US 9,611,313 B2
(45) Date of Patent: Apr. 4, 2017

(54) ANTIBODY-ENDOSTATIN FUSION PROTEIN AND ITS VARIANTS

(71) Applicant: University of Miami, Miami, FL (US)

(72) Inventors: Seung-Uon Shin, Miami, FL (US); Joseph David Rosenblatt, Miami, FL (US); Sherie L. Morrison, Los Angeles, CA (US)

(73) Assignee: UNIVERSITY OF MIAMI, Miami, FL (US)

( * ) Notice: Subject to any disclaimer, the term of this patent is extended or adjusted under 35 U.S.C. 154(b) by 0 days.

(21) Appl. No.: 14/254,333

(22) Filed: Apr. 16, 2014

(65) Prior Publication Data

US 2014/0220016 A1 Aug. 7, 2014

Related U.S. Application Data

(63) Continuation-in-part of application No. 12/665,007, filed as application No. PCT/US2008/068434 on Jun. 26, 2008.

(60) Provisional application No. 60/946,245, filed on Jun. 26, 2007.

(51) Int. Cl.

| | | |
|---|---|---|
| *A61K 39/385* | (2006.01) | |
| *C07K 14/78* | (2006.01) | |
| *A61K 45/06* | (2006.01) | |
| *G01N 33/574* | (2006.01) | |
| *C07K 16/28* | (2006.01) | |
| *C07K 16/32* | (2006.01) | |
| *A61K 31/00* | (2006.01) | |
| *A61K 39/00* | (2006.01) | |
| *A61K 38/00* | (2006.01) | |

(52) U.S. Cl.
CPC .............. *C07K 14/78* (2013.01); *A61K 31/00* (2013.01); *A61K 45/06* (2013.01); *C07K 16/2863* (2013.01); *C07K 16/32* (2013.01); *G01N 33/57492* (2013.01); *A61K 38/00* (2013.01); *A61K 2039/505* (2013.01); *C07K 2319/00* (2013.01); *G01N 2333/71* (2013.01)

(58) Field of Classification Search
None
See application file for complete search history.

(56) References Cited

U.S. PATENT DOCUMENTS

| | | | |
|---|---|---|---|
| 5,547,668 A | 8/1996 | Kranz et al. | |
| 5,863,538 A | 1/1999 | Thorpe et al. | |
| 6,147,060 A * | 11/2000 | Zasloff et al. | 514/110 |
| 6,653,447 B1 | 11/2003 | Cosman et al. | |
| 6,825,167 B1 | 11/2004 | Yokoyama et al. | |
| 2004/0038339 A1 | 2/2004 | Kufer et al. | |
| 2005/0008649 A1 * | 1/2005 | Shin et al. | 424/178.1 |
| 2005/0021710 A1 | 1/2005 | Johnson et al. | |
| 2006/0121032 A1 | 6/2006 | Dahiyat et al. | |

FOREIGN PATENT DOCUMENTS

WO WO-2007/097812 A2 8/2007

OTHER PUBLICATIONS

Folberg et al (American Journal of Pathology, 2000, 156(2): 361-381).*
Shirakawa et al (Int J Cancer, 2002, 99: 821-828).*
Yokoyama et al (Br J Cancer, 2004, 90(8): 1627-1635).*
Yokoyama et al (Int J Cancer, 2004, 111: 839-848).*
Veronesi et al (Oncologist, 1996, 1(6): Abstract).*
Abdollahi et al., Endostatin's Antiangiogenic Signaling Network, *Molecular Cell*, 13:649-63 (2004).
Baselga et al., Phase II Study of Weekly Intravenous Recombinant Humanized Anti-p185HER2 Monoclonal Antibody in Patients With HER2/neu-Overexpressing Metastatic Breast Cancer, *J. Clin. Oncol.*, 14(3):737-44 (1996).
Beck et al., Prolactin Antagonist-endostatin Fusion Protein as a Targeted Dual-Functional Therapeutic Agent for Breast Cancer, *Can. Res.*, 63:3598-604 (2003).
Becker et al., Short synthetic endostatin peptides inhibit endothelial migration in vitro and endometriosis in a mouse model, *Fertility and Sterility*, 85(1):72-7 (2006).
Biburger et al., A novel bispecific tetravalent antibody fusion protein to target costimulatory activity for T-cell activation to tumor cells overexpressing ErbB2/HER2, *J. Mol. Biol.*, 346:1299-311 (2005).
Boehm et al., Antiangiogenic therapy of experimental cancer does not induce acquired drug resistance, *Nature*, 390:404-7 (1997).
Bookman, Evaluation of monoclonal humanized anti-HER2 antibody, Trastuzumab, in patients with recurrent or refractory ovarian or primary peritoneal carcinoma with overexpression of HER2: a phase II trial of the Gynecologic Oncology Group, *J. Clin. Oncol.*, (2003) 21(2): 283-290.
Bowie, Deciphering the message in protein sequences: tolerance to amino acid substitutions, *Science*, 247:1306-10 (1990).
Burgess, Possible dissociation of the heparin-binding and mitogenic activities of heparin-binding (acidic fibroblast) growth factor-1 from its receptor-binding activities by site-directed mutagenesis of a single lysine residue. *J. Cell Biology*. 111:2129-38 (1990).
Burstein et al., Trastuzumab and Vinorelbine as First-Line Therapy for HER2-Overexpressing Metastatic Breast Cancer: Multicenter Phase II Trial With Clinical Outcomes, Analysis of Serum Tumor Markers as Predictive Factors, and Cardiac Surveillance Algorithm, *J. Clin. Oncol.*, 21(15):2889-95 (2003).
Calfa et al., Antibodies and antibody-fusion proteins as anti-angiogenic, anti-tumor agents; *Update on Cancer Therapeutics*, 1(2):159-73 (2006).
Calvo et al., Inhibition of the mammary carcinoma angiogenic switch in C3(1)/SV40 transgenic mice by a mutated form of human endostatin, *Int. J. Cancer*, 101:224-34 (2002).

(Continued)

*Primary Examiner* — Sean Aeder
(74) *Attorney, Agent, or Firm* — Marshall, Gerstein & Borun LLP

(57) ABSTRACT

Methods of inhibiting the growth of tumors comprising administering chimeric fusion molecules comprising endostatin mutants and all or a portion of anti-Her2 or anti-EGFR antibodies.

10 Claims, 22 Drawing Sheets

(56) References Cited

OTHER PUBLICATIONS

Cerwenka et al., Ectopic expression of retinoic acid early inducible-1 gene (RAE-1) permits natural killer cell-mediated rejection of a MHC class-I bearing tumor in vivo, *PNAS*, 20(98):115216 (2001).
CHALLITA-EID, A B7.1-antibody fusion protein retains antibody specificity and ability to activate via the T cell costimulatory pathway, *J. Immunol.*, 160(7):3419-26 (1998).
Chaudhary et al., A recombinant immunotoxin consisting of two antibody variable domains fused to Pseudomonas exotoxin, *Nature*, 339:394-7 (1989).
Cho et al., Enhanced inhibition of murine tumor and human breast tumor xenografts using targeted delivery of an antibody-endostatin fusion protein, *Molec. Can. Ther.*, 4 956-67 (2005).
Diefenbach et al., Ligands for the murine NKG2D receptor: expression by tumor cells and activation of NK cells and macrophages, *Nat. Immunol.*, 1(2):119-26 (2000).
Diefenbach et al., Rae1 and H60 ligands of the NKG2D receptor stimulate tumor immunity, *Nature*, 13:165-71 (2001).
Diefenbach et al., The innate immune response to tumors and its role in the induction of T-cell immunity, *Immunol. Rev.*, 188:9-21 188. (2002).
Eder et al., Phase I Clinical Trial of Recombinant Human Endostatin Administered as a Short Intravenous Infusion Repeated Daily, *J. Clin. Oncol.*, 20(18):3772-84 (2002).
European Communication mailed on Apr. 4, 2013 in EP application No. 08 772 085.0. (8 pages).
Flanagan et al., H6OTTNT-3 Fusion Protein Activates NK Cells in Vitro and Improves Immunotherapy Outcome in Murine Syngeneic Tumor Models, *J. Immunother.*, 29(3):274-83 (2006).
Folberg et al., Vasculogenic Mimicry and Tumor Angiogenesis, *American J. Pathol.* 156(2):361-81 (2000).
Hank et al. Activation of human effector cells by a tumor reactive recombinant anti-ganglioside GD2 interleukin-2 fusion protein; Clinical Cancer Research: *An Official Journal of the American Association for Cancer Research*, 2(12):1951-9 (1996).
Hansma et al., Recombinant human endostatin administered as a 28-day continuous intravenous infusion, followed by daily subcutaneous injections: a phase I and pharmacokinetic study in patients with advanced cancer, *Annals of Oncol.*, 16:1795-1701 (2005).
Herbst et al., Development of Biologic Markers of Response and Assessment of Antiangiogenic Activity in a Clinical Trial of Human Recombinant Endostatin, *J. Clin. Oncol.*, 20(18):3804-14 (2002).
Herbst et al., Phase I Study of Recombinant Human Endostatin in Patients With Advanced Solid Tumors, *J. Clin. Oncol.*, 20(18):3792-803 (2002).
Heuser Claudia et al., Anti-CD30-svFv-Fc-Il-2 antibody-cytokine fusion protein that induces resting NK cells to highly efficient cytolysis of Hodgkin's lymphoma derived tumor cells, *Inter. J. Can.*, 10(3):386-94 (2004).
Heuser et al., Anti-CD30-scFv-Fc-Il-2 antibody-cytokine fusion protein that induces resting NK cells to highly efficient cytolysis of Hodgkin's lymphoma derived tumour cells, *Int. J. Cancer*, 110:386-94 (2004).
Hu et al., Minibody: A novel engineered anti-carcinoembryonic antigen antibody fragment (single-chain Fv-CH3) which exhibits rapid, high-level targeting of xenografts, *Cancer Research*, 56:305561 (1996).
Kesari et al., Phase II study of temozolomide, thalidomide, and celecoxib for newly diagnosed glioblastoma in adults, *Neuro Oncology*, 300-8 (2008).
Kisker et al., Continuous Administration of Endostatin by Intraperitoneally Implanted Osmotic Pump Improves the Efficacy and Potency of Therapy in a Mouse Xenograft Tumor Model, *Cancer Research*, 61:7669-74 (2001).
Kulke et al., Phase II Study of Recombinant Human Endostatin in Patients With Advanced Neuroendocrine Tumors, *J. Clin. Oncol.*, 24(22):3555-61 (2006).

Kuo et al., Oligomerization-dependent Regulation of Motility and Morphogenesis by the Collagen XVIII NC1/Endostatin Domain, *J. Cell Biol.*, 152(6):1233-46 (2001).
Larbouret et al., In vivo therapeutic synergism of anti-epidermal growth factor receptor and anti-HER2 monoclonal antibodies against pancreatic carcinomas, *Clin. Can. Res., Amer. Assoc. Can. Res.*, 13(11):3356-62 (2007).
Lazar, Transforming growth factor alpha: mutation of aspartic acid 47 and leucine 48 results in different biological activities, *Molecular and Cellular Biology*, 8:1247-52 (1988).
Lee et al., Linking Antibody Fc Domain to Endostatin Significantly Improves Endostatin Half-life and Efficacy; *Clin. Can. Res.*, 14(5):1487-93 (2008).
Office Action dated Sep. 16, 2008, in U.S. Appl. No. 11/427,628.
O'Reilly et al., Endostatin: An Endogenous Inhibitor of Angiogenesis and Tumor Growth, *Cell*, 88:277-85 (1997).
Papaldo et al., A phase II study on metastatic breast cancer patients treated with weekly vinorelbine with or without trastuzumab according to HER2 expression: changing the natural history of HER2-positive disease, *Annals of Oncology*, 17:630-6 (2006).
Penichet et al., A recombinant IgG3-(IL-2) fusion protein for the treatment of human HER2/neu expressing tumors, *Human Antibodies*, 10:43-9 (2001).
Perletti et al., Antitumor Activity of Endostatin against Carcinogen-induced Rat Primary Mammary Tumors, *Cancer Research*, 60,1793-1796 (2000).
Piccart-Gebhart et al., Trastuzumab after adjuvant chemotherapy in HER2-positive breast cancer, *N. Engl. J. Med.*, 353(16):1659-72 (2005).
Rudikoff, Trastuzumab after adjuvant chemotherapy in HER2-positive breast cancer, *Proc. Natl. Acad. Sci. USA*,79:1979 (1982).
Sanchez et al., Enhanced antiangiogenic therapy with antibody-collagen XVIII NC1 domain fusion proteins engineered to exploit matrix remodeling events, *Int. J. Cancer*, 119:455-62 (2006).
Scheffold et al. Visualization of Effective Tumor Targeting by CD8+Natural Killer T cells redirected with Bispecific Antibody F(ab')2 Her2XCD3, *Cancer Research*, 62:5785-91 (2002).
Scholl et al., Targeting HER2 in other tumor types, *Annals of Oncol.*, 12(1):S81-7 (2001).
Segal et al., Bispecific antibodies in cancer therapy, *Curr. Opin. Immunol.*, 11(5):558-62 (1999).
Seiden et al., A phase II trial of EMD72000 (matuzumab), a humanized anti-EGFR monoclonal antibody, in patients with platinum-resistant ovarian and primary peritoneal malignancies, *Gynecologic Oncology*, 104:727-31 (2007).
Shin et al., Targeted Delivery of an Antibody-Mutant Human Endostatin Fusion Protein Results in Enhanced Antitumor Efficacy, *Molecular Cancer Therapy*, 10(4):603-14 (2011).
Shin et al., Transferrin-antibody fusion proteins are effective in brain targeting, *Proc. Natl. Acad. Sci.*, 95:2820-4(1995).
Shin, Breast Cancer Therapy Using Antibody-Endostatin Fusion Proteins, Apr. 1, 2007; pp. 1-15; url: http://www.dtic.mil/dtic/tr/fulltext/u2/a470864.pdf (retrieved Apr. 11, 2011).
Shin, Breast Cancer Therapy Using Antibody-Endostatin Fusion Proteins; Apr. 1, 2006; pp. 1- 12; url: http://www.dtic.mil/dtic/tr/fulltext/u2/a455083.pdf (retrieved Apr. 11, 2011).
Shirakawa et al., Vasculogenic Mimicry and Pseudo-comedo Formation in Breast Cancer, *Internat. J. Can.*, 99(3):821-8 (2002).
Supplementary Search Report dated Dec. 2, 2009, in European Application EP 2006 774378.
Supplementary Search Report dated Nov. 4, 2011, in European Application EP 2008 772085.
Sutherland et al., UL16-Binding Proteins, Novel MHC Class I-Related Proteins, Bind to NKG2D and Activate Multiple Signaling Pathways in Primary NK Cells, *J. Immunol.*, 168:671-9 (2002).
Thomas et al., Phase I Pharmacokinetic and Pharmacodynamic Study of Recombinant Human Endostatin in Patients With Advanced Solid Tumors, *J. Clin. Oncol.*, 21(2):223-31 (2003).
Tjin Tham Sjin et al., A 27-Amino-Acid Synthetic Peptide Corresponding to the NH2-Terminal Zinc-Binding Domain of Endostatin Is Responsible for Its Antitumor Activity, *Cancer Research*, 65(9):3657-63 (2005).

(56) References Cited

OTHER PUBLICATIONS

Tjin Tham Sjin et al., Endostatin therapy reveals a U-shaped curve for antitumor activity, *Cancer Gene Ther.*, 13:619-27 (2006).
Tomblyn et al. Combination therapy using three novel prolactin receptor antagonist-based fusion proteins effectively inhibits tumor recurrence and metastasis in HER2/neu transgenic mice, *Internat. J. Oncol.*, 34:1139-46 (2009).
Veronesi et al., Optimal Surgical Treatment of Breast Cancer, *Oncol.*, 1(6):340-6 (1996).
Vogel et al., Efficacy and Safety of Trastuzumab as a Single Agent in First-Line Treatment of HER2-Overexpressing Metastatic Breast Cancer, *J. Clin. Oncol.*, 20(3):719-26 (2002).
Xie et al. A trivalent anti-erbB2/anti-CD16 bispecific antibody retargeting NK cells against human breast cancer cells, *Biochemical and Biophysical Research Communications*, 311(2):307-12 (2003).
Yokoyama et al., Addition of integrin binding sequence to a mutant human endostatin improves inhibition of tumor growth, *Internat. J. Can.*, 111(6):839-48 (2004).
Yokoyama et al., Improved biological activity of a mutant endostatin containing a single amino-acid substitution, *Brit. J. Can.*, 90:1627-35 (2004).
International Search Report dated Nov. 2, 2006, in PCT Application PCT/US06/25658.
Written Opinion dated Nov. 2, 2006, in PCT Application PCT/US06/25658.
Lee et al., Inhibition of breast cancer growth and metastasis by a biomimetic peptide, *Sci. Rep.* 4:7139 (2014).
Li et al., Prostate-Restricted Replicative Adenovirus Expressing Human Endostatin-Angiostatin Fusion Gene Exhibiting Dramatic Antitumor Efficacy, *Can. Ther: Preclin.*, 14(1):291 (2008).
Ling et al., Endostar, a novel recombinant human endostatin, exerts antiangiogenic effect via blocking VEGF-induced tyrosine phosphorylation of KDR/Flk-1 of endothelial cells, *Biochem. Biophys. Res.*, 361:79-84 (2007).
Ragg, Studies on the Structure-Activity Relationship of Endostatin: Synthesis of Human Endostatin Peptides Exhibiting Potent Anti8angiogenic Activities, *J. Med. Chem.*, 46:4165-72 (2003).
Wood et al., PTK787/ZK 222584, a Novel and Potent Inhibitor of Vascular Endothelial Growth.Factor Receptor Tyrosine Kinases, Impairs Vascular Endothelial Growth Factor-induced Responses and Tumor Growth after Oral Administration, *Can. Res.*, 60:2178-89 (2000).

* cited by examiner

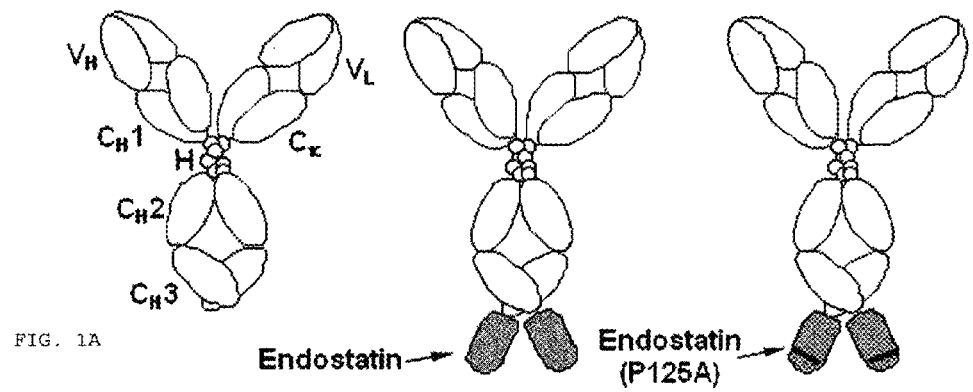
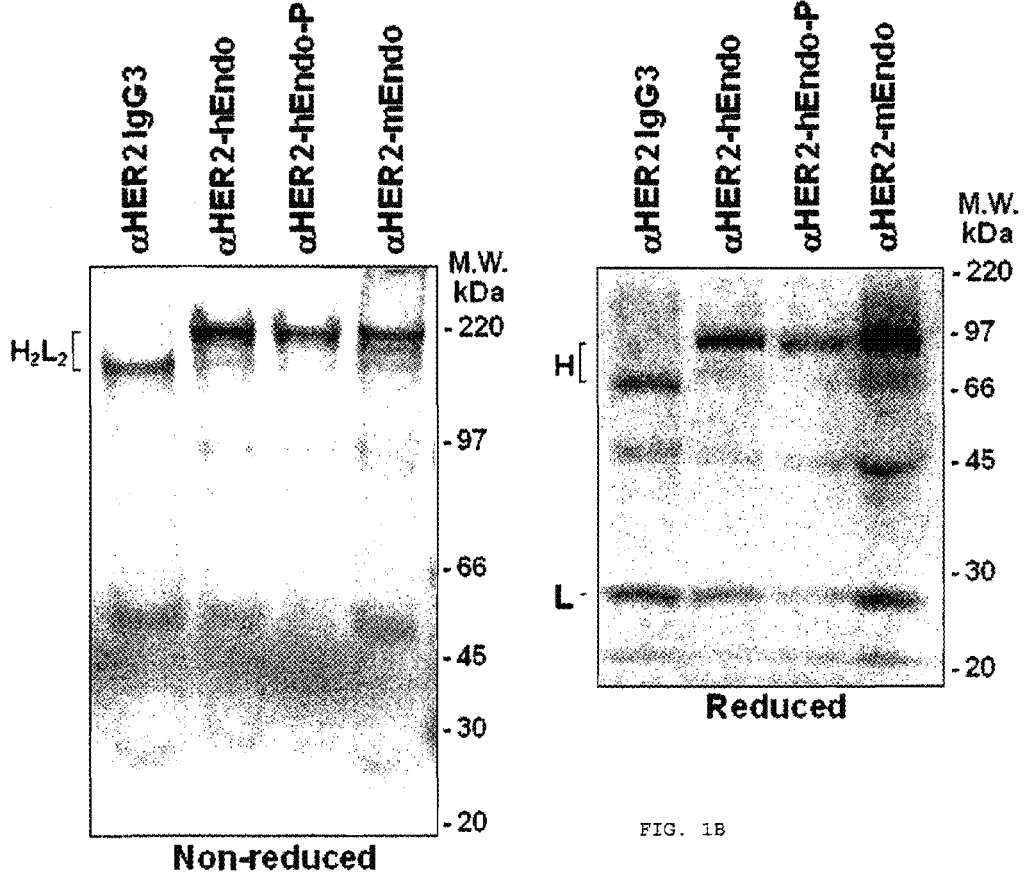
FIG. 1A
FIG. 1B

SEQUENCE LISTING

```
<160> NUMBER OF SEQ ID NOS: 7

<210> SEQ ID NO 1
<211> LENGTH: 37
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 1
cccctcgcga tatcacagcc accgcgactt ccagccg                              37

<210> SEQ ID NO 2
<211> LENGTH: 37
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 2
ccccgaattc gttaaccctt ggaggcagtc atgaagc                              37

<210> SEQ ID NO 3
<211> LENGTH: 18
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 3
atggcagaag ggcagcat                                                   18

<210> SEQ ID NO 4
<211> LENGTH: 24
<212> TYPE: DNA
<213> ORGANISM: ARTIFICIAL SEQUENCE
<220> FEATURE:
<223> OTHER INFORMATION: SYNTHETIC CONSTRUCT
```

```
<400> SEQUENCE: 4
ttggtgaggt ttgatccgca tcat                                          24

<210> SEQ ID NO 5
<211> LENGTH: 21
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 5
ccatgaactt tctgctgtct t                                             21

<210> SEQ ID NO 6
<211> LENGTH: 21
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 6
tcgatcgttc tgtatcagtc t                                             21

<210> SEQ ID NO 7
<211> LENGTH: 21
<212> TYPE: DNA
<213> ORGANISM: ARTIFICIAL SEQUENCE
<220> FEATURE:
<223> OTHER INFORMATION: SYNTHETIC CONSTRUCT

<400> SEQUENCE: 7
ggctcggacg ccaacgggcg c                                             21
```

ANTIBODY-ENDOSTATIN FUSION PROTEIN AND ITS VARIANTS

CROSS-REFERENCE TO RELATED APPLICATIONS

This application is a continuation-in-part of co-pending U.S. patent application Ser. No. 12/665,007, filed on Dec. 16, 2009, as a U.S. National Stage under 35 U.S.C. 371 application of international application no. PCT/US08/68434, filed on Jun. 26, 2008, which claims the benefit of U.S. provisional application No. 60/946,245, filed Jun. 26, 2007, the disclosures of which are all herein incorporated by reference in their entireties.

FIELD OF THE INVENTION

This invention relates to compositions and methods for targeting and modulating the activity of tumor cells. In particular, the invention relates to chimeric fusion molecules which have a tumor antigen targeting domain and an anti-tumor effector function domain.

BACKGROUND

Anti-angiogenic tumor therapies have recently attracted intense interest because of their broad-spectrum action, low toxicity, and absence of drug resistance. Endostatin is a recently characterized anti-angiogenic agent. Although the mechanism of action of endostatin is not clear yet, the anti-tumor activity of endostatin may be associated with inhibiting the proliferation and migration of endothelial cells. In addition, endostatin may down-regulate VEGF expression in tumor cells.

A number of animal experiments and human clinical trials have been performed to assess the anti-tumor effect of endostatin. Systemic administration of endostatin at 10 mg/kg suppressed the growth of human renal cell cancer in a nude mouse xenograft model. In early human phase I trials, endostatin administration at high dose levels (240 mg/m$^2$/day) in the range of active levels established in tumor xenograft studies did not show any significant detectable changes in biologic endpoints, such as urinary excretion levels of VEGF and basic FGF. However, modest clinical benefit was observed in three out of 15 patients. One patient with a pancreatic neuroendocrine tumor had a minor tumor reduction, and disease in two other patients briefly stabilized. Another human phase I trial demonstrated that endostatin was well tolerated and did not induce dose-limiting toxicity at dose-levels up to 600 mg/m$^2$/day, but little anti-tumor activity was seen in 25 patients, even at circulating levels beyond those previously noted to be effective in mouse models. Two patients (one with sarcoma, one with melanoma) demonstrated minor and short-lived anti-tumor activity. The first two phase I clinical trials proved that endostatin is a very safe drug in a variety of dose schedules. However these results did not demonstrate substantial endostatin anti-tumor activity. The dose and schedules may have been suboptimal, and/or bulky disease in late stage patients may not be optimally responsive to recombinant human endostatin.

Anti-angiogenic gene therapy has been proposed as an alternative way to continuously provide high concentrations of the anti-angiogenic factors. Gene transfection of anti-angiogenic agents using a viral vector can inhibit the growth of tumor in several mouse models. Viral vectors, however, may cause inflammation and immunological response on repeated injection, and toxicity/safety considerations may preclude their use in humans in the near future. Furthermore, use of gene-transduced hematopoietic stem cells has been ineffective in an animal model, despite sustained production of endostatin. Furthermore dosing of biologic products using gene vectors is very difficult to standardize due to variation in vector titer, transduction efficiency and expression levels. There is, thus, a need in the art for improved anti-tumor therapies.

SUMMARY

The invention provides methods and compositions for targeting a chimeric molecule containing both (1) anti-angiogenic agent and (2) a carrier domain such as all or a portion of an Ig molecule to a tumor.

The advantages of the chimeric fusion molecules provide many therapeutic advantages. For example, an increase in the half-life of the endostatin molecule, ease of administration, presentation of endostatin as a dimer, versatile targeting, increased activity against lower her2 expressing tumors and duration/response rate against 3+ tumors, increase in efficacy of endostatin and Herceptin alike, treatment of tumors which have become resistant to traditional treatments, e.g. Herceptin, Trastuzumab and any chemotherapeutic agents. The therapeutic effector domain, e.g. anti-angiogenic domain can be fused to provide alternate specificities, e.g. anti-CD20, MUC-1, EDB and EGFR.

In a preferred embodiment, a method of treating, including therapeutic treatment and prophylactic or preventative measures, a tumor in an animal subject, comprises the step of administering to the animal subject a chimeric molecule fusion composition, comprising an anti-HER2 antigen binding domain and an endostatin protein, peptide, mutants, variants or fragments thereof in a therapeutically effective dose. Preferably, the antigen binding domain comprises an isolated antibody, fragments thereof, or aptamers. In one embodiment, a vector encoding the chimeric fusion protein is administered to a patient.

In another preferred embodiment, the endostatin molecule in the chimeric fusion molecule for treating a patient with a tumor or cancer, comprises one or more mutations at amino acid positions 6-49, 50-92, 93-133 and 134-178 and/or integrin or integrin type motifs, e.g. NGR, RGD and the like.

In another preferred embodiment, the chimeric fusion molecule for treating cancer in a patient comprises endostatin having one or more mutations at amino acid positions 93-133.

In another preferred embodiment, the chimeric fusion molecule for treating cancer in a patient comprises a mutant endostatin having an amino acid substitution at position 125 of human endostatin.

In a preferred embodiment, the substitution comprises any natural or non-natural, analog or variant amino acid.

In another preferred embodiment, the substitution at position 125 is a proline to alanine (P125A).

In yet another preferred embodiment, the chimeric fusion molecule for treating cancer in a patient comprises an antigen binding domain comprising an isolated antibody, fragments thereof or aptamers wherein the antigen binding domain specifically binds one or more tumor antigens.

In a preferred embodiment, the tumor antigen comprises HER2, phosphatase and tensin homolog (PTEN), phosphatidylinositol (PI) kinase, variants, alleles and homologs thereof.

In another preferred embodiment, the chimeric fusion molecule for treating cancer in a patient comprises an endostatin molecule and mutants thereof comprising one or more NGR motifs (Asn-Gly-Arg) and/or RGD (Arg-Gly-Asp) motifs. The endostatin mutant molecules in addition to these integrin or integrin type motifs comprises one or more mutations at amino acid position 125 of the endostatin molecule, at one or more mutations at amino acid positions 6-49, 50-92, 93-133 and 134-178.

In another preferred embodiment, the one or more NGR motifs (Asn-Gly-Arg) and RGD (Arg-Gly-Asp) motifs are located at the amino (NH2-) terminal, and/or carboxy terminal (COOH—) and/or amino acid positions 93-133.

In another preferred embodiment, the one or more NGR motifs (Asn-Gly-Arg) and RGD (Arg-Gly-Asp) motifs are located at amino acid positions 126-128 following the proline or alanine at position 125.

In another preferred embodiment, the chimeric fusion molecule for treating cancer in a patient comprises an antigen specific domain comprising an antibody or fragments thereof, wherein the antibody or fragments thereof comprise IgA, IgM, IgG, IgE, or IgD.

In another preferred embodiment, the chimeric fusion protein is administered to a patient, simultaneously and/or in separate treatments with one or more of: cytoximab, sunitinib, sorafenib, celebrex, MTOR inhibitors, AKT inhibitors, P13K inhibitors, bevacizumab (Avastin), signal transduction inhibitors, tamoxifen, toremifen, raloxifene, droloxifene, iodoxyfene, megestrol acetate, anastrozole, letrazole, borazole, exemestane, flutamide, nilutamide, bicalutamide, cyproterone acetate, goserelin acetate, luprolide, finasteride, herceptin, methotrexate, 5-fluorouracil, cytosine arabinoside, doxorubicin, daunomycin, epirubicin, idarubicin, mitomycin-C, dactinomycin, mithramycin, cisplatin, carboplatin, melphalan, chlorambucil, busulphan, cyclophosphamide, ifosfamide, nitrosoureas, thiotephan, vincristine, taxol, taxotere, etoposide, teniposide, amsacrine, irinotecan, topotecan, an epothilone; a tyrosine kinase inhibitor, Iressa or OSI-774; an angiogenesis inhibitor; an EGF inhibitor; a VEGF inhibitor; a CDK inhibitor; a Her1/2 inhibitor and monoclonal antibodies directed against growth factor receptors.

In another preferred embodiment, a method of treating a patient either prophylactically and/or therapeutically comprises administering the chimeric fusion protein in combination with and/or in separate treatments, one or more antibodies comprising cytoximab, sunitinib, sorafenib, celebrex, MTOR inhibitors, AKT inhibitors, P13K inhibitors, bevacizumab (Avastin), signal transduction inhibitors, and anti her2 antibodies, one or more anti-angiogenic factors comprising sunitinib, sorafenib, and angiostatin.

In preferred embodiments, the therapeutically effective doses are administered under a metronomic regimen.

In a preferred embodiment, a pharmaceutical composition comprises a chimeric fusion molecule, wherein the chimeric fusion molecule comprises an anti-tumor antigen binding domain and at least one human endostatin protein, peptide, mutants, variants or fragments thereof. The specificity of the fusion molecule can be directed to any desired antigen by a fusion peptide comprising an antigen binding domain specific for a desired antigen.

In another preferred embodiment, the chimeric fusion molecule comprises one or more mutations at amino acid positions 6-49, 50-92, 93-133 and 134-178 of the endostatin molecule and include integrin or integrin-like motifs, e.g. NGR, RGD and the like.

In another preferred embodiment, the chimeric fusion molecule comprises endostatin having one or more mutations at amino acid positions 93-133.

In another preferred embodiment, the endostatin is a mutant endostatin at amino acid position 125. The mutant can be a substitution, deletion, variant and the like. In one aspect the mutant endostatin comprises an amino acid substitution at position 125 of human endostatin.

In another preferred embodiment, the substitution at position 125 is a proline to alanine (P125A).

In another preferred embodiment, the endostatin is multimeric.

In another preferred embodiment, the multimers comprise one or more endostatin molecules, one or more mutant endostatin molecules and/or combinations thereof.

In another preferred embodiment, the antigen binding domain comprises an isolated antibody or fragments thereof, or aptamers.

In yet another embodiment, the antigen binding domain binds to HER2/neu tumor antigens, tumor antigens, receptor/ligand complex; or receptors. Preferably, the receptor is a receptor involved in angiogenesis.

In another preferred embodiment, the antigen binding domain specifically binds to antigens comprising HER2/neu tumor antigens, phosphatase and tensin homolog (PTEN), phosphatidylinositol (PI) kinase, receptor/ligand complex; or receptors.

In another preferred embodiment, the receptor, and ligands thereof, is a receptor involved in angiogenesis and modulates angiogenesis such as for example, receptor tyrosine kinases (RTKs), vascular endothelial growth factor (VEGF) and its angiogenic receptor (KDR); ang-1/2; thrombospondin-1 (TSP1) protein and its receptor, integrins $\alpha_v\beta_3$, $\alpha_v\beta_5$ and $\alpha_5\beta_1$.

In another preferred embodiment, the chimeric fusion molecule modulates embryogenesis, neovascularization and tumorigenesis.

In another preferred embodiment, the receptor, and ligands thereof comprises a protein-tyrosine kinase receptor. For example, the Eph receptor family. This family is the largest family of receptor tyrosine kinases identified to date. The Eph receptors and their membrane-anchored ligands, ephrins, mediate bi-directional signaling.

In yet another embodiment, the receptor involved in cellular hyperproliferation comprises Granulocyte Colony-stimulating Factor receptor (G-CSF-R), epidermal growth factor receptor (EGF-R), vascular endothelial growth factor receptor (VEGF-R), brain derived growth factor receptor, transforming growth factor receptor (TGF-R), fibroblast growth factor receptor (bFGF-R), platelet-derived growth factor receptor (PDGF-R), nerve growth factor receptor (NGF-F), colony stimulating factor 1 receptor (CSF1-R), insulin-like growth factor 1 receptor (IGF1-R) and erythropoietin receptor (EPO-R), and the like, regulators, and ligands thereof.

In another preferred embodiment, the receptor comprises a signal transduction receptor including transmembrane, intracellular and cell surface receptors. For example, G-protein coupled receptors, e.g., chemokine receptors; receptor tyrosine kinases, e.g., growth factor receptors; integrins; Toll-like receptors and the like.

In another preferred embodiment, the chimeric fusion molecule comprises an antigen specific binding domain wherein the domain comprises an antibody or fragments thereof, comprising IgA, IgM, IgG, IgE, or IgD.

In another preferred embodiment, the antibody or fragment thereof is IgG1, IgG2, IgG3, and IgG4.

In another preferred embodiment, the antibody domain or fragment thereof is any single chain, two-chain, diabody, minibody, bispecific, multi-chain proteins and glycoproteins of polyclonal, monoclonal, chimeric, and hetero immunoglobulins.

In another preferred embodiment, the antibody or fragment is human or humanized antibody.

In another preferred embodiment, the isolated antibody or immunoglobulin variable region comprise one or more of: Fab, Fab', F(ab')$_2$, and Fv fragments.

In another preferred embodiment, the endostatin protein, P125A endostatin protein, peptides, mutants, alleles, variants or fragments thereof are fused to 3' end of an anti-HER2 antigen binding domain.

In another preferred embodiment, a nucleic acid encoding the chimeric molecule comprises an antigen specific binding domain and a therapeutically effective domain.

In one preferred embodiment, the antigen binding domain specifically binds tumor antigens comprising Her2, Her3, VEGF receptors, PI Kinase receptors, PTEN, EGF receptors, Muc-1, PSMA, CD20, Cd21, CD22, CD23, TAA, wt-1, Eph, alleles, mutants and variants thereof.

In another preferred embodiment, the nucleic acid encodes a therapeutically effective domain comprising endostatin, P125 endostatin, mutants, variants, fragments and alleles thereof.

In another preferred embodiment, chimeric fusion protein comprises an anti-tumor antigen binding domain and an endostatin protein, peptide, mutants, variants or fragments thereof or a plurality of the endostatin molecules.

In another preferred embodiment, the antigen binding domain binds to HER2/neu tumor antigens, tumor specific antigens, receptor/ligand complex; or receptors.

In another preferred embodiment, the chimeric fusion protein comprises a mutant endostatin having an amino acid substitution at positions 6-49, 50-92, 93-133 and 134-178 of the endostatin molecule. The amino acids comprise any natural, non-natural, variant, analog, substituted molecule. The molecule further comprises one or more substitutions comprising integrins or integrin like motifs comprising NGR, RGD and the like.

In another preferred embodiment, the chimeric fusion protein comprises a mutant endostatin having an amino acid substitution at position 125 of human endostatin.

In another preferred embodiment, the substitution at position 125 is a proline to alanine (P125A).

In another preferred embodiment, the endostatin is multimeric.

In another preferred embodiment, the multimers comprise one or more endostatin molecules, one or more mutant endostatin molecules and/or combinations thereof.

In another preferred embodiment, a chimeric fusion protein comprises an anti-tumor antigen binding domain and an endostatin protein, peptide, mutants, variants or fragments thereof or a plurality of the endostatin molecules.

In another preferred embodiment, the chimeric fusion protein comprises an antigen specific binding domain having specificity for: a receptor involved in angiogenesis, a protein-tyrosine kinase receptor, a receptor involved in hyperproliferation, a signal transduction receptor, alleles, mutants, fragments and variants thereof.

In another preferred embodiment, the antigen binding domain comprises an isolated antibody, fragments thereof, or aptamers, wherein the antibody or fragments thereof, is IgA, IgM, IgG, IgE, or IgD. In one aspect, the antibody or fragment thereof is IgG1, IgG2, IgG3, and IgG4.

In another preferred embodiment, the antibody or fragment is human or humanized antibody.

In another preferred embodiment, a method of treating a patient with a tumor expressing low to undetectable levels of Her2, comprises administering to a patient a therapeutically effective amount of a chimeric fusion molecule comprising an anti-HER2 specific binding domain and an endostatin molecule having an alanine substituted for proline at position 125.

In another preferred embodiment, a method of targeting endostatin to a tumor cell in an animal subject, the method comprising the step of administering to the animal subject a composition comprising a chimeric molecule comprising an endostatin domain and an antigen specific domain.

In another preferred embodiment a kit comprises a chimeric fusion molecule comprising an anti-HER2 antigen binding domain and an endostatin protein, peptide, mutants, variants or fragments thereof.

In another preferred embodiment, an isolated cell comprises a polynucleotide acid encoding a chimeric molecule comprising an antigen specific binding domain and a therapeutically effective domain.

In another preferred embodiment, the polynucleotide encodes an antigen binding domain wherein the antigen binding domain specifically binds tumor antigens comprising Her2, Her3, VEGF receptors, PI Kinase receptors, PTEN, EGF receptors, Muc-1, PSMA, CD20, Cd21, CD22, CD23, TAA, wt-1, Eph, alleles, mutants and variants thereof.

In another preferred embodiment, the polynucleotide encodes a therapeutically effective domain, wherein the therapeutically effective domain comprises endostatin, P125A endostatin, mutants, variants, fragments and alleles thereof.

In another preferred embodiment, the polynucleotide encodes multimers of endostatin. In some embodiments the multimers are dimers and/or trimers.

In another preferred embodiment, the multimers comprise one or more endostatin molecules, one or more mutant endostatin molecules and/or combinations thereof.

In another preferred embodiment, an isolated cell comprises a vector or polynucleotide encoding a chimeric molecule comprising an anti-tumor antigen binding domain and an endostatin protein, peptide, mutants, variants or fragments thereof or a plurality of the endostatin molecules.

In another preferred embodiment, the isolated cell comprising a vector or polynucleotide encoding a chimeric molecule, wherein the antigen binding domain binds to HER2/neu tumor antigens, tumor specific antigens, receptor/ligand complex; or receptors.

In another preferred embodiment, the isolated cell comprising a vector or polynucleotide encoding a chimeric molecule, wherein the mutant endostatin comprises an amino acid substitution at position 125 of human endostatin. In one aspect, the substitution at position 125 is a proline to alanine (P125A). In another aspect of the invention, the endostatin molecule comprises amino acid substitutions comprising any natural, non-natural, variant, analog, substituted molecule. The molecule further comprises one or more substitutions comprising integrins or integrin like motifs comprising NGR, RGD and the like.

In another preferred embodiment, the isolated cell comprising a vector or polynucleotide encoding a chimeric molecule, wherein the polynucleotide encodes multimers of endostatin. In some embodiments the multimers are dimers and/or trimers.

In another preferred embodiment, the multimers comprise one or more endostatin molecules, one or more mutant endostatin molecules and/or combinations thereof.

In another preferred embodiment, the isolated cell comprising a vector or polynucleotide encoding a chimeric molecule, wherein the antigen binding domain binds to a receptor comprising a receptor involved in angiogenesis, a protein-tyrosine kinase receptor, a receptor involved in hyperproliferation, a signal transduction receptor, alleles, mutants, fragments and variants thereof. The antigen binding domain comprises an isolated antibody, fragments thereof, aptamers or integrins.

In one aspect the antibody or fragment thereof, is IgA, IgM, IgG, IgE, or IgD.

In another aspect, the antibody or fragments thereof comprise IgG1, IgG2, IgG3, and IgG4.

In another preferred embodiment, the antibody or fragment is human or humanized antibody.

In one embodiment, the receptor is a protein-tyrosine kinase receptor.

In another preferred embodiment, the receptor is a receptor involved in hyperproliferation.

In another preferred embodiment, the antibody or fragment thereof, comprises IgA, IgM, IgG, IgE, or IgD. Preferably, the antibody or fragment thereof is IgG1, IgG2, IgG3, and IgG4.

In another preferred embodiment, the antibody or fragment thereof is any single chain, two-chain, diabody, minibody, bispecific, multi-chain proteins and glycoproteins of polyclonal, monoclonal, chimeric, and hetero immunoglobulins.

In another preferred embodiment, the antibody or fragment is human or humanized antibody.

In another preferred embodiment, the isolated immunoglobulin variable region comprise Fab, Fab', F(ab')$_2$, and Fv fragments.

In another preferred embodiment, the endostatin protein, peptide or fragments thereof are fused to 3' end of an anti-HER2 antigen binding domain.

In another preferred embodiment, the antigen binding domain binds to HER2/neu tumor antigens, tumor antigens, receptor/ligand complex; or receptors.

In another preferred embodiment, a method of targeting endostatin to a tumor cell in an animal subject, the method comprising the step of administering to the animal subject a composition comprising a chimeric molecule comprising an endostatin domain and an Ig domain.

In another preferred embodiment, a method of treating a tumor in an animal subject, the method comprising the step of administering to the animal subject a chimeric molecule fusion composition, comprising an anti-HER2 antigen binding domain and an endostatin protein, peptide, mutants, variants or fragments thereof; and, administration of the composition ameliorates the tumor in the animal subject.

In another preferred embodiment, the chimeric fusion protein is administered to a patient, simultaneously and/or in separate treatments with one or more of: tamoxifen, toremifen, raloxifene, droloxifene, iodoxyfene, megestrol acetate, anastrozole, letrazole, borazole, exemestane, flutamide, nilutamide, bicalutamide, cyproterone acetate, goserelin acetate, luprolide, finasteride, herceptin, methotrexate, 5-fluorouracil, cytosine arabinoside, doxorubicin, daunomycin, epirubicin, idarubicin, mitomycin-C, dactinomycin, mithramycin, cisplatin, carboplatin, melphalan, chlorambucil, busulphan, cyclophosphamide, ifosfamide, nitrosoureas, thiotephan, vincristine, taxol, taxotere, etoposide, tenipo-side, amsacrine, irinotecan, topotecan, an epothilone; a tyrosine kinase inhibitor, Iressa or OSI-774; an angiogenesis inhibitor; an EGF inhibitor; a VEGF inhibitor; a CDK inhibitor; a Her1/2 inhibitor and monoclonal antibodies directed against growth factor receptors.

In another preferred embodiment, the chimeric fusion protein is administered in combination with and/or in separate treatments one or more antibodies comprising cetuximab, bevacizumab (Avastin), and anti her2 antibodies.

In another preferred embodiment, the chimeric fusion protein is administered in combination with and/or in separate treatments one or more anti-angiogenic factors comprising sunitinib, sorafenib, and angiostatin.

In another preferred embodiment, a kit comprises a chimeric fusion molecule comprising an anti-HER2 antigen binding domain and an endostatin protein, peptide, mutants, variants or fragments thereof.

In one embodiment, this disclosure provides a method for inhibiting the formation and/or growth of blood vessels in a tumor. The method comprises administering to an individual who has a tumor an effective amount of a chimeric molecule fusion composition, comprising an anti-HER2 antigen binding domain and an endostatin protein or fragments thereof, or an anti-EGFR antigen binding domain and an endostatin protein or fragments thereof. In one embodiment, the endostatin protein or fragments have a proline to alanine substitution at the 125 position of human endostatin.

In one embodiment, this disclosure provides a method for inhibiting vasculogenic mimicry in a tumor. The method comprises administering to an individual who has a tumor an effective amount of a chimeric molecule fusion composition, comprising an anti-HER2 antigen binding domain and an endostatin protein or fragments thereof, or an anti-EGFR antigen binding domain and an endostatin protein or fragments thereof. In one embodiment, the endostatin protein or fragments have a proline to alanine substitution at the 125 position of human endostatin. In one embodiment, the tumor is known to display vasculogenic mimicry—either in vitro or in vivo.

In one embodiment, this disclosure provides a method for identifying treatment options for an individual diagnosed with a tumor comprising determining if the tumor exhibits vasculogenic mimicry (such as in vitro or in vivo) and if so, determining if the fusion proteins of the present disclosure (such as anti-Her2-huEndoP125A or anti-EGFR-huEndoP125A) inhibit vasculogenic mimicry. If inhibition of vasculogenic mimicry is observed, treatment options can be devised for the individual that employ administration of the fusion proteins.

In one embodiment, this disclosure provides a method for identifying treatment options for an individual diagnosed with a tumor comprising determining if the fusion proteins of the present disclosure (such as anti-Her2-huEndoP125A or anti-EGFR-huEndoP125A) inhibit vasculogenic mimicry in the tumor (such as in vitro or in vivo). If inhibition of vasculogenic mimicry is observed, treatment options can be devised for the individual that employ administration of the fusion proteins.

In another embodiment, the administration of the fusion proteins is combined with other modalities of treatment including surgical removal of the tumor or radiation treatment. The fusion proteins may be administered before, after or during the same time as the other modalities.

Other aspects of the invention are described infra.

BRIEF DESCRIPTION OF THE DRAWINGS

The invention is pointed out with particularity in the appended claims. The above and further advantages of this invention may be better understood by referring to the following description taken in conjunction with the accompanying drawings, in which:

FIG. 1A is a schematic diagram showing anti-HER2 IgG3-human endostatin fusion proteins. The endostatin domains (orange) are indicated by an arrow and expression of anti-HER2 IgG3-CH3-endostatin fusion proteins (wild type and the mutant type P125A). FIG. 1B are scans of photographs showing secreted human endostatin fusion proteins labeled with [$^{35}$S]methionine and immunoprecipitated with Protein A and analyzed under non-reducing and reducing conditions. Anti-HER2 IgG3-C$_H$3-murine endostatin fusion was used as a control.

FIG. 3A: HUVECs ($4 \times 10^4$ cells) were resuspended in 300 μl of full endothelial cell growth medium and treated with the various αHER2-huEndo fusion proteins before plating onto the Matrigel-coated plates. After 16-20 hr of incubation, tube formation was observed through an inverted photomicroscope. Full media was used as negative control (I). Tube formation with αHER2 IgG3 (II. 45.46 nM) and huEndo (III. 45.46 nM) were compared to those with αHER2-huEndo (IV-VI, 4.55, 22.73, 45.46 nM, respectively) and αHER2-huEndo-P125A (VII-IX, 4.55, 22.73, 45.46 nM, respectively). Experiments repeated at least twice. FIG. 3B: HUVECs ($4 \times 10^3$ cells) were treated with increasing concentrations of the endostatin fusion proteins and proliferation measured at 72 hrs. I. VEGF: HUVEC proliferation induced by VEGF (10 ng/ml). II. FGF: HUVEC proliferation induced by bFGF (10 ng/ml). The data are presented as the mean of triplicate determinations±SD. Experiments were repeated twice.

FIG. 4A: Tumor growth was measured with calipers. Tumor volume was calculated as $4/3 \times 3.14 \times \{(\text{long axis}+\text{short axis})/4\}^3$. The values represent mean±SEM of tumor volume (mm$^3$) of 5 mice. FIG. 4B: Survival of mice per treatment group. Mice with greater than 2000 mm$^3$ tumor volume were euthanized.

FIG. 5A: Individual tumor measurements of mice treated with αHER2-huEndo-P125A fusion protein are presented. FIG. 5B: Comparison of tumor growth between untargeted and targeted tumors on day 16. EMT6 and EMT6-HER2 tumor measurements of individual mice are paired and presented. The thick red lines represent average measurements.

DETAILED DESCRIPTION

Figures 2A, 2B, 2C, 2D, 2E, 2F:
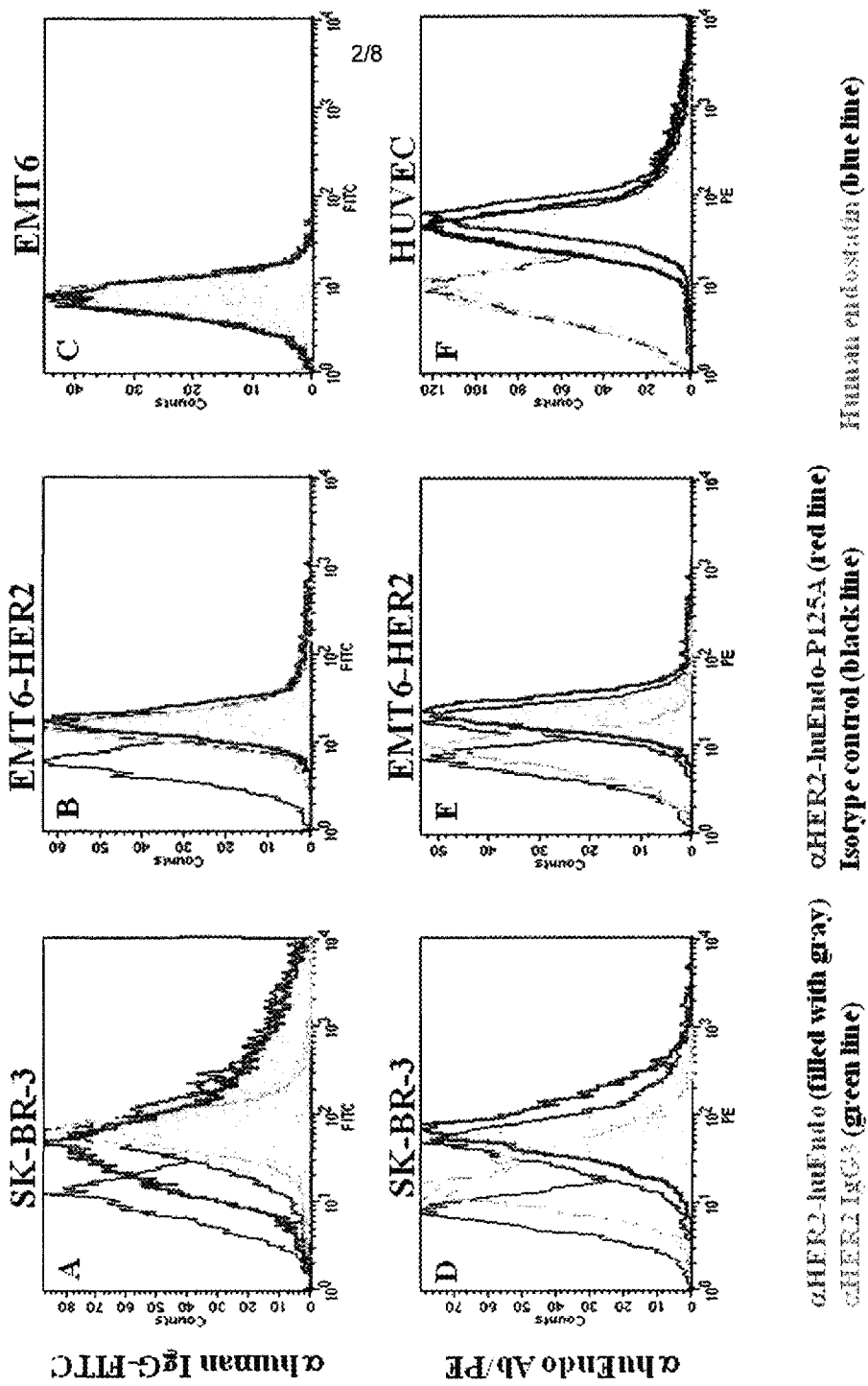
FIGS. 2A-2F is a series of FACS scans shows binding of anti-HER2 human endostatin fusion proteins to HER2 antigen and HUVECs, and recognition by anti-human endostatin antibody. Human breast cancer cells, SK-BR-3 (I, IV), murine mammary tumor cells, EMT6-HER2 (II, V) and EMT6 (III), and HUVECs (VI) were incubated with αHER2-huEndo (thin black line, filled with red), αHER2-huEndo-P125A (thick black line, unfilled), αHER2 IgG3 (thick green line, unfilled), human endostatin (thick blue line), or isotype control (anti-dansyl IgG3, thin black line, filled with gray). The unfilled, thin black line is unstained (the secondary reagents only). The bound fusion proteins were identified with either anti-human IgG-FITC conjugated (I-III), or recognized with biotinylated anti-human endostatin antibody and secondarily stained with a streptavidin-PE conjugate (IV-VI).

The invention provides methods and compositions for targeting a therapeutic chimeric molecule containing both (1) an active agent and (2) a carrier domain such as all or a portion of an immunoglobulin (Ig) molecule, aptamer, to a tumor. The active agent can be modulatory, for example, anti-angiogenic, or cytolytic. Targeting anti-angiogenic proteins using antibody fusion proteins would improve clinical activity of anti-HER2 antibody and endostatin alike, and provides a versatile approach that can be applied to other tumor targets with alternative antibody specificities or using other anti-angiogenic or cytolytic domains.

The below described preferred embodiments illustrate adaptations of these compositions and methods. Nonetheless, from the description of these embodiments, other aspects of the invention can be made and/or practiced based on the description provided below.

Methods involving conventional biological techniques are described herein. Such techniques are generally known in the art and are described in detail in methodology treatises such as Molecular Cloning: A Laboratory Manual, 2nd ed., vol. 1-3, ed. Sambrook et al., Cold Spring Harbor Laboratory Press, Cold Spring Harbor, N.Y., 1989; and Current Protocols in Molecular Biology, ed. Ausubel et al., Greene Publishing and Wiley-Interscience, New York, 1992 (with periodic updates). Immunological methods (e.g., preparation of antigen-specific antibodies, immunoprecipitation, and immunoblotting) are described, e.g., in Current Protocols in Immunology, ed. Coligan et al., John Wiley & Sons, New York, 1991; and Methods of Immunological Analysis, ed. Masseyeff et al., John Wiley & Sons, New York, 1992.

DEFINITIONS

Prior to setting forth the invention, it may be helpful to an understanding thereof to set forth definitions of certain terms that will be used hereinafter.

As used herein, the singular forms "a", "an" and "the" include plural referents unless the context clearly dictates otherwise.

As used herein, "antibody" refers to single chain, two-chain, and multi-chain proteins and glycoproteins belonging to the classes of polyclonal, monoclonal, chimeric, and hetero immunoglobulins (monoclonal antibodies being preferred); it also includes synthetic and genetically engineered variants of these immunoglobulins. "Antibody fragment" includes Fab, Fab', F(ab')$_2$, and Fv fragments, as well as any portion of an antibody having specificity toward a desired target epitope or epitopes.

As used herein, the term "immunoglobulin" or "antibody" are used interchangeably and refer to a protein consisting of one or more polypeptides substantially encoded by immunoglobulin genes. The recognized immunoglobulin genes include the κ, λ, α, γ (IgG1, IgG2, IgG3, IgG4), δ, ε and μ constant region genes, as well as the myriad immunoglobulin variable region genes. Full-length immunoglobulin "light chains" (about 25 KDa or 214 amino acids) are encoded by a variable region gene at the NH$_2$-terminus (about 110 amino acids) and a kappa or lambda constant region gene at the COOH-terminus Full-length immunoglobulin "heavy chains" (about 50 KDa or 446 amino acids), are similarly encoded by a variable region gene (about 116 amino acids) and one of the other aforementioned constant region genes, e.g., gamma (encoding about 330 amino acids). One form of immunoglobulin constitutes the basic structural unit of an antibody. This form is a tetramer and consists of two identical pairs of immunoglobulin chains, each pair having one light and one heavy chain. In each pair, the light and heavy chain variable regions are together responsible for binding to an antigen, and the constant regions are responsible for the antibody effector functions. In addition to antibodies, immunoglobulins may exist in a variety of other forms including, for example, Fv, Fab, and F(ab')$_2$, as well as bifunctional hybrid antibodies (e.g., Lanzavecchia et al., *Eur. J. Immunol.* 17, 105 (1987)) and in single chains (e.g., Huston et al., *Proc. Natl. Acad. Sci. U.S.A.*, 85, 5879-5883 (1988) and Bird et al., *Science*, 242, 423-426 (1988), which are incorporated herein by reference). (See, generally, Hood et al., "Immunology", Benjamin, N.Y., 2nd ed. (1984), and Hunkapiller and Hood, *Nature,* 323, 15-16 (1986), which are incorporated herein by reference). The antibody can be human, humanized or from any desired species.

As used herein, "humanized antibody" refers to an antibody derived from a non-human antibody, typically murine, that retains or substantially retains the antigen-binding properties of the parent antibody but which is less immunogenic in humans. This may be achieved by various methods including (a) grafting only the non-human CDRs onto human framework and constant regions with or without retention of critical framework residues, or (b) transplanting the entire non-human variable domains, but "cloaking" them with a human-like section by replacement of surface residues. Such methods as are useful in practicing the present invention include those disclosed in Morrison et al., *Proc. Nat'l Acad. Sci. USA*, 81:6851-6855 (1984); Morrison and Oi, *Adv. Immunol.*, 44:65-92 (1988); Verhoeyen et al., *Science,* 239:1534-1536 (1988); Padlan, *Mol. Immunol.*, 28:489-498 (1991); Padlan, *Mol. Immunol.*, 31(3):169-217 (1994).

As used herein "chimeric molecule" comprises a targeting sequence such as for example, an aptamer, antibody sequence and a therapeutic effector molecule, e.g. endostatin and mutants thereof, genetically fused to the targeting, e.g. antibody fragment. For example, a chimeric molecule comprises endostatin genetically fused to an anti-HER2/neu IgG3 heavy chain at the end of $C_H3$, and expressed with an anti-HER2/neu K light chain.

As used herein, "variant" in addition to its understood meaning as a term of art includes any changes in a molecule from its wild-type form. For example, alleles, fragments, mutations, substitutions with natural or analog compounds, splice variants, glycosylations, species variants, and the like. The term is not limited to any one type of change or deviation from the wild type form or "normal" molecule.

The phrase "specifically (or selectively) binds" to an antibody or aptamer or "specifically (or selectively) immunoreactive with," refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein. For example, polyclonal antibodies raised to marker "X" from specific species such as rat, mouse, or human can be selected to obtain only those polyclonal antibodies that are specifically immunoreactive with marker "X" and not with other proteins, except for polymorphic variants and alleles of marker "X". This selection may be achieved by subtracting out antibodies that cross-react with marker "X" molecules from other species. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Antibodies, A Laboratory Manual (1988), for a description of immunoassay formats and conditions that can be used to determine specific immunoreactivity). Typically a specific or selective reaction will be at least twice background signal or noise and more typically more than 10 to 100 times background.

As used herein, a "pharmaceutically acceptable" component is one that is suitable for use with humans and/or animals without undue adverse side effects (such as toxicity, irritation, and allergic response) commensurate with a reasonable benefit/risk ratio.

As used herein, the term "safe and effective amount" or "therapeutic amount" refers to the quantity of a component which is sufficient to yield a desired therapeutic response without undue adverse side effects (such as toxicity, irritation, or allergic response) commensurate with a reasonable benefit/risk ratio when used in the manner of this invention. By "therapeutically effective amount" is meant an amount of a compound of the present invention effective to yield the desired therapeutic response. For example, an amount effective to delay the growth of or to cause a cancer, either a sarcoma or lymphoma, or to shrink the cancer or prevent metastasis. The specific safe and effective amount or therapeutically effective amount will vary with such factors as the particular condition being treated, the physical condition of the patient, the type of mammal or animal being treated, the duration of the treatment, the nature of concurrent therapy (if any), and the specific formulations employed and the structure of the compounds or its derivatives.

As used herein, "cancer" refers to all types of cancer or neoplasm, benign or malignant tumors found in mammals, including, but not limited to: leukemias, lymphomas, melanomas, carcinomas and sarcomas. Examples of cancers are cancer of the brain, breast, pancreas, cervix, colon, head and neck, kidney, lung, non-small cell lung, melanoma, mesothelioma, ovary, sarcoma, stomach, prostate, testicles, uterus and medulloblastoma.

Additional cancers which can be treated the chimeric fusion molecule according to the invention include, for example, Hodgkin's Disease, Non-Hodgkin's Lymphoma, multiple myeloma, neuroblastoma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, cervical cancer, endometrial cancer, adrenal cortical cancer, and prostate cancer.

"Regression" refers to the reduction of tumor mass and size as measured using standard techniques.

"Diagnostic" or "diagnosed" means identifying the presence or nature of a pathologic condition. Diagnostic methods differ in their sensitivity and specificity. The "sensitivity" of a diagnostic assay is the percentage of diseased individuals who test positive (percent of "true positives"). Diseased individuals not detected by the assay are "false negatives." Subjects who are not diseased and who test negative in the assay, are termed "true negatives." The "specificity" of a diagnostic assay is 1 minus the false positive rate, where the "false positive" rate is defined as the proportion of those without the disease who test positive. While a particular diagnostic method may not provide a definitive diagnosis of a condition, it suffices if the method provides a positive indication that aids in diagnosis.

The terms "patient" or "individual" are used interchangeably herein, and refers to a mammalian subject to be treated, with human patients being preferred. In some cases, the methods of the invention find use in experimental animals, in veterinary application, and in the development of animal models for disease, including, but not limited to, rodents including mice, rats, and hamsters; and primates.

"Treatment" is an intervention performed with the intention of preventing the development or altering the pathology or symptoms of a disorder. Accordingly, "treatment" refers to both therapeutic treatment and prophylactic or preventative measures. Those in need of treatment include those already with the disorder as well as those in which the disorder is to be prevented. In tumor (e.g., cancer) treatment, a therapeutic agent may directly decrease the pathology of tumor cells, or render the tumor cells more susceptible to treatment by other therapeutic agents, e.g., radiation and/or chemotherapy. As used herein, "ameliorated" or "treatment" refers to a symptom which is approaches a normalized value (for example a value obtained in a healthy patient or individual), e.g., is less than 50% different from a normalized value, preferably is less than about 25% different from a normalized value, more preferably, is less than 10% different from a normalized value, and still more preferably, is not significantly different from a normalized value as determined using routine statistical tests.

The "treatment of cancer or tumor cells", refers to an amount of chimeric fusion molecule, described throughout the specification and in the Examples which follow, capable of invoking one or more of the following effects: (1) inhibition, to some extent, of tumor growth, including, (i) slowing down (ii) inhibiting angiogenesis and (ii) complete growth arrest; (2) reduction in the number of tumor cells; (3) maintaining tumor size; (4) reduction in tumor size; (5) inhibition, including (i) reduction, (ii) slowing down or (iii) complete prevention, of tumor cell infiltration into peripheral organs; (6) inhibition, including (i) reduction, (ii) slowing down or (iii) complete prevention, of metastasis; (7) enhancement of anti-tumor immune response, which may result in (i) maintaining tumor size, (ii) reducing tumor size, (iii) slowing the growth of a tumor, (iv) reducing, slowing or preventing invasion and/or (8) relief, to some extent, of the severity or number of one or more symptoms associated with the disorder.

As used herein, "metronomic" therapy refers to the administration of continuous low-doses of a therapeutic agent and/or chimeric fusion molecule described herein.)

Fusion Molecules

In general, the invention provides antigen-binding fusion proteins with a therapeutically effective domain which can be a modulatory or cytolytic moiety having a significant serum half-life ($t_{1/2}$) beyond that of either antibody or modulatory/cytolytic moiety alone. Modulatory and cytolytic antigen-binding fusion proteins have more than an antigen-binding site activity or function. A modulatory or cytolytic moiety on the fusion antigen-binding protein will impart upon the protein certain or all of the modulatory or cytolytic attributes of the fusion partner or partners.

Accordingly, the invention is directed to chimeric fusion molecules comprising single or multivalent therapeutically active domains which can be modulatory and/or cytolytic and an antigen-binding domain; compositions of single-chain and multivalent modulatory and cytolytic antigen-binding fusion proteins, methods of making and purifying single-chain and multivalent modulatory and cytolytic antigen-binding fusion proteins, and uses for single-chain and multivalent modulatory and cytolytic antigen-binding fusion proteins. The invention provides a modulatory or cytolytic antigen-binding fusion protein having at least one single-chain antigen-binding protein molecule. Each single-chain antigen-binding molecule has a first polypeptide and a second polypeptide and can be joined by a linker. Each of the polypeptides has the binding portion of the variable region of an antibody heavy or light chain or other antigen specific moiety such as an aptamer. Other binding moieties include integrin motifs and NGR motifs. FIG. 1A is a schematic representation, which is not meant to be limiting or construed as such, shows one embodiment of the chimeric molecule.

In a preferred embodiment, a composition is provided comprising a therapeutically effective anti-tumor molecule fused to a targeting moiety such as for example, an antigen specific binding domain of an antibody. By way of illustration, the composition comprises an anti-tumor antibody specific, for example, the HER2/neu tumor antigen, in which endostatin and/or mutants thereof, is fused to the 3' end of a humanized or human anti-HER2 IgG3 antibody.

In a preferred embodiment, the endostatin molecule comprises a mutation at amino acid 125 whereby the proline is substituted with alanine. Introduction of a point mutation into human endostatin at position 125 (proline to alanine; huEndo-P125A) enhances endothelial cell binding, anti-angiogenic activity, and anti-tumor activity as compared to the wild type endostatin molecule. The mutant αHER2-huEndo-P125A fusion variant inhibited tube formation of HUVEC in vitro and tumor growth in vivo more effectively than αHER2-huEndo.

In another preferred embodiment, the endostatin molecule and mutants thereof comprise one or more NGR motifs (Asn-Gly-Arg). Human endostatin comprises an NGR motif (Asn-Gly-Arg) at position 126-128 following the proline at position 125. In a preferred embodiment, the endostatin molecule comprises one or more NGR motifs at the amino ($NH_2$—) terminal, and/or carboxy terminal (COOH—) and/or a repeating string of NGR molecules following the NGR motif at position 126-128 or preceding the proline or alanine at position 125.

In another preferred embodiment, the endostatin molecule comprises an RGD motif preceding or following the proline or alanine at amino acid position 125.

In another preferred embodiment, the endostatin molecule comprises a mutant endostatin having an amino acid substitution at positions 6-49, 50-92, 93-133 and 134-178 of the endostatin molecule. The amino acids comprise any natural, non-natural, variant, analog, substituted molecule. The molecule further comprises one or more substitutions comprising integrins or integrin like motifs comprising NGR, RGD and the like. These motifs can be at one or more amino acid positions 6-49, 50-92, 93-133 and 134-178 of the endostatin molecule. Thus, one of skill in the art would understand that the chimeric fusion molecule can contain multimers of endostatin molecules and these molecules can be combinations of the same endostatin molecules or comprise combinations of endostatin molecules, molecules with amino acid substitutions, molecules with amino acid substitutions and integrin and integrin like motifs and various positions in the endostatin molecule.

In another preferred embodiment, the chimeric molecule comprises an integrin motif e.g. RGD, in addition to or in place of the NGR motif.

The chimeric fusion molecule can be fused genetically, i.e. the molecules are operably linked in frame so the chimeric fusion molecule is encoded from the nucleic acid molecule. The molecule can be fused at the amino acid level, such as described in detail in the examples which follow.

In another preferred embodiment, the molecule comprises a label for detecting the fusion molecule in vivo and to monitor the effects of the chimeric molecule during therapy.

"Detectable moiety" or a "label" refers to a composition detectable by spectroscopic, photochemical, biochemical, immunochemical, or chemical means. For example, useful labels include $^{32}P$, $^{35}S$, fluorescent dyes, electron-dense reagents, enzymes (e.g., as commonly used in an ELISA), biotin-streptavidin, dioxigenin, haptens and proteins for which antisera or monoclonal antibodies are available, or nucleic acid molecules with a sequence complementary to a target. The detectable moiety often generates a measurable signal, such as a radioactive, chromogenic, or fluorescent signal, that can be used to quantify the amount of bound detectable moiety in a sample. Quantitation of the signal is achieved by, e.g., scintillation counting, densitometry, or flow cytometry.

In a preferred embodiment, the chimeric fusion molecule comprises a polynucleotide sequence encoding an anti-HER2 antibody-human endostatin P125A molecule, variants, mutations, alleles, substitutes, fragments and analogs thereof.

In another preferred embodiment, the chimeric fusion molecule comprises a polypeptide comprising an anti-HER2 specific antibody fused to human endostatin P125A. The endostatin can be a monomer, however, multimers such as for example, a dimer and trimer of endostatin and mutants thereof are preferred.

In another preferred embodiment, the multimer comprises an endostatin molecule and a mutant form of endostatin, for example, P125A endostatin and combinations thereof. Thus, if the multimer is a trimer, then the molecule can comprise a wild type endostatin molecule and two mutant forms of endostatin, or two wild type endostatin molecules and one mutant endostatin molecule; or three wild type endostatin molecules or three mutant forms of endostatin molecules.

In another preferred embodiment, the dimer comprises a mutant form of endostatin, for example, P125A endostatin and normal or wild type endostatin; or combinations thereof, variants, mutations, alleles, substitutes, fragments and analogs thereof.

In another preferred embodiment, the endostatin is human endostatin, variants and alleles thereof. However, endostatin can be derived from any species.

In another preferred embodiment, the endostatin molecule comprises a polynucleotide having mutations at one or more nucleotides encoding mutant endostatin, for example, P125A endostatin.

In all embodiments, the molecules can be in any stereoisomeric form, for example, enantiomers, diastereomers, tautomers and the like. In all embodiments, the fusion molecule or parts thereof includes all variants, mutations, alleles, substitutes, fragments and analogs thereof.

In another preferred embodiment, the endostatin comprises one or more amino acid at position 125. In one embodiment, proline to alanine is preferred. However, other amino acid substitutions can be made, for example, any of the 20 common, genetically-encoded amino acids such as: tryptophan, valine, leucine, isoleucine. Other amino acids include those classified as having, for example: charged polar side chains (Arg, His, Lys etc); uncharged polar side chains (Thr, Asn, Gln etc).

In another preferred embodiment, the amino acid mutations can occur at any one or more amino acid positions 4 to 49, 50-92, 93-133 and 134-178. Preferably, the mutations are in one or more nucleic acids encoding amino acid at positions 93-133 and/or at the amino acid level at amino acid positions 93-133.

The mutations can be introduced at the nucleic acid level or at the amino acid level. With respect to particular nucleic acid sequences, because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. If mutations at the nucleic acid level are introduced to encode a particular amino acid, then one or more nucleic acids are altered. For example proline is encoded by CCC, CCA, CCG, CCU; thus, one base change, e.g. CCC (proline) to GCC gives rise to alanine. Thus by way of example every natural or non-natural nucleic acid sequence herein which encodes a natural or non-natural polypeptide also describes every possible silent variation of the natural or non-natural nucleic acid. One of skill will recognize that each codon in a natural or non-natural nucleic acid (except AUG, which is ordinarily the only codon for methionine, and TGG, which is ordinarily the only codon for tryptophan) can be modified to yield a functionally identical molecule or a different molecule. Accordingly, each silent variation of a natural and non-natural nucleic acid which encodes a natural and non-natural polypeptide is implicit in each described sequence.

As to amino acid sequences, individual substitutions, deletions or additions to a nucleic acid, peptide, polypeptide, or protein sequence which alters, adds or deletes a single natural and non-natural amino acid or a small percentage of natural and non-natural amino acids in the encoded sequence, the alteration results in the deletion of an amino acid, addition of an amino acid, or substitution of a natural and non-natural amino acid with a chemically similar amino acid. Conservative substitution tables providing functionally similar natural amino acids are well known in the art. Such conservatively modified variants are in addition to and do not exclude polymorphic variants, interspecies homologs, and alleles of the methods and compositions described herein.

In another preferred embodiment, the mutant endostatin comprises one or more non-natural or analogs of amino acids.

A "non-natural amino acid" refers to an amino acid that is not one of the 20 common amino acids or pyrolysine or selenocysteine. Other terms that may be used synonymously with the term "non-natural amino acid" is "non-naturally encoded amino acid," "unnatural amino acid," "non-naturally-occurring amino acid," and variously hyphenated and non-hyphenated versions thereof. The term "non-natural amino acid" includes, but is not limited to, amino acids which occur naturally by modification of a naturally encoded amino acid (including but not limited to, the 20 common amino acids or pyrrolysine and selenocysteine) but are not themselves incorporated, without user manipulation, into a growing polypeptide chain by the translation complex. Examples of naturally-occurring amino acids that are not naturally-encoded include, but are not limited to, N-acetylglucosaminyl-L-serine, N-acetylglucosaminyl-L-threonine, and O-phosphotyrosine. Additionally, the term "non-natural amino acid" includes, but is not limited to, amino acids which do not occur naturally and may be obtained synthetically or may be obtained by modification of non-natural amino acids.

In some cases, the non-natural amino acid substitution(s) or incorporation(s) will be combined with other additions, substitutions, or deletions within the polypeptide to affect other chemical, physical, pharmacologic and/or biological traits. In some cases, the other additions, substitutions or deletions may increase the stability (including but not limited to, resistance to proteolytic degradation) of the polypeptide or increase affinity of the polypeptide for its appropriate receptor, ligand and/or binding proteins. In some cases, the other additions, substitutions or deletions may increase the solubility of the polypeptide. In some embodiments sites are selected for substitution with a naturally encoded or non-natural amino acid in addition to another site for incorporation of a non-natural amino acid for the purpose of increasing the polypeptide solubility following expression in recombinant host cells. In some embodiments, the polypeptides comprise another addition, substitution, or deletion that modulates affinity for the associated ligand, binding proteins, and/or receptor, modulates (including but not limited to, increases or decreases) receptor dimerization, stabilizes receptor dimers, modulates circulating half-life, modulates release or bio-availability, facilitates purification, or improves or alters a particular route of administration. Similarly, the non-natural amino acid polypeptide can comprise chemical or enzyme cleavage sequences, protease cleavage sequences, reactive groups, antibody-binding domains (including but not limited to, FLAG or poly-His) or other affinity based sequences (including but not limited to, FLAG, poly-His, GST, etc.) or linked molecules (including but not limited to, biotin) that improve detection (including but not limited to, GFP), purification, transport thru tissues or cell membranes, prodrug release or activation, size reduction, or other traits of the polypeptide.

The methods and compositions described herein include incorporation of one or more non-natural amino acids into a polypeptide. One or more non-natural amino acids may be incorporated at one or more particular positions which does not disrupt activity of the polypeptide. This can be achieved by making "conservative" substitutions, including but not limited to, substituting hydrophobic amino acids with non-natural or natural hydrophobic amino acids, bulky amino acids with non-natural or natural bulky amino acids, hydrophilic amino acids with non-natural or natural hydrophilic amino acids) and/or inserting the non-natural amino acid in a location that is not required for activity.

A variety of biochemical and structural approaches can be employed to select the desired sites for substitution with a non-natural amino acid within the polypeptide. Any position of the polypeptide chain is suitable for selection to incorporate a non-natural amino acid, and selection may be based on rational design or by random selection for any or no particular desired purpose. Selection of desired sites may be based on producing a non-natural amino acid polypeptide (which may be further modified or remain unmodified) having any desired property or activity, including but not limited to agonists, super-agonists, partial agonists, inverse agonists, antagonists, receptor binding modulators, receptor activity modulators, modulators of binding to binder partners, binding partner activity modulators, binding partner conformation modulators, dimer or multimer formation, no change to activity or property compared to the native molecule, or manipulating any physical or chemical property of the polypeptide such as solubility, aggregation, or stability. For example, locations in the polypeptide required for biological activity of a polypeptide can be identified using methods including, but not limited to, point mutation analysis, alanine scanning or homolog scanning methods. Residues other than those identified as critical to biological activity by methods including, but not limited to, alanine or homolog scanning mutagenesis may be good candidates for substitution with a non-natural amino acid depending on the desired activity sought for the polypeptide. Alternatively, the sites identified as critical to biological activity may also be good candidates for substitution with a non-natural amino acid, again depending on the desired activity sought for the polypeptide. Another alternative would be to make serial substitutions in each position on the polypeptide chain with a non-natural amino acid and observe the effect on the activities of the polypeptide. Any means, technique, or method for selecting a position for substitution with a non-natural amino acid into any polypeptide is suitable for use in the methods, techniques and compositions described herein.

The structure and activity of naturally-occurring mutants of a polypeptide that contain deletions can also be examined to determine regions of the protein that are likely to be tolerant of substitution with a non-natural amino acid. Once residues that are likely to be intolerant to substitution with non-natural amino acids have been eliminated, the impact of proposed substitutions at each of the remaining positions can be examined using methods including, but not limited to, the three-dimensional structure of the relevant polypeptide, and any associated ligands or binding proteins. X-ray crystallographic and NMR structures of many polypeptides are available in the Protein Data Bank (PDB, www.rcsb.org), a centralized database containing three-dimensional structural data of large molecules of proteins and nucleic acids, one can be used to identify amino acid positions that can be substituted with non-natural amino acids. In addition, models may be made investigating the secondary and tertiary structure of polypeptides, if three-dimensional structural data is not available. Thus, the identity of amino acid positions that can be substituted with non-natural amino acids can be readily obtained. Exemplary sites of incorporation of a non-natural amino acid include, but are not limited to, those that are excluded from potential receptor binding regions, or regions for binding to binding proteins or ligands may be fully or partially solvent exposed, have minimal or no hydrogen-bonding interactions with nearby residues, may be minimally exposed to nearby reactive residues, and/or may be in regions that are highly flexible as predicted by the three-dimensional crystal structure of a particular polypeptide with its associated receptor, ligand or binding proteins.

A wide variety of non-natural amino acids can be substituted for, or incorporated into, a given position in a polypeptide. By way of example, a particular non-natural amino acid may be selected for incorporation based on an examination of the three dimensional crystal structure of a polypeptide with its associated ligand, receptor and/or binding proteins, a preference for conservative substitutions Other Therapeutic Effector Domains:

In another preferred embodiment, the modulatory domain comprises endostatin, angiogenin, angiostatin, chemokines, angioarrestin, angiostatin (plasminogen fragment), basement-membrane collagen-derived anti-angiogenic factors (tumstatin, canstatin, or arrestin), anti-angiogenic antithrombin III, signal transduction inhibitors, cartilage-derived inhibitor (CDI), CD59 complement fragment, fibronectin fragment, gro-beta, heparinases, heparin hexasaccharide fragment, human chorionic gonadotropin (hCG), interferon alpha/beta/gamma, interferon inducible protein (IP-10), interleukin-12, kringle 5 (plasminogen fragment), metalloproteinase inhibitors (TIMPs), 2-methoxyestradiol, placental ribonuclease inhibitor, plasminogen activator inhibitor, platelet factor-4 (PF4), prolactin 16 kD fragment, proliferin-related protein (PRP), various retinoids, tetrahydrocortisol-S, thrombospondin-1 (TSP-1), transforming growth factor-beta (TGF-b), vasculostatin, vasostatin (calreticulin fragment) and the like. These molecules include all forms, variants, mutations, alleles, substitutes, fragments and analogs thereof.

In another preferred embodiment, the modulatory domain of the chimeric fusion molecule comprises endostatin, angiostatin, tumstatin, arrestin and canstatin, variants, mutations, alleles, substitutes, fragments and analogs thereof.

In another preferred embodiment, the molecule comprises combinations of one or more of endostatin, angiostatin, tumstatin, arrestin and canstatin, variants, mutations, alleles, substitutes, fragments and analogs thereof.

In another preferred embodiment, the targeting domain comprises antibody, aptamer, a ligand for a receptor (e.g. VEGF), diabodies, peptides, lipopolysaccharides, integrins and the like.

Other Specificities of the Antigen Binding Domain:

In another preferred embodiment, the chimeric fusion molecules comprise an antigen binding domain specific for other tumor antigens. The antigen binding domain can be an antibody or aptamer, receptor, ligand etc.

In one preferred embodiment, the invention provides for antibody fusion molecules comprising: $F_e$ region, $C_H1$, $C_H2$ and/or $C_H3$, Fab, Fab', F(ab')$_2$, single chain Fv ($S_cFv$) and Fv fragments, as well as any portion of an antibody having specificity toward a desired target epitope or epitopes. Also preferred are antibodies or antibody fragments or to single chain, two-chain, and multi-chain proteins and glycoproteins belonging to the classes of polyclonal, monoclonal, chimeric, bispecific and hetero immunoglobulins (monoclonal antibodies being preferred); it also includes synthetic and genetically engineered variants of these immunoglobulins.

In another preferred embodiment, the antigen binding domain is an aptamer. In the preferred embodiment, the chimeric molecule comprises an aptamer fused to the endostatin molecule, variants, mutants and fragments thereof. The aptamer can be specific for any one or more tumor antigens.

As used herein, the term "aptamer" or "selected nucleic acid binding species" refers to short strands of nucleic acid sequences, DNA or RNA, that are designed to bind to a target molecule specifically and with high affinity. The nucleic acid sequences include non-modified or chemically modified RNA or DNA. The method of selection may be by, but is not limited to, affinity chromatography and the method of amplification by reverse transcription (RT) or polymerase chain reaction (PCR), iterative rounds using SELEX aptamer techniques and the like.

Many tumor antigens are well known in the art. See for example, Van den Eynde B J, van der Bruggen P. *Curr Opin Immunol* 1997; 9: 684-93; Houghton A N, Gold J S, Blachere N E. *Curr Opin Immunol* 2001; 13: 134-140; van der Bruggen P, Zhang Y, Chaux P, Stroobant V, Panichelli C, Schultz E S, Chapiro J, Van den Eynde B J, Brasseur F, Boon T. *Immunol Rev* 2002; 188: 51-64, which are herein incorporated by reference in their entirety. Alternatively, many antibodies directed towards tumor antigens are commercially available.

In a preferred embodiment, the tumor antigens comprise HER2, HER3, Muc-1, EGFR, PSMA, CD20, CD22, CD23, TAA, GDR antigens, VEGFR and the like.

Other non-limiting examples of tumor antigens, include, tumor antigens resulting from mutations, such as: alpha-actinin-4 (lung carcinoma); CASP-8 (head and neck squamous cell carcinoma); beta-catenin (melanoma); Cdc27 (melanoma); CDK4 (melanoma); Elongation factor 2 (lung squamous carcinoma); LDLR-fucosyltransferaseAS fusion protein (melanoma); overexpression of HLA-A2$^d$ (renal cell carcinoma); hsp70-2 (renal cell carcinoma); KIAA0205 (bladder tumor); MART2 (melanoma); MUM-1f (melanoma); MUM-2 (melanoma); MUM-3 (melanoma); neo-PAP (melanoma); Myosin class I (melanoma); OS-9g (melanoma); PTPRK (melanoma). Examples of differentiation tumor antigens include, but not limited to: CEA (gut carcinoma); gp100/Pme117 (melanoma); Kallikrein 4 (prostate); mammaglobin-A (breast cancer); Melan-A/MART-1 (melanoma); PSA (prostate carcinoma); TRP-1/gp75 (melanoma); TRP-2 (melanoma); tyrosinase (melanoma). Over or under-expressed tumor antigens include but are not limited to: CPSF (ubiquitous); EphA3; G250/MN/CAIX (stomach, liver, pancreas); HER-2/neu; Intestinal carboxyl esterase (liver, intestine, kidney); alpha-foetoprotein (liver); M-CSF (liver, kidney); MUC1 (glandular epithelia); p53 (ubiquitous); PRAME (testis, ovary, endometrium, adrenals); PSMA (prostate, CNS, liver); RAGE-1 (retina); RU2AS (testis, kidney, bladder); survivin (ubiquitous); Telomerase (testis, thymus, bone marrow, lymph nodes); WT1 (testis, ovary, bone marrow, spleen); CA125 (ovarian). Antigens that are preferentially expressed on the tumor cell membrane represent preferred targets.

In another preferred embodiment, the present invention features a compound having a plurality of binding moieties, wherein at least two binding moieties have specificity for different binding sites on the same target. In preferred embodiments, the plurality of binding moieties includes a polypeptide. In other preferred embodiments, the targeting moieties are all binding polypeptides which bind to different sites on the desired target. In certain preferred embodiments, the target is a protein, a receptor, or a receptor/ligand complex and the binding polypeptides bind to different epitopes on the protein, the receptor, or the receptor/ligand complex.

In another preferred embodiment, the target is a receptor involved in angiogenesis, hyperproliferative disorders or wound healing. In another embodiment the target includes a family of receptors, such as, for example, protein-tyrosine kinase receptors. In a particularly preferred embodiment, the target is Flt-1 and KDR, VEGF (VEGF-1, -2 or -3) or the KDR/VEGF and Flt-1/VEGF complexes, and the binding moieties, particularly binding peptides, bind to different epitopes on Flt-1 and KDR or the KDR/VEGF and Flt-1/VEGF complexes. For example, VEGFR-2/KDR, VEGFR-1/Flt-1 and VEGFR-3/Flt-4.

In connection with solid tumor treatment, the present invention may be used in combination with classical approaches, such as surgery, radiotherapy, chemotherapy, and the like. The invention therefore provides combined therapies in which the therapeutic compositions are used simultaneously with, before, or after surgery or radiation treatment; or are administered to patients with, before, or after conventional chemotherapeutic, radiotherapeutic or other anti-angiogenic agents, or targeted immunotoxins or coaguligands.

In another preferred embodiments, the chimeric molecule comprises one or more cytolytic or other effector molecules. Cytolytic molecules that can be used to fuse to an antibody or fragment thereof, include, but are not limited to TNF-α, TNF-β, suitable effector genes such as those that encode a peptide toxin—such as ricin, abrin, diphtheria, gelonin, *Pseudomonas* exotoxin A, *Crotalus durissus terrificus* toxin, *Crotalus adamenteus* toxin, *Naja naja* toxin, and *Naja mocambique* toxin. (Hughes et al., *Hum. Exp. Toxicol.* 15:443, 1996; Rosenblum et al., *Cancer Immunol. Immunother.* 42:115, 1996; Rodriguez et al., Prostate 34:259, 1998; Mauceri et al., Cancer Res. 56:4311; 1996).

ALSO suitable are genes that induce or mediate apoptosis—such as the ICE-family of cysteine proteases, the Bcl-2 family of proteins, Bax, BclXs and caspases (Favrot et al., *Gene Ther.* 5:728, 1998; McGill et al., *Front. Biosci.* 2:D353, 1997; McDonnell et al., *Semin. Cancer Biol.* 6:53, 1995). Another potential anti-tumor agent is apoptin, a protein that induces apoptosis even where small drug chemotherapeutics fail (Pietersen et al., *Adv. Exp. Med. Biol.* 465:153, 2000). Koga et al. (*Hu. Gene Ther.* 11: 1397, 2000) propose a telomerase-specific gene therapy using the hTERT gene promoter linked to the apoptosis gene Caspase-8 (FLICE).

Also of interest are enzymes present in the lytic package that cytotoxic T lymphocytes or LAK cells deliver to their targets. Perforin, a pore-forming protein, and Fas ligand are major cytolytic molecules in these cells (Brandau et al., *Clin. Cancer Res.* 6:3729, 2000; Cruz et al., *Br. J. Cancer* 81:881, 1999). CTLs also express a family of at least 11 serine proteases termed granzymes, which have four primary substrate specificities (Kam et al., *Biochim. Biophys. Acta* 1477:307, 2000). Low concentrations of streptolysin 0 and pneumolysin facilitate granzyme B-dependent apoptosis (Browne et al., *Mol. Cell. Biol.* 19:8604, 1999).

Other suitable effectors encode polypeptides having activity that is not itself toxic to a cell, but renders the cell sensitive to an otherwise nontoxic compound—either by metabolically altering the cell, or by changing a non-toxic prodrug into a lethal drug. Exemplary is thymidine kinase (tk), such as may be derived from a herpes simplex virus, and catalytically equivalent variants. The HSV tk converts the anti-herpetic agent ganciclovir (GCV) to a toxic product that interferes with DNA replication in proliferating cells.

If desired, although not required, factors may also be included, such as, but not limited to, chemokines, cytokines, e.g. interleukins, e.g. IL-2, IL-3, IL-6, and IL-11, as well as the other interleukins, the colony stimulating factors, such as GM-CSF, interferons, e.g. γ-interferon, erythropoietin.

Combination Therapies

In another preferred embodiment, the invention provides administering the chimeric fusion molecule with a cocktail of one or more compounds such as for example, endostatin, angiogenin, angiostatin, chemokines, angioarrestin, angiostatin (plasminogen fragment), basement-membrane collagen-derived anti-angiogenic factors (tumstatin, canstatin, or arrestin), anti-angiogenic antithrombin III, cartilage-derived inhibitor (CDI), CD59 complement fragment, fibronectin fragment, gro-beta, heparinases, heparin hexasaccharide fragment, human chorionic gonadotropin (hCG), interferon alpha/beta/gamma, interferon inducible protein (IP-10), interleukin-12, kringle 5 (plasminogen fragment), metalloproteinase inhibitors (TIMPs), 2-methoxyestradiol, placental ribonuclease inhibitor, plasminogen activator inhibitor, platelet factor-4 (PF4), prolactin 16 kD fragment, proliferin-related protein (PRP), various retinoids, tetrahydrocortisol-S, thrombospondin-1 (TSP-1), transforming growth factor-beta (TGF-b), vasculostatin, vasostatin (calreticulin fragment) and the like.

In another preferred embodiment, the chimeric fusion molecules of the invention are administered with one more compounds comprising signal transduction inhibitors, bevacizumab (Avastin), antiangiogenic compounds such as for example, sunitinib, sorafenib, celebrex, MTOR inhibitors, AKT inhibitors, P13K and the like. One of ordinary skill in the art would identify which other therapeutic compounds could be administered in conjunction with a therapy comprising a regimen of chimeric fusion molecule.

In another preferred embodiment, one or more types of chimeric fusion molecules can be administered to a patient. For example a chimeric fusion molecule wherein the therapeutic effector domain comprises endostatin, angiogenin, angiostatin, chemokines, angioarrestin, angiostatin (plasminogen fragment), basement-membrane collagen-derived anti-angiogenic factors (tumstatin, canstatin, or arrestin), anti-angiogenic antithrombin III, signal transduction inhibitors, cartilage-derived inhibitor (CDI), CD59 complement fragment, fibronectin fragment, gro-beta, heparinases, heparin hexasaccharide fragment, human chorionic gonadotropin (hCG), interferon alpha/beta/gamma, interferon inducible protein (IP-10), interleukin-12, kringle 5 (plasminogen fragment), metalloproteinase inhibitors (TIMPs), 2-methoxyestradiol, placental ribonuclease inhibitor, plasminogen activator inhibitor, platelet factor-4 (PF4), prolactin 16 kD fragment, proliferin-related protein (PRP), various retinoids, tetrahydrocortisol-S, thrombospondin-1 (TSP-1), transforming growth factor-beta (TGF-b), vasculostatin, vasostatin (calreticulin fragment) and the like. These molecules include all forms, variants, mutations, alleles, substitutes, fragments and analogs thereof.

Metronomic Therapy:

In accordance with the invention, the chimeric fusion molecule composition is administered to a patient in combination with metronomic therapy. For example, administration of continuous low-doses of the chimeric fusion molecule and one or more therapeutic agents. Therapeutic agents can include, for example, chemotherapeutic agents such as, cyclophosphamide (CTX, 25 mg/kg/day, p.o.), taxanes (paclitaxel or docetaxel), busulfan, cisplatin, cyclophosphamide, methotrexate, daunorubicin, doxorubicin, melphalan, cladribine, vincristine, vinblastine, and chlorambucil. Metronomic therapy can also include administering the antibody-fusion molecule with a cocktail of one or more compounds such as for example, endostatin, angiogenin, angiostatin, chemokines, angioarrestin, angiostatin (plasminogen fragment), basement-membrane collagen-derived anti-angiogenic factors (tumstatin, canstatin, or arrestin), anti-angiogenic antithrombin III, cartilage-derived inhibitor (CDI), CD59 complement fragment, fibronectin fragment, gro-beta, heparinases, heparin hexasaccharide fragment, human chorionic gonadotropin (hCG), interferon alpha/beta/gamma, interferon inducible protein (IP-10), interleukin-12, kringle 5 (plasminogen fragment), metalloproteinase inhibitors (TIMPs), 2-methoxyestradiol, placental ribonuclease inhibitor, plasminogen activator inhibitor, platelet factor-4 (PF4), prolactin 16 kD fragment, proliferin-related protein (PRP), various retinoids, tetrahydrocortisol-S, thrombospondin-1 (TSP-1), transforming growth factor-beta (TGF-b), vasculostatin, vasostatin (calreticulin fragment), signal transduction inhibitors and the like. Other examples include antibodies that target signal transduction receptors, ligands and/or complexes thereof.

Examples of signal transduction inhibitors include, but not limited to: Gleevec (target Bcr-abl), Herceptin (monoclonal antibody—target Her-2 (neu)), Iressa (small molecule inhibitor—EGFR), Erbitux (monoclonal antibody—EGFR), Tarceva (small molecule inhibitor) Ras inhibitor R11577 (farnesyl transferase inhibitor), mTOR inhibitor Rapamune (rapamycin) Ruboxistaurin (small molecule inhibitor), Avastin (monoclonal antibody), PTK787/ZK 222584, Neovastat, ABX-EGF (monoclonal antibody), TheraCIM (monoclonal antibody), Mixed lineages kinases-CEP1347 (small molecule inhibitor), Tyrosine kinase—CEP 701 (small molecule inhibitor), Cyclin dependent kinase—Flavopiridol (small molecule inhibitor), VEGF Trap (decoy receptor).

In another preferred embodiment, the chimeric fusion protein molecules can be administered with one or anti-cancer compounds. The compounds of this invention may also be useful in combination (administered together or sequentially) with known anti-cancer treatments such as radiation therapy or with cytostatic or cytotoxic agents, such as for example, but not limited to, DNA interactive agents, such as cisplatin or doxorubicin; topoisomerase II inhibitors, such as etoposide; topoisomerase I inhibitors such as CPT-11 or topotecan; tubulin interacting agents, such as paclitaxel, docetaxel or the epothilones; hormonal agents, such as tamoxifen; thymidilate synthase inhibitors, such as 5-fluorouracil; and anti-metabolites, such as methotrexate; tyrosine kinase inhibitors such as Iressa and OSI-774 (Tarceva™); bevacizumab (Avastin), Herceptin, angiogenesis inhibitors; EGF inhibitors; VEGF inhibitors; CDK inhibitors; Her1/2 inhibitors and monoclonal antibodies directed against growth factor receptors such as erbitux (EGF) and herceptin (Her2) or against angiogenic factors.

Examples of tyrosine kinase inhibitors include inhibitors of the tyrosine kinase enzyme: Abl, CDK's, EGF, EMT, FGF, FAK, Flk-1/KDR, HER-2, IGF-R, IR, LCK, MET, PDGF, Src, and VEGF. In general, inhibitors could act as reversible cytostatic agents which may be useful in the treatment of any disease process which features abnormal cellular proliferation, e.g., benign prostatic hyperplasia, familial adenomatosis polyposis, neuro-fibromatosis, atherosclerosis, pulmonary fibrosis, arthritis, psoriasis, glomerulonephritis, restenosis following angioplasty or vascular surgery, hypertrophic scar formation, inflammatory bowel disease, transplantation rejection, endotoxic shock, and fungal infections.

In another preferred embodiment, the treatment of abnormal cell growth or cancer comprises a combination treatment in which endostatin fusion molecules of the invention are administered to a subject in combination with radiation therapy and/or chemotherapy.

The language "chemotherapeutic agent" is intended to include chemical reagents which inhibit the growth of proliferating cells or tissues wherein the growth of such cells or tissues is undesirable. Chemotherapeutic agents are well known in the art (see e.g., Gilman A. G., et al. The Pharmacological Basis of Therapeutics, 8th Ed., Sec 12:1202-1263 (1990)), and are typically used to treat neoplastic diseases, tumors, and cancers.

The language "radiation therapy" is intended to include the application of a genetically and somatically safe level of X-rays, both localized and non-localized, to a subject to inhibit, reduce, or prevent symptoms or conditions associated with undesirable cell growth. The term X-rays is intended to include clinically acceptable radioactive elements and isotopes thereof, as well as the radioactive emissions therefrom. Examples of the types of emissions include alpha rays, beta rays including hard betas, high energy electrons, and gamma rays. Radiation therapy is well known in the art (see e.g., Fishbach, F., Laboratory Diagnostic Tests, 3rd Ed., Ch. 10: 581-644 (1988)), and is typically used to treat neoplastic diseases, tumors, and cancers.

Examples of chemotherapeutic agents include: bleomycin, docetaxel (Taxotere), doxorubicin, edatrexate, etoposide, finasteride (Proscar), flutamide (Eulexin), gemcitabine (Gemzar), goserelin acetate (Zoladex), irinotecan (Campto/Camptosar), ondansetron (Zofran), paclitaxel (Taxol), pegaspargase (Oncaspar), pilocarpine hydrochloride (Salagen), porfimer sodium (Photofrin), interleukin-2 (Proleukin), rituximab (Rituxan), topotecan (Hycamtin), trastuzumab (Herceptin), tretinoin (Retin-A), Triapine, vincristine, and vinorelbine tartrate (Navelbine). Other examples of chemotherapeutic agents include alkylating drugs such as Nitrogen Mustards (e.g., Mechlorethamine ($HN_2$), Cyclophosphamide, Ifosfamide, Melphalan (L-sarcolysin), Chlorambucil, etc.); ethylenimines, methylmelamines (e.g., Hexamethylmelamine, Thiotepa, etc.); Alkyl Sulfonates (e.g., Busulfan, etc.), Nitrosoureas (e.g., Carmustine (BCNU), Lomustine (CCNU), Semustine (methyl-CCNU), Streptozocin (streptozotocin), etc.), triazenes (e.g., Decarbazine (DTIC; dimethyltriazenoimi-dazolecarboxamide)), Alkylators (e.g., cis-diamminedichloroplatinum II (CDDP)), etc.

Other examples of chemotherapeutic agents include antimetabolites such as folic acid analogs (e.g., Methotrexate (amethopterin)); pyrimidine analogs (e.g., fluorouracil ('5-fluorouracil; 5-FU); floxuridine (fluorode-oxyuridine); Fudr; Cytarabine (cyosine arabinoside), etc.); purine analogs (e.g., Mercaptopurine (6-mercaptopurine; 6-MP); Thioguanine (6-thioguanine; TG); and Pentostatin (2'-deoxycoformycin)), etc. Other examples of chemotherapeutic agents also include vinca alkaloids (e.g., Vinblastin (VLB) and Vincristine); topoisomerase inhibitors (e.g., Etoposide, Teniposide, Camptothecin, Topotecan, 9-amino-campotothecin CPT-11, etc.); antibiotics (e.g., Dactinomycin (actinomycin D), adriamycin, daunorubicin, doxorubicin, bleomycin, plicamycin (mithramycin), mitomycin (mitomycin C), Taxol, Taxotere, etc.); enzymes (e.g., L-Asparaginase); and biological response modifiers (e.g., interferon-; interleukin 2, etc.). Other chemotherapeutic agents include cis-diaminedichloroplatinum II (CDDP); Carboplatin; Anthracendione (e.g., Mitoxantrone); Hydroxyurea; Procarbazine (N-methylhydrazine); and adrenocortical suppressants (e.g., Mitotane, aminoglutethimide, etc.). Other chemotherapeutic agents include adrenocorticosteroids (e.g., Prednisone); progestins (e.g., Hydroxyprogesterone caproate; Medroxyprogesterone acetate, Megestrol acetate, etc.); estrogens (e.g, diethylstilbestrol; ethenyl estradiol. etc.); antiestrogens (e.g. Tamoxifen, etc.); androgens (e.g., testosterone propionate, Fluoxymesterone, etc.); antiandrogens (e.g., Flutamide); and gonadotropin-releasing hormone analogs (e.g., Leuprolide).

In terms of surgery, any surgical intervention may be practiced in combination with the present invention. In connection with radiotherapy, any mechanism for inducing DNA damage locally within tumor cells is contemplated, such as γ-irradiation, X-rays, UV-irradiation, microwaves and even electronic emissions and the like. The directed delivery of radioisotopes to tumor cells is also contemplated, and this may be used in connection with a targeting antibody or other targeting means.

Cytokine therapy also has proven to be an effective partner for combined therapeutic regimens. Various cytokines may be employed in such combined approaches. Examples of cytokines include IL-1α, IL-1β, IL-2, IL-3, IL-4, IL-5, IL-6, IL-7, IL-8, IL-9, IL-10, IL-11, IL-12, IL-13, TGF-β, GM-CSF, M-CSF, G-CSF, TNFα, TNFβ, LAF, TCGF, BCGF, TRF, BAF, BDG, MP, LIF, OSM, TMF, PDGF, IFN-α, IFN-β, IFN-γ. Cytokines are administered according to standard regimens, consistent with clinical indications such as the condition of the patient and relative toxicity of the cytokine. Uteroglobins may also be used to prevent or inhibit metastases (U.S. Pat. No. 5,696,092; incorporated herein by reference).

In one embodiment, the administration of fusion proteins of the present disclosure can be combined with the administration of anti CTLA4 or Anti PDL1.

In another preferred embodiment, the fusion molecules described herein can also be administered in combination with one or more anti-angiogenic factors. A wide variety of other anti-angiogenic factors may also be utilized within the context of the present invention. Representative examples include Platelet Factor 4 (Sigma Chemical Co., #F1385); Protamine Sulphate (Clupeine) (Sigma Chemical Co., #P4505); Sulfated Chitin Derivatives (prepared from queen crab shells), (Sigma Chemical Co., #C3641; Murata et al. *Cancer Res.* 51:22-26, 1991); Sulfated Polysaccharide Peptidoglycan Complex (SP-PG) (the function of this compound may be enhanced by the presence of steroids such as estrogen, and tamoxifen citrate); Staurosporine (Sigma Chemical Co., #S4400); Modulators of Matrix Metabolism, including for example, proline analogs {[(L-azetidine-2-carboxylic acid (LACA) (Sigma Chemical Co., #A0760)), cishydroxyproline, d,L-3,4-dehydroproline (Sigma Chemical Co., #D0265), Thiaproline (Sigma Chemical Co., #T0631)], α,α-dipyridyl (Sigma Chemical Co., #D7505), β-aminopropionitrile fumarate (Sigma Chemical Co., #A3134)]}; MDL 27032 (4-propyl-5-(4-pyridinyl)-2(3H)-oxazolone; Merion Merrel Dow Research Institute); Methotrexate (Sigma Chemical Co., #A6770; Hirata et al. *Arthritis and Rheumatism* 32:1065-1073, 1989); Mitoxantrone (Polyerini and Novak, *Biochem. Biophys. Res. Comm.* 140:901-907); Heparin (Folkman, *Bio. Phar.* 34:905-909, 1985; Sigma Chemical Co., #P8754); Interferons (e.g., Sigma Chemical Co., #13265); 2 Macroglobulin-serum (Sigma Chemical Co., #M7151); ChIMP-3 (Payloff et al., *J. Bio. Chem.* 267:17321-17326, 1992); Chymostatin (Sigma Chemical Co., #C7268; Tomkinson et al. *Biochem J.* 286: 475-480, 1992); β-Cyclodextrin Tetradecasulfate (Sigma Chemical Co., #C4767); Eponemycin; Camptothecin; Fumagillin (Sigma Chemical Co., #F6771; Canadian Patent No. 2,024,306; Ingber et al. *Nature* 348:555-557, 1990); Gold Sodium Thiomalate ("GST"; Sigma:G4022; Matsubara and Ziff, *J. Clin. Invest.* 79:1440-1446, 1987); (D-Penicillamine ("CDPT"; Sigma Chemical Co., #P4875 or P5000(HCl)); β-1-anticollagenase-serum; α2-antiplasmin (Sigma Chem. Co.: A0914; Holmes et al. *J. Biol. Chem.* 262(4):1659-1664, 1987); Bisantrene (National Cancer Institute); Lobenzarit disodium (N-(2)-carboxyphenyl-4-chloroanthronilic acid disodium or "CCA"; Takeuchi et al. *Agents Actions* 36:312-316, 1992); Thalidomide; Angostatic steroid; AGM-1470; carboxynaminolmidazole; metalloproteinase inhibitors such as BB94.

Although the above anti-angiogenic factors have been provided for the purposes of illustration, it should be understood that the present invention is not so limited. In particular, although certain anti-angiogenic factors are specifically referred to above, the present invention should be understood to include analogues, derivatives and conjugates of such anti-angiogenic factors. For example, paclitaxel should be understood to refer to not only the common chemically available form of paclitaxel, but analogues (e.g., taxotere, as noted above) and paclitaxel conjugates (e.g., paclitaxel-PEG, paclitaxel-dextran, or paclitaxel-xylos). In another preferred embodiment, the fusion molecules of the invention can also be targeted for treating angiogenesis-associated diseases. The term "angiogenesis-associated disease" is used herein, for purposes of the specification and claims, to mean certain pathological processes in humans where angiogenesis is abnormally enhanced/prolonged. Such angiogenesis-associated diseases include diabetic retinopathy, chronic inflammatory diseases, rheumatoid arthritis, dermatitis, psoriasis, stomach ulcers, and most types of human solid tumors.

Mutant Anti-Angiogenic Agents:

The anti-angiogenic agent can be an intact molecule, a functional fragment of the agent, or a naturally occurring or man-made mutant of the agent. For example, endostatin domains useful in the invention include any molecule derived from a native endostatin that shares a functional activity of endostatin, e.g., the ability to inhibit VEGF production or new vessel formation. The endostatin domain can be a native endostatin or a fragment of a native endostatin that retains a functional activity of a native endostatin. The endostatin domain can also be a non-naturally occurring form of endostatin (e.g., a mutant form created by amino acid substitution) that retains a functional activity of a native endostatin. A preferred embodiment is a mutant endostatin which has an amino acid change at position 125. The mutant endostatin molecules comprising the fusion molecule of the invention comprises natural, non-natural, modified, derived amino acids etc.

Thus, the definition of the term "endostatin" includes modifications or mutations of the protein, its subunits and peptide fragments. Such mutations include substitutions of naturally occurring amino acids at specific sites with other molecules, including but not limited to naturally and non-naturally occurring amino acids. Such substitutions may modify the bioactivity of the anti-angiogenic protein and produce biological or pharmacological agonists or antagonists. Modifications can also include modified amino acids within the protein sequence, or modifications to the intact protein sequence that inhibit protease activity, or otherwise enhance the stability of the protein and decrease protein degradation. Such modifications are well-known to those of skill in the art.

Modified proteins are also referred to herein as derivative proteins, or analogs. The term "derivative" or "analog" includes any protein/polypeptide having an amino acid residue sequence substantially identical to a sequence specifically shown herein in which one or more residues have been conservatively substituted with a functionally similar residue and which displays the activity as described herein. Examples of conservative substitutions include the substitution of one non-polar (hydrophobic) residue such as isoleucine, valine, leucine or methionine for another, the substitution of one polar (hydrophilic) residue for another such as between arginine and lysine, between glutamine and asparagine, between threonine and serine, the substitution of one basic residue such as lysine, arginine or histidine for another, or the substitution of one acidic residue, such as aspartic acid or glutamic acid for another.

The phrase "conservative substitution" also includes the use of a chemically derivatized residue in place of a non-derivatized residue provided that such polypeptide displays the requisite inhibition activity.

"Chemical derivative" refers to a subject polypeptide having one or more residues chemically derivatized by reaction of a functional side group. Such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-imbenzylhistidine. Also included as chemical derivatives are those peptides which contain one or more naturally occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine. Polypeptides of the present invention also include any polypeptide having one or more additions and/or deletions of residues relative to the sequence of a polypeptide whose sequence is shown herein, so long as the requisite activity is maintained.

The present invention also contemplates amino acid residue sequences that are analogous to sequences of the proteins described herein, and the nucleic acid sequences encoding these proteins. It is well known in the art that modifications and changes can be made without substantially altering the biological function of the protein. In making such changes, substitutions of like amino acid residues can be made on the basis of relative similarity of side-chain substituents, for example, their size, charge, hydrophobicity, hydrophilicity and the like. Alterations of the type described may be made to enhance the peptide's potency or stability to enzymatic breakdown or pharmacokinetics. Thus, sequences deemed as within the scope of the invention, include those analogous sequences characterized by a change in amino acid residue sequence or type wherein the change does not alter the fundamental nature and biological activity of the aforementioned anti-angiogenic proteins, derivatives, mutants fragments and/or fusion proteins.

It will be appreciated that the term "endostatin" includes shortened proteins or peptides, referred to herein as fragments, wherein one or more amino acid is removed from either or both ends of endostatin, or from an internal region of the protein, yet the resulting molecule retains endothelial proliferation inhibiting activity. The term "endostatin" also includes lengthened proteins or peptides wherein one or more amino acid is added to either or both ends of endostatin, or to an internal location in the protein, yet the resulting molecule retains endothelial proliferation inhibiting activity. Such molecules, for example with tyrosine added in the first position are useful for labeling such as radioiodination with 125-iodine ($^{125}$I) for use in assays. Labeling with other radioisotopes may be useful in providing a molecular tool for destroying the target cell containing endostatin receptors. Other labeling with molecules such as ricin may provide a mechanism for destroying cells with anti-angiogenic protein receptors.

Anti-angiogenic fusion proteins of the present invention encompass a protein comprising one or more of the proteins, mutants, derivatives or fragments described herein as well as other anti-angiogenic molecules known to those of skill in the art. For example, a fusion protein encompassed by the present invention can be encoded by a polynucleotide encoding endostatin linked to another endostatin or endostatin mutant wherein the expressed fusion protein comprises activity of both endostatin and endostatin mutant, resulting in a reasonable increase of the biological activity of the fusion protein over either monomeric wild-type endostatin or endostatin mutant. Another type of fusion protein encompassed by the present invention can be a fusion protein encoded by a polynucleotide encoding two endostatin molecules in tandem, endostatin mutants or combinations thereof optionally linked by a linker. Again, it is reasonable to predict that the fusion protein would have higher activity than the monomeric endostatin.

Other examples of anti-angiogenic fusion proteins of the present invention include conjugates of the proteins. Such fusion proteins may or may not be capable of being cleaved into the separate proteins from which they are derived. As used herein, the term "conjugate of an anti-angiogenic protein" means an anti-angiogenic protein chemically coupled to another protein to form a conjugate. Examples of conjugates include a protein fragment coupled to albumin or to a peptide fragment from another anti-angiogenic protein.

As used herein, the term "anti-angiogenesis activity" refers to the capability of a molecule to inhibit the growth of blood vessels. As used herein, the term "endothelial inhibiting activity" refers to the capability of a molecule to inhibit angiogenesis in general and, for example, to inhibit the growth or migration of bovine capillary endothelial cells in culture in the presence of fibroblast growth factor or other known growth factors. An anti-angiogenic protein, mutant, derivative, fragment or fusion protein of the present invention may be characterized on the basis of potency when tested for its "endothelial inhibiting activity". Other measures of endothelial inhibiting activity are described herein.

The anti-angiogenic proteins of the present invention are effective in treating diseases or processes that are mediated by, or involve, angiogenesis. The present invention includes the method of treating an angiogenesis-mediated disease with an effective amount of an anti-angiogenic fusion protein produced by the methods described herein, or a biologically active mutant, derivative, fragment or fusion protein thereof, or combinations of proteins that collectively possess anti-angiogenic activity, or the activity of anti-angiogenic agonists and antagonists.

As used herein, the term "angiogenesis" means the generation of new blood vessels into a tissue or organ, and involves endothelial cell proliferation. Under normal physiological conditions, mammals (humans or animals) undergo angiogenesis only in very specific restricted situations. For example, angiogenesis is normally observed in wound healing, fetal and embryonal development, and formation of the corpus luteum, endometrium and placenta. The term "endothelium" means a thin layer of flat epithelial cells that lines serous cavities, lymph vessels, and blood vessels.

As used herein, the term "angiogenesis-associated factor" means a factor which either inhibits or promotes angiogenesis. An example of an angiogenesis-associated factor is an angiogenic growth factor, such as basic fibroblastic growth factor (bFGF), which is an angiogenesis promoter. Another example of an angiogenesis associated factor is an angiogenesis inhibiting factor such as angiostatin.

As used herein, the term "growth factor" means a molecule that stimulates the growth, reproduction, or synthetic activity of cells.

The angiogenesis mediated diseases include, encompassed herein but are not limited to, solid tumors; blood born tumors such as leukemias; tumor metastasis; benign tumors, for example hemangiomas, acoustic neuromas, neurofibromas, trachomas, and pyogenic granulomas; rheumatoid arthritis; psoriasis; ocular angiogenic diseases, for example, diabetic retinopathy, retinopathy of prematurity, macular degeneration, corneal graft rejection, neovascular glaucoma, retrolental fibroplasia, rubeosis; Osler-Webber Syndrome; myocardial angiogenesis; plaque neovascularization; telangiectasia; hemophiliac joints; angiofibroma; and wound granulation, intestinal adhesions, Crohn's disease, atherosclerosis, scleroderma, and hypertrophic scars, i.e., keloids. The anti-angiogenic proteins described herein can also be used as a birth control agent by preventing vascularization required for embryo implantation. The proteins are also useful in the treatment of diseases that have angiogenesis as a pathologic consequence such as cat scratch disease (*Rochele minalia quintosa*) and ulcers (*Helicobacter pylori*).

Radiolabeling:

In another preferred embodiment, the fusion molecule of the invention can be radiolabeled. Uses include therapeutic and imaging for diagnostic purposes. The label may be a radioactive atom, an enzyme, or a chromophore moiety. Methods for labeling antibodies have been described, for example, by Hunter and Greenwood, *Nature,* 144:945 (1962) and by David et al. *Biochemistry* 13:1014-1021 (1974). Additional methods for labeling antibodies have been described in U.S. Pat. Nos. 3,940,475 and 3,645,090. Methods for labeling oligonucleotide probes have been described, for example, by Leary et al. *Proc. Natl. Acad. Sci. USA* (1983) 80:4045; Renz and Kurz, *Nucl. Acids Res.* (1984) 12:3435; Richardson and Gumport, *Nucl. Acids Res.* (1983) 11:6167; Smith et al. *Nucl. Acids Res.* (1985) 13:2399; and Meinkoth and Wahl, *Anal. Biochem.* (1984) 138:267.

The label may be radioactive. Some examples of useful radioactive labels include $^{32}$I, $^{125}$I, $^{131}$I, and $^{3}$H. Use of radioactive labels have been described in U.K. 2,034,323, U.S. Pat. No. 4,358,535, and U.S. Pat. No. 4,302,204.

Some examples of non-radioactive labels include enzymes, chromophores, atoms and molecules detectable by electron microscopy, and metal ions detectable by their magnetic properties.

Some useful enzymatic labels include enzymes that cause a detectable change in a substrate. Some useful enzymes and their substrates include, for example, horseradish peroxidase (pyrogallol and o-phenylenediamine), β-galactosidase (fluorescein β-D-galactopyranoside), and alkaline phosphatase (5-bromo-4-chloro-3-indolyl phosphate/nitro blue tetrazolium). The use of enzymatic labels has been described in U.K. 2,019,404, EP 63,879, and by Rotman, Proc. Natl. Acad. Sci. USA, 47, 1981-1991 (1961).

Useful chromophores include, for example, fluorescent, chemiluminescent, and bioluminescent molecules, as well as dyes. Some specific chromophores useful in the present invention include, for example, fluorescein, rhodamine, Texas red, phycoerythrin, umbelliferone, luminol.

The labels may be conjugated to the antibody or nucleotide probe by methods that are well known in the art. The labels may be directly attached through a functional group on the probe. The probe either contains or can be caused to contain such a functional group. Some examples of suitable functional groups include, for example, amino, carboxyl, sulfhydryl, maleimide, isocyanate, isothiocyanate. Alternatively, labels such as enzymes and chromophores may be conjugated to the antibodies or nucleotides by means of coupling agents, such as dialdehydes, carbodiimides, dimaleimides, and the like.

The label may also be conjugated to the probe by means of a ligand attached to the probe by a method described above and a receptor for that ligand attached to the label. Any of the known ligand-receptor combinations is suitable. Some suitable ligand-receptor pairs include, for example, biotin-avidin or biotin-streptavidin, and antibody-antigen.

In another preferred embodiment, the chimeric fusion molecules of the invention can be used for imaging. In imaging uses, the complexes are labeled so that they can be detected outside the body. Typical labels are radioisotopes, usually ones with short half-lives. The usual imaging radioisotopes, such as $^{123}$I, $^{124}$I, $^{125}$I, $^{131}$I, $^{99m}$TC, $^{186}$Re, $^{188}$Re, $^{64}$Cu, $^{67}$Cu, $^{212}$Bi, $^{213}$Bi, $^{67}$Ga, $^{90}$Y, $^{111}$In, $^{18}$F, $^{3}$H, $^{14}$C, $^{35}$S or $^{32}$P can be used. Nuclear magnetic resonance (NMR) imaging enhancers, such as gadolinium-153, can also be used to label the complex for detection by NMR. Methods and reagents for performing the labeling, either in the polynucleotide or in the protein moiety, are considered known in the art.

Domain Molecules

As described supra, the invention provides chimeric molecules that include both an anti-angiogenic agent domain and carrier domain. The anti-angiogenic agent domain reduces tumor growth (e.g., by inhibiting angiogenesis), while the carrier domain confers a functional attribute to the chimeric molecule. For instance, where the carrier domain is an Ig domain, it can function to target the chimeric molecule to a particular site (e.g., the antigen-binding portion of the antibody binds to an antigen expressed by a target cell and/or the Fc portion of the Ig domain can target the chimeric molecule to an Fc receptor-bearing cell); to increase stability of the chimeric molecule (e.g., for in vitro storage or in vivo delivery); to impart an effector function to the chimeric molecule (e.g., immune response-stimulating, cytotoxicity, etc.); or to facilitate purification of the chimeric molecule.

The carrier domain can be any substance that imparts a function to the chimeric molecule. For example, a carrier domain can be a molecule that increases the stability of the chimeric molecule (e.g., for in vitro storage or in vivo delivery); introduces an effector function to the chimeric molecule (e.g., immune response-stimulating, cytotoxicity, etc.); or facilitates purification of the chimeric molecule. For increasing the stability of the chimeric molecule, the carrier domain can be a protein that has been shown to stabilize molecules in an in vitro storage or in vivo delivery setting. For example, carrier domains for increasing the stability of the chimeric molecule include one or more domains from an Ig molecule (e.g., a $CH_2$—$CH_3$ fragment). Other carrier domains that can be used to stabilize the chimeric molecule can be identified empirically. For instance, a molecule can be screened for suitability as a carrier domain by conjugating the molecule to anti-angiogenic agent and testing the conjugated product in in vitro or in vivo stability assays.

In another preferred embodiment, carrier domains within the invention facilitate purification of the chimeric molecule. Any molecule known to facilitate purification of a chimeric molecule can be used. Representative examples of such carrier domains include antibody fragments and affinity tags (e.g., GST, HIS, FLAG, and HA). Chimeric molecules containing an affinity tag can be purified using immunoaffinity techniques (e.g., agarose affinity gels, glutathione-agarose beads, antibodies, and nickel column chromatography). Chimeric molecules that contain an Ig domain as a carrier domain can be purified using immunoaffinity chromatography techniques known in the art (e.g., protein A or protein G chromatography).

Other carrier domains within the invention that can be used to purify the chimeric molecule can be readily identified by testing the molecules in a functional assay. For instance, a molecule can be screened for suitability as a carrier domain by fusing the molecule to an anti-angiogenic agent and testing the fusion for purity and yield in an in vitro assay. The purity of recombinant proteins can be estimated by conventional techniques, for example, SDS-PAGE followed by the staining of gels with Coomassie-Blue.

A number of other carrier domains can be used to impart an effector function to the chimeric molecule. These include other cytotoxins, drugs, detectable labels, targeting ligands, and delivery vehicles. Examples of these are described in U.S. Pat. No. 6,518,061 and U.S. published patent application number 20020159972.

A preferred carrier domain for use in the chimeric molecule is an Ig or portion of an Ig. The Ig domain may take the form of a single chain antibody (e.g., a scFV), an Fab fragment, an F(ab')$_2$ fragment, an Ig heavy chain, or an Ig in which one or more of the constant regions has been removed. The Ig domain can be derived from any Ig class including IgG, IgM, IgE, IgA, IgD and any subclass thereof. In some applications, it is preferred that the Ig domain includes a large hinge region, e.g., one from IgG3.

In another preferred embodiment, the Ig domain is a minibody. A small protein scaffold called a "minibody" was designed using a part of the Ig VH domain as the template (Pessi et al., *Nature*, 362:367-69 (1993)). Minibodies with high affinity (dissociation constant ($K_d$) about $10^{-7}$ M) to interleukin-6 were identified by randomizing loops corresponding to CDR1 and CDR2 of VH and then selecting mutants using the phage display method (Martin et al., *EMBO J.* 1994 Nov. 15; 13(22): 5303-5309). These experiments demonstrated that the essence of the antibody function could be transferred to a smaller system. Thus, the chimeric fusion molecule may comprise a minibody Ig domain.

Chimeric molecules can be prepared using conventional techniques in molecular biology or protein chemistry. Where the chimeric molecule is a fusion protein, molecular biology methods can be used to join two or more genes in frame into a single nucleic acid. The nucleic acid can then be expressed in an appropriate host cell under conditions in which the chimeric molecule is produced. A carrier domain might also be conjugated (e.g., covalently bonded) to an anti-angiogenic agent domain by other methods known in the art for conjugating two such molecules together. For example, the anti-angiogenic agent domain can be chemically derivatized with a carrier domain either directly or using a linker (spacer). Several methods and reagents (e.g., cross-linkers) for mediating this conjugation are known. See, e.g., catalog of Pierce Chemical Company; and Means and Feeney, Chemical Modification of Proteins, Holden-Day Inc., San Francisco, Calif. 1971; "Monoclonal Antibody-Toxin Conjugates: Aiming the Magic Bullet," Thorpe et al., Monoclonal Antibodies in Clinical Medicine, Academic Press, pp. 168-190 (1982); Waldmann (1991) Science, 252: 1657; and U.S. Pat. Nos. 4,545,985 and 4,894,443.

An anti-angiogenic agent may be fused or conjugated to a carrier domain in various orientations. For example, the carrier domain may be joined to either the amino or carboxy termini of an anti-angiogenic agent domain. The anti-angiogenic agent domain may also be joined to an internal region of the carrier domain, or conversely, the carrier domain may be joined to an internal location of the anti-angiogenic agent domain.

In some circumstances, it is desirable to free the carrier domain from the anti-angiogenic agent domain when the chimeric molecule has reached its target site. Therefore, chimeric conjugates featuring linkages that are cleavable in the vicinity of the target site may be used when one of the domains is to be released at the target site. Cleaving of the linkage to release the carrier domain from the anti-angiogenic agent domain may be prompted by enzymatic activity or conditions to which the conjugate is subjected either inside the target cell or in the vicinity of the target site. When the target site is a tumor, a linker which is cleavable under conditions present at the tumor site (e.g. when exposed to tumor-associated enzymes or acidic pH) may be used. A number of different cleavable linkers are known to those of skill in the art. See, e.g., U.S. Pat. Nos. 4,618,492; 4,542,225; and 4,625,014. The mechanisms for release of an agent from these linker groups include, for example, irradiation of a photolabile bond and acid-catalyzed hydrolysis. U.S. Pat. No. 4,671,958, for example, includes a description of immunoconjugates comprising linkers which are cleaved at the target site in vivo by the proteolytic enzymes of the patient's complement system. In view of the large number of methods that have been reported for attaching a variety of radiodiagnostic compounds, radiotherapeutic compounds, drugs, toxins, and other agents to proteins one skilled in the art will be able to determine a suitable method for attaching a given carrier domain to an anti-angiogenic agent domain.

Bispecific Chimeric Molecules

In another preferred embodiment, chimeric molecules comprising a modulatory or cytolytic domain is fused to a bispecific antibody domain or fragments thereof. In one aspect of the invention, the bispecific antibody comprises two monoclonal antibodies. However, the bispecific antibody can comprise two polyclonal antibodies or an engineered bispecific antibody.

Preferably, each of the specificities of the bispecific antibody are directed to one or more tumor antigens and/or specific cell or tissue. Antibodies can be raised against any tumor antigen from a patient. Thus the targeting of the chimeric molecule can be individually tailored as the tumor displays different antigens.

Bispecific antibodies may be constructed by hybrid-hybridoma techniques, by covalently linking specific antibodies or by other approaches, like the diabody approach (Kipriyanow et al., *Int. J. Cancer* 77 (1998), 763-773). In one aspect of the invention, the bispecific antibody is a single chain antibody construct.

For tracking purposes, the bispecific antibody can be directly labeled or a second antibody specific for a region of the bispecific antibody is labeled. Detection of the localization of the chimeric molecule is preferably through cell sorting techniques such as flow cytometry. For example, wherein samples are taken at different time intervals after administration of the chimeric molecule for imaging and diagnostic purposes.

In accordance with the invention, the bispecific antibody, targets chimeric molecules to a specific location in vivo. For example, the location can be to myocardial tissues, breast, liver, spleen, ovaries, testis, hepatocyte, kidneys and the like. The bispecific antibody determines the specific antigen to which the chimeric molecule is targeted.

As described above, the specificity of the antibody domain can be directed to a specific tissue antigen wherein the tumor has been detected coupled with specificity for that particular tumor antigen. Alternatively, the bispecific antibody domain is directed to two tumor antigens that are expressed by the tumor. The bispecific domain can be fused to any modulatory or cytolytic domain discussed above.

In another embodiment of the invention, the bispecific antibody (BiAb) construct is a bispecific antibody that binds to one or more tumor antigens as a first or second antigen and a cell or tissue specific antigen as a second antigen. The antibody may be covalently bound to the a modulatory or cytolytic molecule and the chimeric molecule may be constructed by chemical coupling, producing a fusion protein or a mosaic protein from the antibody and from a modified or unmodified prokaryotic or eukaryotic modulatory or cytotoxic molecule. Furthermore, the antibody may be joined to modulatory or cytotoxic molecule via multimerization domains.

In another embodiment of the invention, the chimeric polypeptide of the invention, e.g., a endostatin construct, is a fusion construct of a modified or an unmodified endostatin with a modified or an unmodified modulatory or cytotoxic molecule. The construct may be bound in vitro and/or in vivo, e.g., by a multimerization domain, to bispecific antibody domain. The chimeric molecule constructs may, inter alia, result from chemical coupling, may be recombinantly produced, or may be produced as a fusion protein as described above. In one aspect, the moiety specifically binds to at least one tumor antigen.

The compositions of the invention can comprise any cytotoxic agent as described infra. For example, in one aspect, the toxin may be a polypeptide toxin, e.g., a *Pseudomonas* exotoxin, like PE38, PE40 or PE37, or a truncated version thereof, or a ribosome inactivating protein gelonin (e.g., Boyle (1996) *J. Immunol.* 18:221-230), and the like. The compositions of the invention can be conjugated to any cytotoxic pharmaceuticals, e.g., radiolabeled with a cytotoxic agents, such as, e.g., 0.1311 (e.g., Shen (1997) *Cancer* 80(12 Suppl.): 2553-2557), copper-67 (e.g., Deshpande (1988) *J. Nucl. Med.* 29:217-225).

In one embodiment, the chimeric molecule construct is a fusion (poly)peptide or a mosaic (poly)peptide. The fusion (poly)peptide may comprise merely the domains of the constructs as described herein, as well as (a) functional fragment(s) thereof. However, it is also envisaged that the fusion (poly)peptide comprises further domains and/or functional stretches. Therefore, the fusion (poly)peptide can comprise at least one further domain, this domain being linked by covalent or non-covalent bonds. The linkage as well as the construction of such constructs, can be based on genetic fusion according to the methods described herein or known in the art (e.g., Sambrook et al., loc. cit., Ausubel, "Current Protocols in Molecular Biology", Green Publishing Associates and Wiley Interscience, N.Y. (1989)) or can be performed by, e.g., chemical cross-linking as described in, e.g., WO 94/04686. The additional domain present in the construct may be linked by a flexible linker, such as a (poly)peptide linker, wherein the (poly)peptide linker can comprises plural, hydrophilic, peptide-bonded amino acids of a length sufficient to span the distance between the C-terminal end of the further domain and the N-terminal end of the peptide, (poly)peptide or antibody or vice versa. The linker may, inter alia, be a Glycine, a Serine and/or a Glycine/Serine linker. Additional linkers comprise oligomerization domains. Oligomerization domains can facilitate the combination of two or several antigens or fragments thereof in one functional molecule. Non-limiting examples of oligomerization domains comprise leucine zippers (like jun-fos, GCN4, E/EBP; Kostelny, *J. Immunol.* 148 (1992), 1547-1553; Zeng, *Proc. Natl. Acad. Sci.* USA 94 (1997), 3673-3678, Williams, *Genes Dev.* 5 (1991), 1553-1563; Suter, "Phage Display of Peptides and Proteins", Chapter 11, (1996), Academic Press), antibody-derived oligomerization domains, like constant domains $C_H1$ and $C_L$ (Mueller, *FEBS Letters* 422 (1998), 259-264) and/or tetramerization domains like $GCN_4$-LI (Zerangue, *Proc. Natl. Acad. Sci.* USA 97 (2000), 3591-3595).

In another preferred embodiment, the linker comprises integrin motifs such as for example, one or more of NGR motifs (Asn-Gly-Arg) and/or RGD (Arg-Gly-Asp) and combinations thereof. Furthermore, the chimeric fusion construct to be used in the present invention, as described herein, may comprise at least one further domain, inter alia, domains which provide for purification means, like, e.g. histidine stretches. The further domain(s) may be linked by covalent or non-covalent bonds.

The linkage can be based on genetic fusion according to the methods known in the art and described herein or can be performed by, e.g., chemical cross-linking as described in, e.g., WO 94/04686. The additional domain present in the construct may be linked by a flexible linker, such as a polypeptide linker to one of the binding site domains; the polypeptide linker can comprise plural, hydrophilic or peptide-bonded amino acids of a length sufficient to span the distance between the C-terminal end of one of the domains and the N-terminal end of the other of the domains when the polypeptide assumes a conformation suitable for binding when disposed in aqueous solution.

Immune Activating Chimeric Fusion Molecules

It is also envisaged that the constructs disclosed for uses, compositions and methods of the present invention comprises (a) further domain(s) which may function as immunomodulators. The immunomodulators comprise, but are not limited to cytokines, lymphokines, T cell co-stimulatory ligands, etc. Preferably, the chimeric fusion molecule targets and delivers a modulatory or cytolytic molecule to the tumor cell and also recruits immune cells and/or activated immune cells to the tumor.

Adequate activation resulting in priming of naïve T-cells is critical to primary immune responses and depends on two signals derived from professional APCs (antigen-presenting cells) like dendritic cells. The first signal is antigen-specific and normally mediated by stimulation of the clonotypic T-cell antigen receptor (TCR) that is induced by processed antigen presented in the context of MHC class-I or MHC class-II molecules. However, this primary stimulus is insufficient to induce priming responses of naïve T-cells, and the second signal is required which is provided by an interaction of specific T-cell surface molecules binding to co-stimulatory ligand molecules on antigen presenting cells (APCs), further supporting the proliferation of primed T-cells. The term "T-cell co-stimulatory ligand" therefore denotes in the light of the present invention molecules, which are able to support priming of naïve T-cells in combination with the primary stimulus and include, but are not limited to, members of the B7 family of proteins, including B7-1 (CD80) and B7-2 (CD86), 4-1BB ligand, CD40 ligand, OX40 ligand.

The chimeric fusion molecule construct described herein may comprise further receptor or ligand function(s), and may comprise immune-modulating effector molecule or a fragment thereof. An immune-modulating effector molecule positively and/or negatively influences the humoral and/or cellular immune system, particularly its cellular and/or non-cellular components, its functions, and/or its interactions with other physiological systems. The immune-modulating effector molecule may be selected from the group comprising cytokines, chemokines, macrophage migration inhibitory factor (MIF; as described, in Bernhagen (1998), *Mol Med* 76(3-4); 151-61 or Metz (1997), *Adv Immunol* 66, 197-223), T-cell receptors and soluble MHC molecules. Such immune-modulating effector molecules are well known in the art and are described, inter alia, in Paul, "Fundamental immunology", Raven Press, New York (1989). In particular, known cytokines and chemokines are described in Meager, "The Molecular Biology of Cytokines" (1998), John Wiley & Sons, Ltd., Chichester, West Sussex, England; (Bacon (1998). Cytokine Growth Factor Rev 9(2): 167-73; Oppenheim (1997). *Clin Cancer Res* 12, 2682-6; Taub, (1994) *Ther. Immunol.* 1(4), 229-46 or Michiel, (1992). *Semin Cancer Biol* 3(1), 3-15).

Immune cell activity that may be measured include, but is not limited to: (1) cell proliferation by measuring the DNA replication; (2) enhanced cytokine production, including specific measurements for cytokines, such as IFN-γ, GM-CSF, or TNF-α; (3) cell mediated target killing or lysis; (4) cell differentiation; (5) immunoglobulin production; (6) phenotypic changes; (7) production of chemotactic factors or chemotaxis, meaning the ability to respond to a chemotactin with chemotaxis; (8) immunosuppression, by inhibition of the activity of some other immune cell type; and, (9) apoptosis, which refers to fragmentation of activated immune cells under certain circumstances, as an indication of abnormal activation.

Modified Chimeric Molecules

The constructs of the present invention may comprise domains originating from one species, e.g., from mammals, such as human. However, chimeric and/or human and/or humanized constructs are also envisaged and within the scope of the present invention.

Furthermore, the polynucleotide/nucleic acid molecules of the invention may comprise, for example, thioester bonds and/or nucleotide analogues. The modifications may be useful for the stabilization of the nucleic acid molecule, e.g., against endo- and/or exonucleases in the cell. These nucleic acid molecules may be transcribed by an appropriate vector containing a chimeric gene which allows for the transcription of the nucleic acid molecule in the cell. The polynucleotide/nucleic acid molecules of the invention may be a recombinantly produced chimeric nucleic acid molecule comprising any of the aforementioned nucleic acid molecules either alone or in combination. The polynucleotide may be, e.g., DNA, cDNA, RNA or synthetically produced DNA or RNA or a recombinantly produced chimeric nucleic acid molecule comprising any of those polynucleotides either alone or in combination. The polynucleotide can be part of a vector, e.g., an expression vector, including, e.g., recombinant viruses. The vectors may comprise further genes, such as marker genes, that allow for the selection of the vector in a suitable host cell and under suitable conditions.

In one aspect, the polynucleotides of the invention are operatively linked to expression control sequences allowing expression in prokaryotic or eukaryotic cells. Expression of the polynucleotide comprises transcription of the polynucleotide into a translatable mRNA. Regulatory elements ensuring expression in cells, including eukaryotic cells, such as mammalian cells, are well known to those skilled in the art. They usually comprise regulatory sequences ensuring initiation of transcription, and, optionally, poly-A signals ensuring termination of transcription and stabilization of the transcript. Additional regulatory elements may include transcriptional as well as translational enhancers, and/or naturally-associated or heterologous promoter regions. Exemplary regulatory elements permitting expression in prokaryotic host cells comprise, e.g., the PL, lac, trp or tac promoter in *E. coli*, and examples for regulatory elements permitting expression in eukaryotic host cells are the AOX1 or GAL1 promoter in yeast or the CMV-, SV40-, RSV-promoter (Rous sarcoma virus), CMV-enhancer, SV40-enhancer or a globin intron in mammalian and other animal cells. The nucleic acids of the invention can also comprise, in addition to elements responsible for the initiation of transcription, other elements, such regulatory elements and transcription termination signals, such as the SV40-poly-A site or the tk-poly-A site (termination sequences are typically downstream of the polynucleotide coding sequence). Furthermore, depending on the expression system used, nucleic acid sequences encoding leader sequences capable of directing the polypeptide to a cellular compartment, or secreting it into the medium, may be added to the coding sequence of the polynucleotide of the invention; such leader sequences are well known in the art. The leader sequence(s) is (are) assembled in appropriate phase with translation, initiation and termination sequences. In one aspect, the leader sequence is capable of directing secretion of translated chimeric protein, or a portion thereof, into the periplasmic space or extracellular medium. Optionally, the heterologous sequence can encode a fusion protein including an N-terminal identification peptide imparting desired characteristics, e.g., stabilization or simplified purification of expressed recombinant product; see supra. In this context, suitable expression vectors are known in the art such as Okayama-Berg cDNA expression vector pcDV1 (Pharmacia), pCDM8, pRc/CMV, pcDNA1, pcDNA3 (Invitrogen), or pSPORT1 (GIBCO BRL). Expression control sequences can be eukaryotic promoter systems in vectors capable of transforming or transfecting eukaryotic host cells; control sequences for prokaryotic hosts may also be used. Once the vector has been incorporated into the appropriate host, the host can be maintained under conditions suitable for high level expression of the nucleotide sequences; and, as desired, the collection and purification of the polypeptide of the invention may follow.

As described above, the polynucleotide of the invention can be used alone or as part of a vector (e.g., an expression vector or a recombinant virus), or in cells, to express the chimeric fusion molecules of the invention. The polynucleotides or vectors containing the DNA sequence(s) encoding any one of the chimeric fusion molecules of the invention can be introduced into the cells, which in turn produce the polypeptide of interest.

The present invention is directed to vectors, e.g., plasmids, cosmids, viruses and bacteriophages, or any expression system used conventionally in genetic engineering, that comprise a polynucleotide encoding a chimeric fusion molecule of the invention. The vector can be an expression vector and/or a gene transfer or targeting vector. Expression vectors derived from viruses such as retroviruses, vaccinia virus, adeno-associated virus, herpes viruses, or bovine papilloma virus, may be used for delivery of the polynucleotides or vectors of the invention into targeted cell populations. Methods which are well known to those skilled in the art can be used to construct recombinant vectors; see, for example, the techniques described in Sambrook, Molecular Cloning: A Laboratory Manual, Cold Spring Harbor Laboratory (1989) N.Y. and Ausubel, Current Protocols in Molecular Biology, Green Publishing Associates and Wiley Interscience, N.Y. (1989). Alternatively, the polynucleotides and vectors of the invention can be reconstituted into liposomes for delivery to target cells. The vectors containing the polynucleotides of the invention can be transferred into the host cell by well-known methods, which vary depending on the type of cellular host. For example, calcium chloride transfection is commonly utilized for prokaryotic cells, whereas calcium phosphate treatment or electroporation may be used for other cellular hosts; see Sambrook, supra.

Once expressed, the chimeric fusion molecules of the present invention can be purified according to standard procedures of the art, including ammonium sulfate precipitation, affinity columns, column chromatography, gel electrophoresis and the like; see, Scopes, "Protein Purification", Springer-Verlag, N.Y. (1982). In alternative aspects, the invention is directed to substantially pure chimeric polypeptides of at least about 90% to about 95% homogeneity; between about 95% to 98% homogeneity; and about 98% to about 99% or more homogeneity; these "substantially pure" polypeptides can be used in the preparation of pharmaceuticals. Once purified, partially or to a homogeneity as desired, the polypeptides may then be used therapeutically (including extracorporeally) or in developing and performing assay procedures.

In a still further embodiment, the present invention relates to a cell containing the polynucleotide or vector of the invention, or to a host cell transformed with a polynucleotide or vector of the invention. In alternative aspects, the host/cell is a eukaryotic cell, such as a mammalian cell, particularly if therapeutic uses of the polypeptide are envisaged. Of course, yeast and prokaryotic, e.g., bacterial cells, may serve as well, in particular, if the produced polypeptide is used for non-pharmaceutical purposes, e.g., as in diagnostic tests or kits or in screening methods.

The polynucleotide or vector of the invention that is present in the host cell may either be integrated into the genome of the host cell or it may be maintained extrachromosomally, e.g., as an episome.

The term "prokaryotic" is meant to include all bacteria that can be transformed or transfected with DNA or RNA molecules for the expression of a polypeptide of the invention. Prokaryotic hosts may include gram negative as well as gram positive bacteria such as, for example, *E. coli, S. typhimurium, Serratia marcescens* and *Bacillus subtilis*. The term "eukaryotic" is meant to include yeast, higher plant, insect and mammalian cells. Depending upon the host employed in a recombinant production procedure, the chimeric fusion molecules of the present invention may be glycosylated or may be non-glycosylated. Chimeric fusion molecules of the invention may also include an initial methionine amino acid residue. A polynucleotide coding for a polypeptide of the invention can be used to transform or transfect the host using any of the techniques commonly known to those of ordinary skill in the art.

In one aspect, the nucleic acids encoding the chimeric polypeptide of the invention (including those sequences in vectors, e.g., plasmid or virus) further comprise, genetically fused thereto, sequences encoding an epitope tag, e.g., an N-terminal FLAG-tag and/or a C-terminal His-tag. In one aspect, the length of the FLAG-tag is about 4 to 8 amino acids; or, is about 8 amino acids in length. Methods for preparing fused, operably linked genes and expressing them in, e.g., mammalian cells and bacteria are well-known in the art (Sambrook, Molecular Cloning: A Laboratory Manual, Cold Spring Harbor Laboratory, Cold Spring Harbor, N.Y., 1989). The genetic constructs and methods described therein can be utilized for expression of the polypeptide of the invention in eukaryotic or prokaryotic hosts. In general, expression vectors containing promoter sequences which facilitate the efficient transcription of the inserted polynucleotide are used in connection with the host. The expression vector typically contains an origin of replication, a promoter, and a terminator, as well as specific genes which are capable of providing phenotypic selection of the transformed cells. Furthermore, transgenic non-human animals, such as mammals (e.g., mice, goats), comprising nucleic acids or cells of the invention may be used for the large scale production of the chimeric polypeptides of the invention.

In a further embodiment, the invention is directed to a process for the preparation of a polypeptide of the invention comprising cultivating a (host) cell of the invention under conditions suitable for the expression of the chimeric fusion molecule construct and isolating the polypeptide from the cell or the culture medium. The transformed hosts can be grown in fermentors and cultured according to techniques known in the art to achieve optimal cell growth. The produced constructs of the invention can then be isolated from the growth medium, cellular lysates, or cellular membrane fractions. The isolation and purification of the expressed polypeptides of the invention (e.g., microbially expressed) may be by any conventional means such as, e.g., preparative chromatographic separations and immunological separations, such as those involving the use of monoclonal or polyclonal antibodies directed against, e.g., a tag of the polypeptide of the invention or as described in the appended examples.

Depending on the host cell, renaturation techniques may be required to attain proper conformation. If necessary, point substitutions seeking to optimize binding may be made in the DNA using conventional cassette mutagenesis or other protein engineering methodology such as is disclosed herein. Preparation of the polypeptides of the invention may also be dependent on knowledge of the amino acid sequence (or corresponding DNA or RNA sequence) of bioactive proteins such as enzymes, toxins, growth factors, cell differentiation factors, receptors, anti-metabolites, hormones or various cytokines or lymphokines. Such sequences are reported in the literature and available through computerized data banks. The present invention further relates to a chimeric polypeptide, encoded by a polynucleotide of the invention or produced by the method described hereinabove.

Additionally, the present invention provides for compositions comprising the polynucleotide, the vector, the host cell, and a chimeric fusion molecule, as described herein.

The term "composition", in context of this invention, comprises at least one polynucleotide, vector, host cell, chimeric polypeptide of the invention, as described herein. The composition, optionally, further comprises other molecules, either alone or in combination, such as molecules which are capable of modulating and/or interfering with the immune system. The composition may be in solid, liquid or gaseous form and may be, inter alia, in a form of a powder(s), a tablet(s), a solution(s) or an aerosol(s). In alternative embodiments, the composition comprises at least two, at least three, at least four, or more than four, compounds of the invention. The composition can be a pharmaceutical composition further comprising, optionally, a pharmaceutically acceptable carrier, diluent and/or excipient.

Humanized Antibodies

In a preferred embodiment, antibodies of the invention comprise human or humanized antibodies. Humanized antibodies are antibodies whose light and heavy chain genes have been constructed, typically by genetic engineering, from immunoglobulin variable and constant region genes belonging to different species. For example, the variable segments of the genes from a mouse monoclonal antibody may be joined to human constant segments, such as gamma 1 and gamma 3. A typical therapeutic chimeric antibody is thus a hybrid protein composed of the variable or antigen-binding domain from a mouse antibody and the constant or effector domain from a human antibody, although other mammalian species may be used.

As used herein, the term "humanized" immunoglobulin refers to an immunoglobulin comprising a human framework region and one or more CDR's from a non-human (usually a mouse or rat) immunoglobulin. The non-human immunoglobulin providing the CDR's is called the "donor" and the human immunoglobulin providing the framework is called the "acceptor." Constant regions need not be present, but if they are, they must be substantially identical to human immunoglobulin constant regions, i.e., at least about 85-90%, preferably about 95% or more identical. Hence, all parts of a humanized immunoglobulin, except possibly the CDR's, are substantially identical to corresponding parts of natural human immunoglobulin sequences. A "humanized antibody" is an antibody comprising a humanized light chain and a humanized heavy chain immunoglobulin, e.g., the entire variable region of a chimeric antibody is non-human. One says that the donor antibody has been "humanized", by the process of "humanization", because the resultant humanized antibody is expected to bind to the same antigen as the donor antibody that provides the CDR's.

It is understood that the humanized antibodies may have additional conservative amino acid substitutions which have substantially no effect on antigen binding or other immunoglobulin functions. By conservative substitutions are intended combinations such as Gly, Ala; Val, Ile, Leu; Asp, Glu; Asn, Gln; Ser, Thr; Lys, Arg; Phe, and Tyr.

Humanized immunoglobulins, including humanized antibodies, have been constructed by means of genetic engineering. Most humanized immunoglobulins that have been previously described have comprised a framework that is identical to the framework of a particular human immunoglobulin chain, the acceptor, and three CDR's from a non-human donor immunoglobulin chain.

A principle is that as an acceptor, a framework is used from a particular human immunoglobulin that is unusually homologous to the donor immunoglobulin to be humanized, or use a consensus framework from many human antibodies. For example, comparison of the sequence of a mouse heavy (or light) chain variable region against human heavy (or light) variable regions in a data bank (for example, the National Biomedical Research Foundation Protein Identification Resource) shows that the extent of homology to different human regions varies greatly, typically from about 40% to about 60-70%. By choosing as the acceptor immunoglobulin one of the human heavy (respectively light) chain variable regions that is most homologous to the heavy (respectively light) chain variable region of the donor immunoglobulin, fewer amino acids will be changed in going from the donor immunoglobulin to the humanized immunoglobulin. Hence, and again without intending to be bound by theory, it is believed that there is a smaller chance of changing an amino acid near the CDR's that distorts their conformation. Moreover, the precise overall shape of a humanized antibody comprising the humanized immunoglobulin chain may more closely resemble the shape of the donor antibody, also reducing the chance of distorting the CDR's.

Typically, one of the 3-5 most homologous heavy chain variable region sequences in a representative collection of at least about 10 to 20 distinct human heavy chains will be chosen as an acceptor to provide the heavy chain framework, and similarly for the light chain. Preferably, one of the 1-3 most homologous variable regions will be used. The selected acceptor immunoglobulin chain will most preferably have at least about 65% homology in the framework region to the donor immunoglobulin.

In many cases, it may be considered preferable to use light and heavy chains from the same human antibody as acceptor sequences, to be sure the humanized light and heavy chains will make favorable contacts with each other. Regardless of how the acceptor immunoglobulin is chosen, higher affinity may be achieved by selecting a small number of amino acids in the framework of the humanized immunoglobulin chain to be the same as the amino acids at those positions in the donor rather than in the acceptor.

Humanized antibodies generally have advantages over mouse or in some cases chimeric antibodies for use in human therapy: because the effector portion is human, it may interact better with the other parts of the human immune system (e.g., destroy the target cells more efficiently by complement-dependent cytotoxicity (CDC) or antibody-dependent cellular cytotoxicity (ADCC)); the human immune system should not recognize the framework or constant region of the humanized antibody as foreign, and therefore the antibody response against such an antibody should be less than against a totally foreign mouse antibody or a partially foreign chimeric antibody.

Antibodies can also be genetically engineered. Particularly preferred are humanized immunoglobulins that are produced by expressing recombinant DNA segments encoding the heavy and light chain CDR's from a donor immunoglobulin capable of binding to a desired antigen, such as the tumor antigens e.g. HER2, attached to DNA segments encoding acceptor human framework regions.

The DNA segments typically further include an expression control DNA sequence operably linked to the humanized immunoglobulin coding sequences, including naturally-associated or heterologous promoter regions. Preferably, the expression control sequences will be eukaryotic promoter systems in vectors capable of transforming or transfecting eukaryotic host cells, but control sequences for prokaryotic hosts may also be used. Once the vector has been incorporated into the appropriate host, the host is maintained under conditions suitable for high level expression of the nucleotide sequences, and, as desired, the collection and purification of the humanized light chains, heavy chains, light/heavy chain dimers or intact antibodies, binding fragments or other immunoglobulin forms may follow (see, S. Beychok, Cells of Immunoglobulin Synthesis, Academic Press, New York, (1979), which is incorporated herein by reference).

Human constant region DNA sequences can be isolated in accordance with well known procedures from a variety of human cells, but preferably immortalized B-cells. The CDR's for producing preferred immunoglobulins of the present invention will be similarly derived from monoclonal antibodies capable of binding to the predetermined antigen, such as the human T cell receptor CD3 complex, and produced by well known methods in any convenient mammalian source including, mice, rats, rabbits, or other vertebrates, capable of producing antibodies. Suitable source cells for the constant region and framework DNA sequences, and host cells for immunoglobulin expression and secretion, can be obtained from a number of sources, such as the American Type Culture Collection ("Catalogue of Cell Lines and Hybridomas," sixth edition (1988) Rockville, Md., U.S.A., which is incorporated herein by reference).

Other "substantially homologous" modified immunoglobulins to the native sequences can be readily designed and manufactured utilizing various recombinant DNA techniques well known to those skilled in the art. For example, the framework regions can vary at the primary structure level by several amino acid substitutions, terminal and intermediate additions and deletions, and the like. Moreover, a variety of different human framework regions may be used singly or in combination as a basis for the humanized immunoglobulins of the present invention. In general, modifications of the genes may be readily accomplished by a variety of well-known techniques, such as site-directed mutagenesis (see, Gillman and Smith, *Gene*, 8, 81-97 (1979) and S. Roberts et al., *Nature*, 328, 731-734 (1987), both of which are incorporated herein by reference).

Substantially homologous immunoglobulin sequences are those which exhibit at least about 85% homology, usually at least about 90%, and preferably at least about 95% homology with a reference immunoglobulin protein.

Alternatively, polypeptide fragments comprising only a portion of the primary antibody structure may be produced, which fragments possess one or more immunoglobulin activities (e.g., complement fixation activity). These polypeptide fragments may be produced by proteolytic cleavage of intact antibodies by methods well known in the art, or by inserting stop codons at the desired locations in vectors known to those skilled in the art, using site-directed mutagenesis.

As stated previously, the DNA sequences can be expressed in hosts after the sequences have been operably linked to (i.e., positioned to ensure the functioning of) an expression control sequence. These expression vectors are typically replicable in the host organisms either as episomes or as an integral part of the host chromosomal DNA. Commonly, expression vectors contain selection markers, e.g., tetracycline or neomycin resistance, to permit detection of those cells transformed with the desired DNA sequences (see, e.g., U.S. Pat. No. 4,704,362, which is incorporated herein by reference).

*E. coli* is one prokaryotic host useful particularly for cloning the DNA sequences of the present invention. Other microbial hosts suitable for use include bacilli, such as *Bacillus subtilis*, and other enterobacteriaceae, such as *Salmonella, Serratia*, and various *Pseudomonas* species. In these prokaryotic hosts, one can also make expression vectors, which will typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters will typically control expression, optionally with an operator sequence, and have ribosome binding site sequences and the like, for initiating and completing transcription and translation.

Other microbes, such as yeast, may also be used for expression. *Saccharomyces* is a preferred host, with suitable vectors having expression control sequences, such as promoters, including 3-phosphoglycerate kinase or other glycolytic enzymes, and an origin of replication, termination sequences and the like as desired.

In addition to microorganisms, mammalian tissue cell culture may also be used to express and produce the polypeptides of the present invention (see, Winnacker, "From Genes to Clones," VCH Publishers, New York, N.Y. (1987), which is incorporated herein by reference). Eukaryotic cells are actually preferred, because a number of suitable host cell lines capable of secreting intact immunoglobulins have been developed in the art, and include the CHO cell lines, various COS cell lines, HeLa cells, preferably myeloma cell lines, etc, and transformed B-cells or hybridomas. Expression vectors for these cells can include expression control sequences, such as an origin of replication, a promoter, an enhancer (Queen et al., *Immunol. Rev.*, 89, 49-68 (1986), which is incorporated herein by reference), and necessary processing information sites, such as ribosome binding sites, RNA splice sites, polyadenylation sites, and transcriptional terminator sequences. Preferred expression control sequences are promoters derived from immunoglobulin genes, SV40, Adenovirus, cytomegalovirus, Bovine Papilloma Virus, and the like.

The vectors containing the DNA segments of interest (e.g., the heavy and light chain encoding sequences and expression control sequences) can be transferred into the host cell by well-known methods, which vary depending on the type of cellular host. For example, calcium chloride transfection is commonly utilized for prokaryotic cells, whereas calcium phosphate treatment or electroporation may be used for other cellular hosts. (See, generally, Maniatis et al., Molecular Cloning: A Laboratory Manual, Cold Spring Harbor Press, (1982), which is incorporated herein by reference.)

Once expressed, the whole antibodies, their dimers, individual light and heavy chains, or other immunoglobulin forms of the present invention, can be purified according to standard procedures of the art, including ammonium sulfate precipitation, affinity columns, column chromatography, gel electrophoresis and the like (see, generally, R. Scopes, "Protein Purification", Springer-Verlag, N.Y. (1982)). Substantially pure immunoglobulins of at least about 90 to 95% homogeneity are preferred, and 98 to 99% or more homogeneity most preferred, for pharmaceutical uses. Once purified, partially or to homogeneity as desired, the polypeptides may then be used therapeutically (including extracorporeally) or in developing and performing assay procedures, immunofluorescent staining, and the like. (See, generally, Immunological Methods, Vols. I and II, Lefkovits and Pernis, eds., Academic Press, New York, N.Y. (1979 and 1981)).

In general, the subject humanized antibodies are produced by obtaining nucleic acid sequences encoding the variable heavy and variable light sequences of an antibody which binds a tumor antigen, preferably HER2/neu, identifying the CDR's in the variable heavy and variable light sequences, and grafting such CDR nucleic acid sequences onto human framework nucleic acid sequences.

Preferably, the selected human framework will be one that is expected to be suitable for in vivo administration, i.e., does not exhibit immunogenicity. This can be determined, e.g., by prior experience with in vivo usage of such antibodies and by studies of amino acid sequence similarities. In the latter approach, the amino acid sequences of the framework regions of the antibody to be humanized, are compared to those of known human framework regions, and human framework regions used for CDR grafting are selected which comprise a size and sequence most similar to that of the parent antibody, e.g., a murine antibody which binds HER2/neu. Numerous human framework regions have been isolated and their sequences reported in the literature. See, e.g., Kabat et al., (Kabat et al., *J. Biol. Chem.* 252, 6609-6616 (1977) and Kabat et al., Sequences of protein of immunological interest (1991)). This enhances the likelihood that the resultant CDR-grafted "humanized" antibody, which contains the CDR's of the parent (e.g., murine) antibody grafted onto the selected human framework regions significantly retain the antigen binding structure and thus the binding affinity of the parent antibody.

Methods for cloning nucleic acid sequences encoding immunoglobulins are well known in the art and are described in detail in the Examples which follow. Such methods generally involve the amplification of the immunoglobulin sequences to be cloned using appropriate primers by polymerase chain reaction (PCR). Primers suitable for amplifying immunoglobulin nucleic acid sequences, and specifically murine variable heavy and variable light sequences have been reported in the literature. After such immunoglobulin sequences have been cloned, they are sequenced by methods well known in the art. This will be effected in order to identify the variable heavy and variable light sequences, and more specifically the portions thereof which constitute the CDR's and FRs. This can be effected by well known methods.

Once the CDRs and FRs of the cloned antibody sequences which are to be humanized have been identified, the amino acid sequences encoding CDRs are then identified (deduced based on the nucleic acid sequences and the genetic code and by comparison to previous antibody sequences) and the corresponding nucleic acid sequences are grafted onto selected human FRs. This may be accomplished by use of appropriate primers and linkers. Methods for selecting suitable primers and linkers to provide for ligation of desired nucleic acid sequences is well within the purview of the ordinary artisan and include those disclosed in U.S. Pat. No. 4,816,397 to Boss et al. and U.S. Pat. No. 5,225,539 to Winter et al.

After the CDRs are grafted onto selected human FRs, the resultant "humanized" variable heavy and variable light sequences will then be expressed to produce a humanized chimeric fusion molecule which binds, for example, HER2/neu. The humanized variable heavy and/or variable light sequences will be expressed as a fusion protein so that an intact chimeric fusion molecule which binds, for example, HER2/neu is produced.

In another preferred embodiment, the variable heavy and light sequences can also be expressed in the absence of constant sequences to produce a humanized Fv chimeric fusion molecule which binds, for example, HER2/neu. However, fusion of human constant sequences to the humanized variable region(s) is potentially desirable because the resultant humanized antibody which binds, for example, HER2/neu will then possess human effector functions such as complement-dependent cytotoxicity (CDC) and antibody-dependent cellular cytotoxicity (ADCC) activity.

The following references are representative of methods and vectors suitable for expression of recombinant immunoglobulins which may be utilized in carrying out the present invention. Weidle et al., *Gene,* 51:21-29 (1987); Dorai et al., *J. Immunol.,* 13(12):4232-4241 (1987); De Waele et al., *Eur. J. Biochem.,* 176:287-295 (1988); Colcher et al., *Cancer Res.,* 49:1738-1745 (1989); Wood et al., *J. Immunol.,* 145(a):3011-3016 (1990); Bulens et al., *Eur. J. Biochem.,* 195:235-242 (1991); Beggington et al., *Biol. Technology,* 10:169 (1992); King et al., *Biochem. J.,* 281: 317-323 (1992); Page et al., *Biol. Technology,* 9:64 (1991); King et al., *Biochem. J.,* 290:723-729 (1993); Chaudary et al., *Nature,* 339:394-397 (1989); Jones et al., *Nature,* 321: 522-525 (1986); Morrison and Oi, *Adv. Immunol,* 44:65-92 (1988); Benhar et al., *Proc. Natl. Acad. Sci. USA,* 91:12051-12055 (1994); Singer et al., *J. Immunol.,* 150:2844-2857 (1993); Cooto et al., *Hybridoma,* 13(3):215-219 (1994); Queen et al., *Proc. Natl. Acad. Sci. USA,* 86:10029-10033 (1989); Caron et al., *Cancer Res.,* 32:6761-6767 (1992); Cotoma et al., *J. Immunol. Meth.,* 152:89-109 (1992). Moreover, vectors suitable for expression of recombinant antibodies are commercially available. The vector may, e.g., be a bare nucleic acid segment, a carrier-associated nucleic acid segment, a nucleoprotein, a plasmid, a virus, a viroid, or a transposable element.

Host cells known to be capable of expressing functional immunoglobulins include, e.g.: mammalian cells such as Chinese Hamster Ovary (CHO) cells; COS cells; myeloma cells, such as NSO and SP2/0 cells; bacteria such as *Escherichia coli*; yeast cells such as *Saccharomyces cerevisiae*; and other host cells. SP2/0 cells are one of the preferred types of host cells useful in the present invention.

After expression, the antigen binding affinity of the resulting humanized antibody will be assayed by known methods, e.g., Scatchard analysis. In a particularly preferred embodiment, the antigen-binding affinity of the humanized antibody will be at least 50% of that of the parent antibody, e.g., anti-HER2/neu, more preferably, the affinity of the humanized antibody will be at least about 75% of that of the parent antibody, more preferably, the affinity of the humanized antibody will be at least about 100%, 150%, 200% or 500% of that of the parent antibody.

In some instances, humanized antibodies produced by grafting CDRs (from an antibody which binds, for example, a tumor antigen such as, for example, HER/neu) onto selected human framework regions may provide humanized antibodies having the desired affinity to HER2/neu. However, it may be necessary or desirable to further modify specific residues of the selected human framework in order to enhance antigen binding. This may occur because it is believed that some framework residues are essential to or at least affect antigen binding. Preferably, those framework residues of the parent (e.g., murine) antibody which maintain or affect combining-site structures will be retained. These residues may be identified by X-ray crystallography of the parent antibody or Fab fragment, thereby identifying the three-dimensional structure of the antigen-binding site. Also, framework residues involved in antigen binding may potentially be identified based on previously reported humanized murine antibody sequences. Thus, it may be beneficial to retain such framework residues or others from the parent murine antibody to optimize, for example, HER2/neu binding. Preferably, such methodology will confer a "human-like" character to the resultant humanized antibody thus rendering it less immunogenic while retaining the interior and contacting residues which affect antigen-binding.

The present invention further embraces variants and equivalents which are substantially homologous to the humanized antibodies and antibody fragments set forth herein. These may contain, e.g., conservative substitution mutations, i.e. the substitution of one or more amino acids by similar amino acids. For example, conservative substitution refers to the substitution of an amino acid with another within the same general class, e.g., one acidic amino acid with another acidic amino acid, one basic amino acid with another basic amino acid, or one neutral amino acid by another neutral amino acid. What is intended by a conservative amino acid substitution is well known in the art.

Methods of Delivering a Chimeric Molecule to a Cell

The invention also provides a method of delivering an anti-angiogenic agent-carrier chimeric molecule to a cell. The chimeric molecules of the invention can be delivered to a cell by any known method. For example, a composition containing the chimeric molecule can be added to cells suspended in medium. Alternatively, a chimeric molecule can be administered to an animal (e.g., by a parenteral route) having a cell expressing a receptor that binds the chimeric molecule so that the chimeric molecule binds to the cell in situ. For example, the chimeric molecules of this invention that feature an Ig domain that is specific for HER2/neu are particularly well suited as targeting moieties for binding tumor cells that over express HER2/neu, e.g., breast cancer and ovarian cancer cells.

Administration of Compositions to Animals

For targeting a tumor cell in situ, the compositions described above may be administered to animals including human beings in any suitable formulation. For example, compositions for targeting a tumor cell may be formulated in pharmaceutically acceptable carriers or diluents such as physiological saline or a buffered salt solution. Suitable carriers and diluents can be selected on the basis of mode and route of administration and standard pharmaceutical practice. A description of exemplary pharmaceutically acceptable carriers and diluents, as well as pharmaceutical formulations, can be found in Remington's Pharmaceutical Sciences, a standard text in this field, and in USP/NF. Other substances may be added to the compositions to stabilize and/or preserve the compositions.

The compositions of the invention may be administered to animals by any conventional technique. The compositions may be administered directly to a target site by, for example, surgical delivery to an internal or external target site, or by catheter to a site accessible by a blood vessel. Other methods of delivery, e.g., liposomal delivery or diffusion from a device impregnated with the composition, are known in the art. The compositions may be administered in a single bolus, multiple injections, or by continuous infusion (e.g., intravenously). For parenteral administration, the compositions are preferably formulated in a sterilized pyrogen-free form. In preferred embodiments, the compositions are administered intravenously, parenterally, intra muscularly and the like.

Methods of Treatment

In a preferred embodiment, a method of treating a patient with cancer comprises administering to a patient a chimeric fusion molecule comprising the chimeric fusion molecules described herein.

In a preferred embodiment, the chimeric fusion molecule comprises a polypeptide comprising an anti-HER2 binding domain and an endostatin molecule having a proline substituted with alanine at amino acid position 125.

The chimeric molecules described herein have been found to exhibit superior anti-angiogenic properties as compared to endostatin or Herceptin alone. For example, treatment of tumors with Herceptin alone results in Herceptin resistance and the tumors continue to proliferate. Furthermore, these chimeric molecules treat tumors termed Her2⁻ which have low levels of Her and have been shown to be untreatable with Herceptin. The chimeric fusion molecules are thus useful in treating Her2 refractory tumors.

Clinical experience with endostatin has been disappointing (Thomas J P, et al. *J Clin Oncol* 2003; 21(2):223-31; Hansma A H, et al. *Ann Oncol* 2005; 16(10):1695-701; Kulke M H, et al. *J Clin Oncol* 2006; 24(22):3555-6). In early human Phase I trials, huEndo administration at variable dose levels and schedules was feasible and safe. However, no consistent evidence for anti-tumor activity or biological activity was demonstrated. In a Phase II study in forty-two patients with advanced pancreatic neuroendocrine tumors or carcinoid tumors treated with huEndo administered as a twice a day subcutaneous injection, huEndo was associated with minimal toxicity. However, no patient achieved a partial response and only two patients had a biochemical response. Therefore, although initial clinical trials proved that endostatin is a very safe drug delivered in a variety of dose schedules, they did not demonstrate comparable anti-tumor activity compared to that seen in murine models. In contrast, the chimeric fusion molecules described herein, are therapeutically effective. Details of the results are shown in the examples which follow.

In a preferred embodiment, the chimeric fusion molecule can be targeted to any tumor specific antigen. Examples include, but not limited to HER2/neu tumor antigens, phosphatase and tensin homolog (PTEN), phosphatidylinositol (PI) kinase and receptor thereof, Eph, VEGF and receptors thereof, receptor/ligand complexes; ligands, receptors, mutants, fragments, alleles and variants thereof.

In another preferred embodiment, the chimeric fusion molecules described herein are administered metronomically either alone or in combination with one or more other compounds. These compounds include, for example, anti-angiogenic compounds, chemotherapeutic compounds, cell cycle arresting compounds, chemokines, cytokines and the like. Examples include, but not limited to: angiogenin, angiostatin, chemokines, angioarrestin, angiostatin (plasminogen fragment), basement-membrane collagen-derived anti-angiogenic factors (tumstatin, canstatin, or arrestin), anti-angiogenic antithrombin III, signal transduction inhibitors, cartilage-derived inhibitor (CDI), CD59 complement fragment, fibronectin fragment, gro-beta, heparinases, heparin hexasaccharide fragment, human chorionic gonadotropin (hCG), interferon alpha/beta/gamma, interferon inducible protein (IP-10), interleukin-12, kringle 5 (plasminogen fragment), metalloproteinase inhibitors (TIMPs), 2-methoxyestradiol, placental ribonuclease inhibitor, plasminogen activator inhibitor, platelet factor-4 (PF4), prolactin 16 kD fragment, proliferin-related protein (PRP), various retinoids, tetrahydrocortisol-S, thrombospondin-1 (TSP-1), transforming growth factor-beta (TGF-b), vasculostatin, vasostatin (calreticulin fragment) and the like. These molecules include all forms, variants, mutations, alleles, substitutes, fragments and analogs thereof.

In another preferred embodiment, the chimeric fusion molecules care administered with one or more compounds comprising: with one more compounds comprising signal transduction inhibitors, bevacizumab (Avastin), antiangiogenic compounds such as for example, sunitinib, sorafenib, celebrex, MTOR inhibitors, AKT inhibitors, P13K and the like, anti-PDL1 and/or CTLA4. One of ordinary skill in the art would identify which other therapeutic compounds could be administered in conjunction with a therapy comprising a regimen of chimeric fusion molecule.

Administration of Compositions to Animals

For targeting a tumor cell in situ, the compositions described above may be administered to animals including human beings in any suitable formulation. For example, compositions for targeting a tumor cell may be formulated in pharmaceutically acceptable carriers or diluents such as physiological saline or a buffered salt solution. Suitable carriers and diluents can be selected on the basis of mode and route of administration and standard pharmaceutical practice. A description of exemplary pharmaceutically acceptable carriers and diluents, as well as pharmaceutical formulations, can be found in Remington's Pharmaceutical Sciences, a standard text in this field, and in USP/NF. Other substances may be added to the compositions to stabilize and/or preserve the compositions.

The compositions of the invention may be administered to animals by any conventional technique. The compositions may be administered directly to a target site by, for example, surgical delivery to an internal or external target site, or by catheter to a site accessible by a blood vessel. Other methods of delivery, e.g., liposomal delivery or diffusion from a device impregnated with the composition, are known in the art. The compositions may be administered in a single bolus, multiple injections, or by continuous infusion (e.g., intravenously). For parenteral administration, the compositions are preferably formulated in a sterilized pyrogen-free form.

Formulations

While it is possible for an antibody or fragment thereof to be administered alone, it is preferable to present it as a pharmaceutical formulation. The active ingredient may comprise, for example, from 0.001% to 100% w/w, e.g., from 1% to 50% by weight of the formulation, although it may comprise as much as 99.9999% w/w of the formulation.

Formulations suitable for topical administration include liquid or semi-liquid preparations suitable for penetration through the skin to the site of where treatment is required, such as liniments, lotions, creams, ointments or pastes, and drops suitable for administration to the eye, ear, or nose. Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably including a surface active agent. The resulting solution may then be clarified and sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Kits

Kits according to the present invention include frozen or lyophilized chimeric fusion molecules, humanized or human antibodies or humanized or human antibody fragments to be reconstituted, respectively, by thawing (optionally followed by further dilution) or by suspension in a (preferably buffered) liquid vehicle. The kits may also include buffer and/or excipient solutions (in liquid or frozen form)—or buffer and/or excipient powder preparations to be reconstituted with water—for the purpose of mixing with the fusion molecules or antibody fragments to produce a formulation suitable for administration. Thus, preferably the kits containing the chimeric fusion molecules, humanized antibodies or humanized antibody fragments are frozen, lyophilized, pre-diluted, or pre-mixed at such a concentration that the addition of a predetermined amount of heat, of water, or of a solution provided in the kit will result in a formulation of sufficient concentration and pH as to be effective for in vivo or in vitro use in the treatment or diagnosis of cancer. Preferably, such a kit will also comprise instructions for reconstituting and using the chimeric fusion molecules, humanized antibody or humanized antibody fragment composition to treat or detect cancer. The kit may also comprise two or more component parts for the reconstituted active composition. For example, a second component part—in addition to the chimeric fusion molecule, humanized antibodies or humanized antibody fragments—may be bifunctional chelant, bifunctional chelate, or a therapeutic agent such as a radionuclide, which when mixed with the humanized antibodies or humanized antibody fragments forms a conjugated system therewith. The above-noted buffers, excipients, and other component parts can be sold separately or together with the kit.

It will be recognized by one of skill in the art that the optimal quantity and spacing of individual dosages of a chimeric fusion molecule, antibody or antibody fragment of the invention will be determined by the nature and extent of the condition being treated, the form, route and site of administration, and the particular animal being treated, and that such optima can be determined by conventional techniques. It will also be appreciated by one of skill in the art that the optimal course of treatment, i.e., the number of doses of an antibody or fragment thereof of the invention given per day for a defined number of days, can be ascertained by those skilled in the art using conventional course of treatment determination tests.

Anti-Cancer and Chimeric Fusion Molecule Cocktails

The subject chimeric fusion molecules, including the humanized chimeric fusion molecules may also be administered in combination with other anti-cancer agents, e.g., other antibodies or drugs. Also, the subject chimeric molecules or fragments may be directly or indirectly attached to effector having therapeutic activity. Suitable effector moieties include by way of example cytokines (IL-2, TNF, interferons, colony stimulating factors, IL-1, etc.), cytotoxins (*Pseudomonas* exotoxin, ricin, abrin, etc.), radionuclides, such as $^{90}$Y, $^{131}$I, $^{111}$In, $^{125}$I, among others, drugs (methotrexate, daunorubicin, doxorubicin, etc.), immunomodulators, therapeutic enzymes (e.g., beta-galactosidase), anti-proliferative agents, etc. The attachment of antibodies to desired effectors is well known. See, e.g., U.S. Pat. No. 5,435,990 to Cheng et al. Moreover, bifunctional linkers for facilitating such attachment are well known and widely available. Also, chelators (chelants and chelates) providing for attachment of radionuclides are well known and available.

The subject chimeric fusion molecules may be used alone or in combination with other antibodies, e.g. anti-HER2/neu.

Effects on Angiogenesis and Vasculogenic Mimicry

In one embodiment, the present fusion molecules can be used for interfering with angiogenesis in tumors. The method comprises administering to an individual who has a tumor an effective amount of a chimeric fusion molecule composition, comprising an anti-HER2 antigen binding domain and an endostatin protein or fragments, or an anti-EGFR antigen binding domain and an endostatin protein or fragments. In one embodiment, the endostatin protein or fragments have a proline to alanine substitution at the 125 position of human endostatin. Exemplary fusion molecules are anti-HER2-huEndoP125A and anti-EGFR-huEndoP125A.

Formation of blood vessels is considered to be important for the growth of tumors. The ability of certain tumor cells to exhibit formation of tube like structures can be demonstrated in vitro or in vivo and is generally referred to as vasculogenic mimicry. For example, vasculogenic mimicry can be demonstrated as the ability to form tube-like structures in a 3-D matrix in vitro. A commonly used 3-D matrix in culture is matrigel. It is considered that this in vitro ability correlates with vasculogenic mimicry in vivo (See Misra et al., Vasculogenic Mimicry of HT1080 Tumour Cells In Vivo: Critical Role of HIF-1α-Neuropilin-1 Axis. PLoS ONE 7(11): e50153.0.) In the present disclosure, it was observed that while huEndo or huEndoP125A alone did not have any effect on vasculogenic mimicry, the fusion molecules of this disclosure (such as anti-HER 2-EndostatinP125A and anti-EGFR-EndostatinP125A) had a greater effect on vasculogenic mimcry than similar fusion molecules that do not have the P125A substitution. While not intending to be bound by any particular theory, it is considered that due to the formation of the fusion protein, a dimeric form of the mutant endostatin can be delivered to the cells. It is considered that the delivery of a dimeric form of huEndoP125A by anti-HER 2 or anti-EGFR antibody may contribute to the unexpected enhanced inhibition of vasculogenic mimictry. Thus, in one embodiment, this disclosure provides a method for inhibiting vasculogenic mimicry in tumors comprising administering to an individual a chimeric fusion molecule composition, comprising an anti-HER2 antigen binding domain and an endostatin protein or fragments, or an anti-EGFR antigen binding domain and an endostatin protein or fragments. In one embodiment, the endostatin protein or fragments have a proline to alanine substitution at the 125 position of human endostatin. Exemplary fusion molecules are anti-HER2-huEndoP125A and anti-EGFR-huEndoP125A.

In one embodiment, this disclosure provides a method of inhibiting angiogenesis as well as vasculogenic mimcry (for tumors that exhibit vasculogenic mimcry) comprising administering to an individual who has a tumor an effective amount of a chimeric fusion molecule composition comprising the fusion proteins of the present disclosure (such as anti-HER 2-huEndoP125A or anti-EGFR-huEndoP125A). The ability of the fusion molecules of the present disclosure to inhibit both angiogenesis and vasculogenic mimicry is unexpected and should lead to an enhanced anti-tumor effect.

In one embodiment, this disclosure provides a method for reducing the formation of metastatic foci (metastasis) or recurrence of tumors comprising the steps of administering to an individual who has or had a tumor an effective amount of a chimeric fusion molecule composition comprising the fusion proteins of the present disclosure (such as anti-HER 2-huEndoP125A or anti-EGFR-huEndoP125A).

In one embodiment, this disclosure provides a method for identifying treatment options for an individual diagnosed with a tumor comprising determining if the tumor exhibits vasculogenic mimicry (such as in vitro or in vivo) and if so, determining if the fusion proteins of the present disclosure (such as anti-HER 2-huEndoP125A or anti-EGFR-huEndoP125A) inhibit vasculogenic mimicry. If inhibition of vasculogenic mimicry is observed, treatment options can be devised for the individual that employ administration of the fusion proteins. The ability of tumors to exhibit vasculogenic mimicry can be evaluated in vitro (by morphological analysis of cells in culture) or by immunohistochemical techniques in vivo. For example, tumor cells can be obtained in a biopsy and suspended in suitable culture medium (such as endothelial cell growth medium (EGM) or other cell culture media including serum-free media). The cells can be plated on matrigel coated plates. Following a suitable period of growth (such as 10-20 hours at 37° C. in a humidified atmosphere generally containing 5% $CO_2$), the plates can be examined for tube formation. The ability of tumor cells to exhibit vasculogenic mimicry may also be inferred by evaluating for the presence of angiogenic markers including Neuropilin-1 (NRP-1) (See Misra et al. 2012, PLoS ONE 7(11): e50153.0.)

In another embodiment, the administration of the fusion proteins is combined with other modalities of treatment including surgical removal of the tumor or radiation treatment. For example, in one embodiment, the fusion proteins of the present disclosure (such as anti-HER2-huEndoP125A or anti-EGFR-huEndoP125A) can be administered to an individual following surgical removal of the tumor. In one embodiment, the fusion proteins of the present disclosure (such as anti-HER2-huEndoP125A or anti-EGFR-huEndoP125A) are administered to an individual following radiation treatment, which may be combined with surgical removal. It is considered that administration of the fusion proteins may reduce metastatic lesions or recurrence of the tumors. In one embodiment, the fusion molecules of the present disclosure (such as anti-HER 2-huEndoP125A or anti-EGFR-huEndoP125A) can be administered to an individual before, during or after surgical removal of the tumor or before, during or after radiation treatment.

Without further elaboration, it is believed that one skilled in the art can, using the preceding description, utilize the present invention to its fullest extent. The following examples are offered by way of illustration, not by way of limitation. While specific examples have been provided, the above description is illustrative and not restrictive. Any one or more of the features of the previously described embodiments can be combined in any manner with one or more features of any other embodiments in the present invention. Furthermore, many variations of the invention will become apparent to those skilled in the art upon review of the specification.

All publications and patent documents cited in this application are incorporated by reference in pertinent part for all purposes to the same extent as if each individual publication or patent document were so individually denoted. By their citation of various references in this document, Applicants do not admit any particular reference is "prior art" to their invention.

EXAMPLES

The present invention is further illustrated by the following specific examples. The examples are provided for illustration only and are not to be construed as limiting the scope or content of the invention in any way.

Materials & Methods

Cell Lines and Animals:

CT26, CT26-HER2, human embryonic kidney (HEK) 293, and transfected Sp2/0 cells were cultured in Iscove's Modified Dulbecco's Medium (IMDM; Cellgro, Mediatech, Inc., Herndon, Va.) with 5% calf serum (GIBCO, Invitrogen Corp. Carlsbad, Calif.). Female BALB/c mice (4-6 weeks) and SCID mice (4-6 weeks) were purchased from the Jackson Laboratory (Bar Harbor, Me.). Animal care and use procedures were performed in accordance with standards described in the National Institutes of Health Guide for Care and Use of Laboratory Animals.

Construction, Expression, and Characterization of Anti-HER2/neu IgG3-Endostatin Fusion Protein:

Experimental murine endostatin gene originated from pFLAG-CMV-1-endostatin by PCR using primers 5'-CCCCTCGCGATATCATACTCATCAGGACTTTCA-GCC-3' (SEQ ID NO 1) and 5'-CCCCGAATTCGTTAAC-CTTTGGAGAAAGAGGTCATGAAG-C-3' (SEQ ID NO 2). PCR products were subcloned into p-GEM-T Easy Vector (Promega, Madison, Wis.), then sequenced for verification. The EcORV-EcOR1 fragment of the subcloned endostatin gene was ligated to the carboxyl end of the heavy chain constant domain ($C_H3$) of human IgG3 in the vector pAT135, as previously described (Shin S U et al. *J Immunol.* 1997; 158(10):4797-804). To complete the construct, the IgG3-endostatin heavy chain constant region (AgeI-BamHI) was then joined to an anti-HER2/neu variable region of a recombinant humanized monoclonal antibody 4D5-8 (rhuMAb HER2, Herceptin; Genentech, San Francisco, Calif.) in the expression vector (pSV2-his) containing HisD gene for eukaryotic selection (Challita-Eid P M. et al. *J Immunol* 1998; 160(7):3419-26; Coloma M J. et al, *J. Immunol. Methods* 1992; 152:89-104). The finished anti-HER2/neu heavy chain IgG3-endostatin construction vector was transfected by electroporation into Sp2/0 cells stably expressing the anti-HER2/neu K light chain in order to assemble entire anti-HER2/neu IgG3-endostatin fusion proteins. Transfected cells were selected with 5 mM histidinol and transfectomas producing the fusion proteins were identified by a enzyme-linked immunosorbent assay (ELISA) using anti-human IgG antibody coated plates and an anti-human kappa detection antibody (Sigma, Saint Louis, Mo.). The anti-HER2/neu IgG3-endostatin fusion proteins were biosynthetically labeled with [$^{35}$S]methionine (Amersham Biosciences, Piscataway, N.J.) and analyzed by SDS-PAGE on 5% sodium phosphate buffered polyacrylamide gels without reduction or on 12.5% Tris-glycine buffered polyacrylamide gels following treatment with 0.15 M β-mercaptoethanol at 37° C. for 30 min. The fusion protein was purified from culture supernatants using protein A immobilized on Sepharose 4B fast flow (Sigma, Saint Louis, Mo.).

To obtain active endostatin, a mouse endostatin expression vector (pFLAG-CMV-1-endostatin) was co-transfected with pcDNA3.1 (CLONTECH, Palo Alto, Calif.) into human embryonic kidney (HEK) 293 cells, and G418 (0.6 μg/ml)-resistant cells selected. Secreted endostatin was harvested from serum-free conditioned medium and purified in a heparin-Sepharose CL-6B column. Purity was assessed by Coomassie blue staining of the SDS-PAGE gels. For Western blot analysis, the endostatin fusion proteins were treated with β-mercaptoethanol, fractionated by SDS-PAGE and transferred onto a membrane. Rabbit anti-endostatin (BodyTech, Kangwon-Do, Korea) was used as the primary antibody and mouse anti-rabbit IgG conjugated with HRP (Sigma, St. Louis, Mo.) was used as the secondary antibody. Goat anti-human IgG conjugated with HRP (Sigma, Saint Louis, Mo.) was used to detect human antibody.

Chorioallantoic Membrane (CAM) Assay:

The ability of anti-HER2/neu IgG3-endostatin to block VEGF/bFGF-induced angiogenesis was tested by CAM assay, which employed Leghorn chicken embryos (Charles River SPAFAS, Wilmington, Mass.) at 12-14 days of embryonic development. Vitrogen gel pellets (Collagen Biomaterials, Palo Alto, Calif.) were supplemented with (a) vehicle (0.1% DMSO) in PBS alone (negative control); (b) VEGF/bFGF (100 ng and 50 ng/pellet, respectively; positive control); or (c) VEGF/bFGF and either of anti-HER2/neu IgG3, anti-HER2/neu IgG3-endostatin, or endostatin, at various concentrations (0.5-10 μg/pellet) and were allowed to polymerize at 37° C. for 2 h. Pellets were then placed on a nylon mesh (pore size 250 μm; Tetko Inc., USA) and polymerized mesh was placed onto the outer region of the chorioallantoic membrane of the embryo and incubated for 24 hours as described (Iruela-Arispe M L, et al. *Thromb. Haemost.* 1997; 78(1):672-7; Iruela-Arispe M L, et al. *Circulation* 1999; 100(13):1423-31). To visualize vessels, 400 μl of fluorescein isothiocyanate-dextran (100 μg/ml, Sigma, USA) was injected in the chick embryo blood stream. After 5-10 min of incubation, the chick embryo was topically fixed with 3.7% formaldehyde for 5 min. The implanted mesh was then dissected and mounted on slides. Fluorescence intensity was analyzed with a computer-assisted image program (NIH Image 1.59).

Pharmacokinetic and Biodistribution of Anti-HER2/neu IgG3-Endostatin:

Anti-HER2/neu IgG3 (100 μg), anti-HER2/neu IgG3-endostatin (100 μg), anti-dansyl IgG3 (100 μg), and endostatin (100 μg) were iodinated with 0.5 mCi of [$^{125}$I] (Amersham Biosciences, Piscataway, N.J.) by the chloramine T method (Pardridge W M, et al. Proc. Natl. Acad. Sci. USA 1995; 92:5592.). BALB/c mice (4-6 weeks of age) were injected s.c. with either 1×10$^6$ CT26-HER2 or CT26 cells or left uninjected. Groups of three mice with either CT26-HER2 or CT26 tumors or no tumor were injected i.v. with either 32 μCi of [$^{125}$I]-anti-HER2/neu IgG3, 30 μCi of [$^{125}$I]-anti-HER2/neu IgG3-endostatin, 32 μCi of [$^{125}$I]-anti-dansyl IgG3, or 24 μCi of [$^{125}$I]-endostatin. Blood samples were serially obtained at various intervals ranging from 15 min to 96 hours from the retro-orbital plexus of mice injected with either the anti-HER2/neu IgG3, anti-HER2/neu IgG3-endostatin, or anti-dansyl IgG3. Mice injected with endostatin alone were bled within 15 second to 60 min after the i.v. injection. The TCA precipitable radioactivity in each blood sample was measured in a γ-counter. The pharmacokinetic parameters were calculated by fitting plasma radioactivity data to a bi-exponential equation as described previously (Shin S U, et al. *J Immunol.* 1997; 158(10):4797-804, Yoshikawa T et al. *J Pharmacol. Exp. Ther.* 1992; 263:897; Penichet M L. et al. J. Immunol. 1999; 163(8): 4421-6).

$$Cp(t)=A_1e^{-K_1 t}+A_2e^{-K_2 t}$$

The equation was fitted to plasma data using derivative free nonlinear regression analysis (PARBMDP, Biomedical Computer P series Program developed at UCLA Health Sciences Computing Facilities). Data were weighed using weight=1/(concentration)$^2$, where concentration was either count per minute (cpm) per microliter (μl) or % ID (percentage of injected dose) per milliliter. Area under the plasma concentration curve (AUC) and mean residence time (MRT) were calculated from the slopes and intercept of the bi-exponential equation. The volume of distribution ($V_D$) of the antibodies was determined from the ratio of disintegrations per minute per gram of organ divided by disintegrations per minute per microliters of corresponding plasma at each time after injection. The organ permeability-surface area product (Ki) of the antibodies was calculated from:

$$Ki=[V_D-V_0]Cp(T)/AUC(t)$$

where Cp(T) is the terminal plasma concentration and $V_0$ is the organ plasma volume. The organ delivery of the antibodies was determined from:

$$\% ID/g=Ki \times AUC(t)$$

where Ki and AUC(t) correspond to the 1, 48, or 96 hour time period after injection.

The pharmacokinetic parameters were calculated by fitting plasma TCA-precipitable radioactivity data to a bi-exponential equation as described previously (Shin S U, et al. *J. Immunol.* 1997; 158(10):4797-804., Yoshikawa T et al. *J Pharmacol. Exp. Ther.* 1992; 263:897; Penichet M L. et al. *J Immunol.* 1999; 163(8):4421-6; Gibaldi M. et al. *Phar-*

*macokinetics*, Marcel Dekker, Inc., New York. 1982; Pardridge W M. et al. *J. Pharm. Sci.* 1995; 84:943-8). Plasma clearance, the initial plasma volume, systemic volume of distribution, steady state area under the plasma concentration curve ($AUC_{0-\infty}$), and mean residence time were also determined.

Following the pharmacokinetic experiments, mice were exsanguinated by perfusion with 20 ml PBS for measurements of the tissue distribution of $^{125}$I-labeled antibody-endostatin fusion protein. The heart, lung, liver, spleen, kidney, muscle, and tumor were removed, weighed, γ-counted and the percent of injected dose per gram of tissue calculated. Specific tumor targeting is expressed as the radiolocalization index (the % ID/g in tumor divided by the % ID/g in blood).

To determine the preferential distribution and localization of the $^{125}$I-labeled proteins in mice simultaneously implanted with CT26 and CT26-HER2 tumors on opposite flanks, groups of three mice were injected i.v. with either 5 μCi [$^{125}$I]-anti-HER2/neu IgG3-endostatin fusion protein or 5 μCi [$^{125}$I]-anti-HER2/neu IgG3. The animals were sacrificed at different times (6, 24, and 96 hours) after injection of labeled protein and organs (e.g., lung, liver, kidney, spleen, muscle, CT26 tumor, CT26-HER2 tumor, blood, and urine) were isolated after perfusion of the mouse with PBS, weighed, and counted in a gamma scintillation counter. The percentage of injected dose per gram (% ID/g) for each organ was determined as above.

In Vivo Anti-Tumor Effects:

The in vivo anti-tumor efficacy of anti-HER2/neu IgG3-endostatin was examined using a CT26-HER2 BALB/c syngeneic mouse model and a SK-BR-3 human breast xenograft SCID mouse model. To determine targeting and efficacy of anti-HER2/neu IgG3-endostatin, BALB/c (8/group, 4-6 weeks of age) mice were injected s.c. in the right flank with $1\times10^6$ CT26-HER2 cells and control CT26 cells injected on the left flank. On day seven, mice (8 mice/group) were injected i.v. with the anti-HER2/neu IgG3-endostatin fusion proteins (42 μg/injection, $2\times10^{-10}$ mole, equimolar to 8 μg of endostatin), anti-HER2/neu IgG3 alone (34 μg/injection, $2\times10^{-10}$ mole), endostatin alone (8 μg/injection, $4\times10^{-16}$ mole), the combination of anti-HER2/neu IgG3 (34 μg) and endostatin (8 μg), or PBS as a control. All mice received seven treatments at 2-day intervals. Tumor size and growth rates were recorded and calculated using the following equation:

$$\text{Tumor Volume (mm}^3\text{)} = 4/3 \times 3.14 \times \{(\text{Long axis} + \text{Short axis})/4\}^3$$

Human breast cancer SK-BR-3 xenografts in SCID mice were also used to evaluate anti-tumor activity of anti-HER2/neu IgG3-endostatin fusion protein. SK-BR-3 ($1\times10^6$ cells per mouse) was implanted on the flank of SCID mice. On day 15, mice (8 mice/group) were injected i.v. with the anti-HER2/neu IgG3-endostatin fusion proteins (42 μg), anti-HER2/neu IgG3 (34 μg), the combination of anti-HER2/neu IgG3 (34 μg) and endostatin (8 μg), or endostatin (8 μg). This treatment was repeated every other day. Visible tumors were measured using a caliper and the tumor growth rate analyzed as described above.

Immunohistochemistry and Image Analysis of Blood Vessel Formation:

Mice were killed at the end of the experiments. Tumors were placed in OCT Compound (Tissue-Tek, Elkhart, Ind.) and snap frozen in isopentane chilled with liquid nitrogen. Frozen tumors were stored at −80° C. until further use. For conventional immunohistochemistry, five-μm tissue sections were cut using a cryostat (Shandon, Pittsburgh, Pa.) and placed on positively charged slides (Fisher Scientific, Pittsburgh, Pa.). Tumor sections were air-dried and fixed with 4% paraformaldehyde for 10 min. To analyze the microvessel formation in tumors, sections were stained with a rat anti-mouse platelet-endothelial cell adhesion molecule 1 (PE-CAM-1; CD31) MAb (PharMingen, San Diego, Calif.) and subsequently with the ABC (Vector Lab, Burlingame, Calif.) method. HER2/neu expression on tumors has been examined with staining tumor sections with anti-HER2/neu IgG3-endostatin fusion antibody. All sections were counterstained with hematoxylin (Sigma, St. Louis, Mo.). Positively stained vascular endothelial cells (brown) were visualized and imaged using a digital camera attached to a Zeiss microscope (Carl Zeiss, Thornwood, N.Y.).

For confocal microscopic analysis, thirty-μm cryosections were cut and stained with a rat anti-mouse CD31 monoclonal antibodies. Blood vessels have been visualized with anti-rat IgG-Alexa 594 (Molecular Probes, Eugene, Oreg.) and a coverslip was placed on top of the piece of sections with anti-fade mounting media (Vectorshield: Vector Lab, Burlingame, Calif.). These fluorescent blood vessels were then viewed via LSM5 confocal microscope (Carl Zeiss, Thornwood, N.Y.), and 14-21 digital images were obtained per section. These digital images have been composed as one image per each section to measure blood vessel density, and blood vessel area (pixel) was then computed from the composite images and averaged to measure blood vessel density per tumor. Images were analyzed using NIH ImageJ v1.31 software by color image to form a binary image of the tumor blood vessels.

Statistical Analysis:

Antiangiogenic activity, pharmacokinetics, biodistribution, and tumor growth are presented as the mean±SEM. Two-sided Student's t test was used to determine the significance of differences between two group means. Differences were considered statistically significant at $P<0.05$. All statistical tests were two-sided.

Focus Formation Assay:

Focus formation assay was used to determine whether anti-HER2/neu antibody-endostatin fusions protein exerted antiproliferative effects on tumor bearing HER2/neu antigens. In vitro SK-BR-3, BT474, MCF7-HER2 (positive tumor cells) and MCF7 (negative tumor cell) were treated with different concentrations of anti-HER2/neu antibody-endostatin fusion proteins (0.1, 1, 10 μg/ml). One thousand of tumor cells were plated in 60-mm dishes in 1.5 ml of medium containing 0.33% agar, which were overlaid onto solidified 0.5% agar medium. The medium used for soft agar assays was DMEM containing 10% fetal calf serum, and contained the endostatin fusion proteins. The soft agar plates were fed with 0.5 ml of medium every 5-7 days, and after 14 days, the cells were stained overnight (at 37° C. and 5% $CO_2$) with the vital dye p-iodonitrotetrazolium violet (Sigma), and counted. The resulting foci are stained with crystal violet and counted.

MTT Assay:

If tumor cells did not grow properly on soft agar assays, MTT assays were used to evaluate the antiproliferative effect of anti-HER2/neu antibody-endostatin fusion proteins on tumor expressing HER2/neu. Tumor cells such as SK-BR-3, BT474, MCF7 and MCF7-HER2, CT26 and CT-HER2/neu, or EMT6 and EMT6-HER2/neu were treated with different concentrations (0.1, 1, 10 μg/ml) of anti-HER2/neu antibody-endostatin fusion proteins or controls. Briefly, tumor cells were plated out at $2-5\times10^3$ cells/well on 96 well plates and allowed to adhere overnight. The following day tumor cells were treated with various concentrations of endostatin fusion proteins or control, and incubated for a further 48-72 hours. To determine cell growth, 20 µl of 10 µg/ml MTT (3-(4,4-dimethylthiazol-2-yl)-2,5-diphenyl tetrazolium bromide; Sigma) was added to each well and the plates were incubated at 37° C. in 5% $CO_2$ for a further three hours. The supernatant was removed and the formed crystals dissolved in 200 µl dimethyl sulphoxide. The plates were then quantitated by determining their absorbance at 595 to 600 nm in a microplate reader. Growth inhibition was calculated by expressing the differences in optical densities between treatment wells and control wells as a percentage of the control. Each assay was performed in triplicate.

Effect on VEGF Secretion:

The following cell lines were tested for effects of anti-HER2/neu IgG3 control and/or endostatin, and for identifying informative cell lines that responded to endostatin, anti-HER2/neu antibody, or both proteins. To investigate effect of anti-HER2/neu antibody-endostatin fusion proteins on VEGF family expression, tumor cells such as SK-BR-3, BT474, MCF7 and MCF7-HER2, CT26 and CT-HER2/neu, or EMT6 and EMT6-HER2/neu were treated with anti-HER2/neu antibody-endostatin fusion proteins. $5 \times 10^5$ tumor cells/well were seeded in 24-well plates (Falcon). Cells were allowed to adhere overnight, and then treated with different concentrations (0.1, 1, 10, 100 µg/ml) of endostatin fusion proteins, endostatin, or antibody. Cells were removed by centrifugation at different time points (24, 48, 96 hours), and the supernatants filtered using a 0.22-µm pore size filter. Secreted VEGF levels were analyzed by a sandwich ELISA (R&D Systems, Minneapolis, Minn., USA) that detected all VEGF spliced forms. Human recombinant VEGF165 (R&D Systems, Minneapolis, Minn., USA) served as the standard.

Endothelial Cell Proliferation Assay:

The antiproliferative effect of anti-HER2/neu antibody-endostatin fusion proteins were tested using C-PAE cells. The cells were plated in 24-well fibronectin (10 µg/ml)-coated plates at 12,500 cells/well in 0.5 ml of DMEM containing 2% FBS. After a 24-h incubation at 37° C., the medium was replaced with fresh DMEM and 2% FBS containing 3 ng/ml of bFGF (R & D systems, Minneapolis, Minn., USA) with or without endostatin fusion proteins and endostatin (1, 10, or 100 µg/ml). The cells were pulsed with 1 µCi of [$^3$H]thymidine for 24 h. Medium was aspirated, cells were washed three times with PBS, and then solubilized by addition of 1.5 N NaOH (100 µl/well) and incubated at 37° C. for 30 min. Cell-associated radioactivity was determined with a liquid scintillation counter.

Migration Assay:

To determine the ability of anti-HER2/neu antibody-endostatin fusion proteins to block migration of human endothelial cells (ECV304) toward bFGF, a migration assay was performed using 12-well Boyden chemotaxis chambers (Neuro Probe, Inc.) with a polycarbonate membrane (25× 80-mm, PVD free, 8-µm pores; Poretics Corp., Livermore, Calif.). The nonspecific binding of growth factor to the chambers was prevented by coating the chambers with a solution containing 0.5% gelatin, 1 mM $CaCl_2$, and 150 mM NaCl at 37° C. overnight. ECV304 cells were grown in 10% FBS containing 5 ng/ml 1,1'-dioctadecyl-3,3,3',3'-tetramethylindocarbocyanine perchlorate (DiIC18; Molecular Probes, Eugene, Oreg.) overnight and washed with PBS containing 0.5% BSA. After trypsinization, the cells were counted and diluted to 300,000 cells/ml in medium containing 0.5% FBS. The lower chamber was filled with medium containing 25 ng/ml bFGF. The upper chamber was seeded with 15,000 cells/well with different concentrations of endostatin fusion protein (1, 10, 100 µg/ml). Cells were allowed to migrate for 4 h at 37° C. At that time, the cells on the upper surface of the membrane were removed with a cell scraper, and the (migrated) cells on the lower surface are fixed in 3% formaldehyde and washed in PBS. Images of the fixed membrane were obtained using fluorescence microscopy at 550 nM with a digital camera, and the number of cells on each membrane is determined.

In vitro Matrigel Assay:

Capillary tube formation assay in Matrigel is a useful in vitro assay to determine the branching morphogenesis of endothelial cells, which is a complex developmental program that regulates the formation of the blood vessels. Matrigel (Becton Dickinson, Franklin Lakes, N.J.) was used to coat a 24-well plate at 4° C. and allowed to polymerize at 37° C. for 30 min. HUVECs are seeded ($5 \times 10^4$ cells/well) on Matrigel-coated plates. Cells were incubated with VEGF (15 ng/ml) with or without endostatin fusion proteins or endostatin (1, 10, 100 µg/ml) in endothelial cell basal medium containing 2% FBS. After cells were incubated for 24 hrs or 96 hrs at 37° C., capillary tube formation was examined visually under a phase-contrast microscope and photographed. The intact tube number in six random views of .times.100 magnification was counted.

Apoptotic Activities of Anti-HER2/neu Antibody-Endostatin Fusion Protein:

To analyze the mechanism of endostatin fusion protein action on endothelial cells and nonendothelial cells, C-PAE cells or HUVECs were tested for apoptosis by measuring annexin V-FITC staining with FACS and terminal deoxynucleotidyl transferase-mediated dUTP nick-end labeling assay (TUNEL staining). As addition of endostatin lead to a reduction in the antiapoptotic proteins Bcl-2 and Bcl-XL, expression of these antiapoptotic proteins in the presence of anti-HER2/neu antibody-endostatin fusion proteins were monitored by Western blot analysis.

Annexin V-FITC Staining Assay:

Annexin V, a calcium-dependent phospholipid-binding protein with a high affinity for phosphatidylserine (PS) was used to detect early stage apoptosis. C-PAE cells or HUVECs ($2 \times 10^5$) were plated onto a fibronectin-coated 6-well plate in DMEM containing 2% FCS and 3 ng/ml b-FGF. Different concentrations (1-100 µg/ml) of antibody-endostatin fusion proteins, control antibodies, or endostatin were added to each well, and cells were harvested and processed 18 h after treatment. For the time course study, 10 µg/ml antibody-endostatin fusion proteins, control antibodies, or endostatin were added and cells were processed after 3, 4, 6, 12, and 18 h. Human recombinant TNF-α (40 ng/ml) was used as a positive control. The cells were washed in PBS and resuspended in binding buffer (10 mM HEPES/NaOH, pH 7.4, 140 mM NaCl, 2.5 mM $CaCl_2$). Annexin V-FITC was added to a final concentration of 100 ng/ml, and the cells were incubated in the dark for 10 min, then washed again in PBS and resuspended in 300 µl of binding buffer. 10 µl of propidium iodide (PI) was added to each sample before flow cytometric analysis. The cells are analyzed using a Becton Dickinson FACStar plus flow cytometer. In each sample, a minimum of 10,000 cells were counted and stored in list-mode. Data analysis was performed with standard Cell Quest software (Becton-Dickinson).

Microscopic Detection of TUNEL Staining:

C-PAE cells or HUVECs were seeded at a density of 5,000 cells/well on fibronectin-coated (10 µg/ml) Lab-Tek chamber slides and grown in 0.4 ml of DMEM with 10% FCS. After 2 days, the old medium was aspirated and fresh DMEM with 2% FCS was added, and the cells were starved overnight. The following day, 0.36 ml of new medium (with 2% FCS) containing 3 ng/ml b-FGF were added along with antibody-endostatin fusion proteins, control antibodies, or endostatin (10 µg/ml) or TNF-α (20 ng/ml). For control samples, fresh medium (2% FCS) containing bFGF (3 ng/ml) was added. Following induction (24 h), the slides were washed twice with PBS, and subsequently fixed in fresh 4% formaldehyde/PBS at 4° C. for 25 min. The slides were washed in PBS and the cells permeabilized in 0.2% Triton X-100/PBS for 5 min on ice, then washed with fresh PBS twice for 5 min each at room temperature, and the TUNEL assay was performed as described in the ApoAlert DNA fragmentation assay kit (CLONTECH), except that the final concentration of propidium iodide (Sigma) used was 1 µg/ml. After the assay, a drop of anti-fade solution is added, and the treated portion of the slide was covered with a glass coverslip with the edges sealed with clear nail polish. Slides were viewed immediately under a fluorescent microscope using a dual filter set for green (520 nm) and red fluorescence (>620 nm). The images were captured using a digital camera. Images are imported into NHImage 1.59, and measurements of fluorescence intensity are obtained as positive pixels. For all samples except the positive control (TNF-α: 5 fields), 15 random fields were chosen, and the number of green and red cells per field were counted.

Western Blotting Analysis of Expression of Antiapoptotic Proteins, Bcl-2 or Bcl-XL:

C-PAE cells and HUVECs ($1 \times 10^6$) were seeded in 10-cm Petri dishes precoated with fibronectin (10 µg/ml) in the presence of 2% FCS containing 3 ng/ml b-FGF. Antibody-endostatin fusion proteins, control antibodies, or endostatin were added at 10 µg/ml, and cells were harvested at 12, 24, and 48 h after treatment. Cells are washed three times in PBS buffer, pH 7.4, and the cells are resuspended in 1 ml of 1×EBC buffer (50 mM Tris-HCl, pH 8.0, 120 mM NaCl, 1% Nonidet P-40) containing freshly added complete protease inhibitor tablet (Boehringer Mannheim), 100 µg/ml Pefabloc, 1 µg/ml pepstatin. The protein concentration in whole cell lysate was measured by the bicinchoninic acid (BCA) method (Pierce). 30 µg of whole cell extract was loaded onto a 4-15% gradient polyacrylamide gel. Transfer was performed using a semi-dry transblot apparatus (Bio-Rad). The membrane was blocked in wash buffer (1× Tris-buffered saline) with 5% nonfat dry milk and incubated at 37° C. for 1 h. Goat antibody against human Bcl-2 and mouse polyclonal antibody against Bax and Bcl-XL (Santa Cruz Biotechnology, Santa Cruz, Calif.) were used as primary antibodies. Polyclonal anti-actin antibody (Sigma) was used to normalize for protein loading. Secondary antibodies were anti-goat, mouse and rabbit immunoglobulin conjugated to HRP (Amersham Pharmacia Biotech). The immunoreactivity was detected with an enhanced chemiluminescence reagent (Pierce). Images were scanned using a flat bed scanner and quantitated by the NIH image 1.59 software. Normalization was calculated by dividing the Bcl-2 signal by that of actin within each experiment.

In vivo Evaluation of the Antiangiogenic Properties of Anti-HER2/neu Antibody-Endostatin:

For in vivo antiangiogenesis, effects of the fusion were tested in Matrigel angiogenesis model in mice using VEGGF or VEGF with endostatin fusion proteins or endostatin alone. BALB/c mice (6-8 wk, n=3) were subcutaneously injected with 0.5 ml Matrigel (9-10 mg/ml) containing 150 ng/ml VEGF, with or without endostatin fusion proteins, antibody or endostatin (1 to 100 µg/ml), near the abdominal midline by using a 26-gauge needle. One week after Matrigel injection, mice were sacrificed, and the Matrigel plug, along with overlying skin and peritoneal membrane, was removed and fixed in 4% buffered formaldehyde in PBS. Plugs were embedded in paraffin, sectioned, and stained by incubation overnight at 4° C. with antibodies (DAKO Corporation, Carpenteria, Calif.) for endothelium-specific antigens such as PECAM (CD31) and proliferation cell nuclear antigen (PCNA) or Ki67 (MIB-1) to access endothelial cell proliferation. Thereafter, sections were treated with biotinylated antibody (ABC kit) for 40-45 min at room temperature, followed by a 45-min incubation with the avidin-biotin-peroxidase complex (ABC kit). The antigen-antibody complex was visualized by incubation with freshly prepared 3,3'-diaminobenzidine (DAB kit, Vector Laboratories). Sections were counterstained with hematoxylin-eosin. Ten fields were randomly selected using a microscope at 400× magnification, and photographed using a digital camera. The number of PECAM-1-positive, PCNA-positive, Ki67-positive cells were counted.

Antiangiogenic Activity of Anti-HER2/neu Antibody-Endostatins in Tumors by Immunohistochemical Staining:

BALB/c or BALB/c BCDM were injected s.c. in the flank region with 106 EMT6-HER2/neu or CT26-HER2/neu cells on the right flank and control 106 EMT6 or CT26 on the left flank, respectively. In addition, SCID mice were injected s.c. in the flank region with 106 MCF7-HER2/neu, SK-BR-3, or BT474 cells on the right flank and control 106 MCF7 on the left flank.

On the seventh day, mice were injected i.v. with the antibody-endostatin fusion proteins (42 µg), equimolar control antibodies (34 µg) or equimolar endostatin (8 µg). This treatment was repeated 7 times every other day. Visible tumors, along with overlying skin and surrounding tissue, were removed at various time points (2 days, 8 days, 16 days after treatments, 3 mice/time point), and tissue sections are immunohistochemically stained with mouse antibody specific for endothelium-specific antigens such as PECAM (CD31, DAKO Corporation, Carpenteria, Calif.), and doubly stain tissue with mouse antibody specific for proliferation cell nuclear antigen (PCNA, DAKO Corporation, Carpenteria, Calif.) or Ki67 (MIB-1, DAKO Corporation, Carpenteria, Calif.) to access endothelial cell proliferation.

Tissue sections were fixed in 4% paraformaldehyde/PBS pH 7.4, dipped in a quenching solution (3% hydrogen peroxide/60% methanol) to remove endoperoxidase activity, and then placed in 10% normal blocking serum (ABC kit, Vector Laboratories, Inc., Burlingame, Calif.) for 20 min before incubation overnight at 4° C. with mouse antibody for PECAM-1, Ki67, or PCNA, or with mouse IgG as the control. Thereafter, tissue sections were treated with biotinylated antibody (ABC kit) for 40-45 min at room temperature, followed by a 45-min incubation with the avidin-biotin-peroxidase complex (ABC kit). The antigen-antibody complex was visualized by incubation with freshly prepared 3,3'-diaminobenzidine (DAB kit, Vector Laboratories), and the tissue was counterstained with hematoxylin. Ten fields were randomly selected using a microscope at 400× magnification, and photographed using a digital camera. The number of PECAM-1-positive, PCNA-positive, Ki67-positive cells are counted.

Antiangiogenic Activity of Anti-HER2/neu Antibody-Endostatin on VEGF Expression and Neovascularization in Tumors:

Anti-tumor activity of endostatin was associated with a down-regulation of VEGF expression. The experiment shown above was repeated in human breast cancer xenografts (SK-BR-3, BT474, MCF7 and MCF7-HER2) in SCID mice (n=3) to evaluate antiangiogenic activity of the antibody-endostatin fusion proteins (42 μg), equimolar control antibodies (34 μg) or equimolar endostatin (8 μg). This treatment was repeated 7 times every other day. Visible tumors, along with overlying skin and surrounding tissue, were removed at various time points (2 days, 8 days, 16 days after treatments, 3 mice/time point). Tissues were stained for endothelial cell proliferation using PCNA or Ki67 as described above, and the tissue sections were also stained with specific antibodies (VEGF-A, Neomarker; VEGF-C and VEGF-D, Santa Cruz Biotechnology, Santa Cruz, Calif.) for VEGF family.

Serum was collected at various times (before treatment, 2 days, 8 days, 16 days after treatments) for VEGF ELISA (R&D Systems, MN) to measure antiangiogenic abilities of endostatin fusion proteins as described above. In disease states, VEGF can be detected in various tumor cells and five different VEGF isoforms, with 121, 145, 165, 189, and 206 amino acids, can be generated as a result of alternative splicing from the single VEGF gene. These isoforms differ in their molecular mass and in their biological properties, such as their ability to bind to heparin or heparan-sulphate proteoglycans and to different VEGF receptors (VEGFRs). The splice forms $VEGF_{121}$, $VEGF_{145}$, and $VEGF_{165}$ are secreted, whereas $VEGF_{189}$ is tightly bound to cell surface heparan-sulphate and $VEGF_{206}$ is an integral membrane protein. In contrast to the other forms, $VEGF_{121}$, does not bind to heparin or extracellular matrix proteoglycans. he signaling tyrosine kinase receptors VEGFR-1 (flt-1, fms-like tyrosine kinase 1) bind $VEGF_{121}$ and $VEGF_{165}$, and VEGFR-2 (KDR, kinase domain region/flk-1, fetal liver kinase 1) additionally $VEGF_{145}$ (apart from certain VEGF-related peptides).

mRNA expression of VEGF isoforms was determined in excised tumors by RT-PCR. For RT-PCR, frozen samples (1 g) were crushed in an achate mortar under liquid nitrogen; RNA was isolated by the phenol-guanidinium thiocyanate method and purified by isopropanol and repeated ethanol precipitation; and contaminating DNA was destroyed by digestion with RNase-free DNase 1 (20 min at 25° C.). After inactivation of the DNase (15 min at 65° C.), cDNA was generated with 1 μl (20 pmol) of oligo (dT)15 primer (Amersham) and 0.8 μl of superscript RNase H-reverse transcriptase (Gibco) for 60 min at 37° C. For PCR, 4 μl of cDNA was incubated with 30.5 μl of water, 4 μl of 25 mM $MgCl_2$, I PI of dNTP, 5 μl of 10×PCR buffer, 0.5 μl (2.5 U) of platinum Taq DNA polymerase (Gibco), and the following primers (2.5 μl each containing 10 pmol): non-selective for all VEGF splice variants 5'-ATG-GCA-GAA-GGG-CAG-CAT-3' (sense) (SEQ ID NO: 3) and 5'-TTG-GTG-AGG-TTT-GAT-CCG-CAT-CAT3' (antisense) (SEQ ID NO: 4) yielding a 255 bp fragment (40 cycles, annealing temperature 55° C.); selective for VEGF splice variants 5'-CCA-TGA-ACT-TTC-TGC-TGT-CTT-3' (sense) (SEQ ID NO: 5) and 5'-TCG-ATC-GTT-CTG-TAT-CAG-TCT-3' (antisense) (SEQ ID NO: 6) yielding a different fragment size for each variant (40 cycles, annealing temperature 55° C.). With selective primers, the 526 bp product corresponds to $VEGF_{121}$, the 598 bp product to $VEGF_{145}$, the 658 bp product to $VEGF_{165}$, the 730 bp product corresponds to $VEGF_{189}$, and the 781 bp product corresponds to $VEGF_{206}$.

Example 1

Targeted Delivery of Anti-HER2 Antibody-Human Endostatin P125A Protein Results in Enhanced Anti-Tumor Efficacy in Murine and Human Breast Tumor Models Two anti-HER2 human endostatin fusion proteins were generated by fusing human wild type or a mutant form of human endostatin (huEndo-P125A) to the 3' end of a humanized anti-HER2 IgG3 antibody. HuEndo-P125A antibody fusion protein (αHER2-huEndo-P125A) inhibited VEGF and bFGF induced endothelial cell proliferation, and capillary formation in vitro, to a greater degree than wild type endostatin fusion protein (αHER2-huEndo), endostatin alone, or anti-HER2 antibody (αHER2 IgG3). Treatment of SKBR-3 breast cancer xenografts with anti-HER2 IgG3-huEndo-P125A fusion resulted in complete regression, and improved survival, compared to either αHER2 IgG3, human endostatin, or anti-HER2 IgG3-huEndo treated mice. αHER2-huEndo fusion proteins specifically targeted tumors expressing HER2 in mice simultaneously implanted with murine mammary tumor cell line EMT6 and EMT6 engineered to express HER2 antigen (EMT6-HER2). αHER2 huEndo-P125A fusion antibody showed enhanced anti-angiogenic and anti-tumor activity and inhibited EMT6-HER2 growth more effectively than huEndo (p=0.003), or αHER2-huEndo (p=0.004).

Materials and Methods

Cell Lines, Materials and Animals:

To produce a murine breast tumor expressing human HER2, the murine mammary tumor cell line EMT6 was transduced by use of a retroviral construct containing the cDNA encoding the human HER2 gene (EMT6-HER2). EMT6, EMT6-HER2, the human breast cancer cell line SK-BR-3, and transfected Sp2/0 or P3X63Ag8.653 cells were cultured in Iscove's modified Dulbecco's medium with 5% calf serum.

Human umbilical vein endothelial cells (HUVEC), were obtained from Clontech Lab, Inc. (Palo Alto, Calif.) and used between passages 3 and 5 and maintained in EGM2-MY medium (Clontech, Palo Alto, Calif.) that contained endothelial basal medium 2 (EBM-2), supplemented with 5% fetal bovine serum (FBS), gentamicin, amphotericin B, hydrocortisone, ascorbic acid, vascular endothelial growth factor (VEGF), basic fibroblast growth factor (bFGF), human epidermal growth factor, and insulin-like growth factor I.

Human recombinant endostatin was purchased from Sigma (E8154, St Louis, Mo.) and anti-CD31 antibody conjugated with biotin from BD Biosciences (Franklin Lakes, N.J.). Alexa Fluor 488 was obtained from Invitrogen (Carlsbad, Calif.), and DAPI from Molecular Probes (Carlsbad, Calif.).

Female BALB/c mice (4-6 weeks) and severe combined immunodeficient (SCID) mice (4-6 weeks) were purchased from The Jackson Laboratory (Bar Harbor, Me.) and used for in vivo tumor growth and xenograft experiments (SK-BR-3) as indicated. All experiments were conducted in compliance with the NIH Guides for the Care and Use of Laboratory Animals and approved by the University of Miami Institutional Animal Care and Use Committee.

Construction, expression, and characterization of αHER2-huEndo fusion protein:

The human endostatin (huEndo) gene was cloned from the human collagen, type XVIII, alpha 1 gene by PCR using primers 5'-CCCCTCGCGATATCACAGCCACCGCGACT-TCCAGCCG-3' (SEQ ID NO: 1) and 5'-CCCCGAAT-TCGTTAACCCTTGGAGGCAGTCATGAAGC-3' (SEQ ID NO: 2). PCR products were subcloned into pCR-Blunt II-TOPO vector and sequenced. A single-point mutant clone at a position 125 in wild-type human endostatin was derived by site-directed mutagenesis using PCR with phosphorylated primer, 5' p-GGCTCGGACGCCAACGGGCGC-3' (SEQ ID NO: 7). An alanine residue was substituted for proline at position 125 by site-directed mutagenesis. A point mutation in human endostatin at position 125 (proline to alanine; huEndo-P125A) has been reported to enhance endothelial cell binding and anti-angiogenic activity. The subcloned huEndo and huEndo-P125A genes were ligated in frame to the carboxyl end of the heavy chain constant domain of human IgG3 in the vector pAT135 (Shin S U, et al. *J Immunol* 1997; 158:4797-804). The endostatin heavy chain constant region was joined to the anti-HER2 variable region of a recombinant humanized monoclonal antibody 4D5-8 (trastuzumab; Genentech, San Francisco, Calif.) in the expression vector (pSV2-his) containing HisD gene for eukaryotic selection.

To obtain active endostatin fusion proteins, the αHER2-huEndo fusion constructs were stably transfected into SP2/0 or P3X63Ag8.653 myeloma cells expressing the anti-HER2 kappa light chain by electroporation as described previously (Shin S U, et al. *Methods Enzymol* 1989; 178:459-76). The αHER2-huEndo fusion proteins were biosynthetically labeled with [$^{35}$S]methionine (Amersham Biosciences, Piscataway, N.J.), immunoprecipitated using IgGSorb suspension (*S. aureus* cells), and analyzed by SDS-PAGE. The endostatin fusion proteins were purified from culture supernatants using protein A immobilized on Sepharose 4B fast flow (Sigma, St. Louis, Mo.) (Shin S U, et al. *Methods Enzymol* 1989; 178:459-76).

Flow Cytometry:

To detect the binding of αHER2-huEndo fusion proteins to HER2 antigen, human breast cancer cells, SK-BR-3, or murine mammary tumor cells, EMT6 and EMT6-HER2, were incubated at 4° C. with 1 μg/ml of endostatin fusion proteins, αHER2 IgG3, or isotype control. After 15 min the cells were washed with PBS containing 0.1% BSA and 0.05% NaN$_3$, and the bound fusion proteins were identified with either FITC conjugated anti-human IgG-, or the endostatin domain was recognized with biotinylated anti-human endostatin antibody and secondarily stained with a streptavidin-PE conjugate at 4° C. After incubation, the cells were washed twice and resuspended in 0.4 ml of PBS. FACScan flow cytometry was used for data acquisition. Background staining was estimated after incubation with the secondary FITC or PE labeled antibody alone.

Matrigel Tube Formation Assay:

The matrigel tube formation assay was performed in 48-well plates, as previously reported (Merchan J R, et al. *Int J Cancer* 2005; 113(3):490-8). Each well of pre-chilled 48-well cell culture plates was coated with 100 μl of unpolymerized Matrigel (7 mg/ml) and incubated at 37° C. for 30-45 minutes. HUVECs were harvested with trypsin, and 4×10$^4$ cells were resuspended in 300 μL of full endothelial cell growth medium (see above) and treated with endostatin, control antibody or the various αHER2-huEndo fusion proteins before plating onto the Matrigel-coated plates. After 16 hours of incubation, endothelial cell tube formation was assessed with an inverted photomicroscope, and microphotographs of the center of each well were taken at low power (40×). Tube formation by untreated HUVECs in full endothelial cell growth medium was used as a control.

HUVEC Proliferation Assay:

A total of 4×10$^3$ cells in 100 μl of the endothelial basal medium with 1% FBS, penicillin (100 U/ml), and streptomycin (100 μg/ml) were placed into each well of a 96-well plate, treated with αHER2-huEndo fusion proteins and controls, and incubated at 37° C. for 72 hours; control cells were cultured in basal medium, 1% FBS, and antibiotics, as above. VEGF (10 ng/ml) or bFGF (10 ng/ml) were added as stimulants of endothelial cell proliferation. After the 72-hour incubation, WST-1 (10 μl, Roche, Indianapolis, Ind.) was added to each well, and after a 3-hour incubation at 37° C., absorbance at 450 nm was determined for each well with a microplate reader (Bio-Rad Laboratories, Hercules, Calif.). Data presented are the average of triplicate experiments which were repeated twice.

In Vivo Tumor Growth Assays:

To evaluate anti-tumor activity of αHER2-huEndo fusion proteins SK-BR-3 cells (2×10$^6$ per mouse) were implanted s.c. in the flank of SCID mice. On day 5, mice (5 per group) were injected i.v. with equimolar amounts of purified αHER2-huEndo fusion proteins (42 μg), αHER2 IgG3 (34 μg), or human endostatin (8 μg). This treatment was repeated every other day for 13 doses. Tumor size was measured with calipers and growth rates were recorded and calculated using the following equation: tumor volume (mm$^3$)=4/3×3.14×{(long axis+short axis)/4}$^3$.

Murine mammary tumor EMT6 cells were transduced with a retroviral vector encoding human HER2 antigen as described previously (Cho H M, Rosenblatt J D, et al. *Mol Cancer Ther* 2005; 4(6):956-67). The EMT6-HER2 cells that were used in these studies proliferate at the same rate in vitro as parental EMT6 cells. The in vivo anti-tumor efficacy and specificity of αHER2-huEndo fusion proteins was examined using the EMT6 and EMT6-HER2 cell lines simultaneously implanted contralaterally in syngeneic BALB/c mice. To determine efficacy of αHER2-huEndo fusion proteins, BALB/c mice (3-8 per group, 4-6 weeks) were injected s.c. with 1×10$^6$ EMT6-HER2 cells in the right flank and/or control EMT6 cells in the left flank. On day 6, mice were injected i.v. with the αHER2-huEndo fusion proteins (42 μg/injection, 2×10$^{-10}$ mol, equimolar to 8 μg human endostatin), αHER2 IgG3 alone (34 μg/injection, 2×10$^{-10}$ mol), endostatin alone (8 μg/injection, 4×10$^{-10}$ mol), or PBS as a control. All mice received a total of eleven injections at 2-day intervals and tumor growth analyzed as described above.

Immunofluorescent Staining:

To investigate blood vessel formation in tumors treated with αHER2-huEndo-P125A fusion protein, EMT6 and EMT6-HER2 cell lines (1×10$^6$) were contralaterally implanted in syngeneic BALB/c mice (n=4) as described above. On day 4, mice were injected i.v. with αHER2-huEndo-P125A (42 μg/injection), or PBS as a control every two days. On day 12, two mice were sacrificed for analysis of vascularity after four treatments. On day 18, another two mice were sacrificed for analysis after seven treatments. Tumors were excised from the sacrificed mice and frozen in liquid nitrogen and the 8 μm frozen sections were prepared. The tumor sections were fixed with methanol for 10 min, washed with PBS 3 times, and incubated with blocking solution for 1 hour in a humidified chamber. Slides were then washed with PBS 3 times, for 10 min. For immunofluorescent staining, diluted primary antibodies (anti-CD31 antibody conjugated with biotin: 1:200) in PBS were added to each slide. After incubation at room temperature overnight, the sections were incubated with diluted secondary antibodies conjugated with Alexa Fluor 488 (1:500) with PBS, and then with diluted DAPI (1:5000) in a humidified chamber and mounted with Gel mounting media (Biomeda Corp. Foster City, Calif.). The stained images were analyzed with a Zeiss microscope. The digital tumor images from each treatment were measured as blood vessel area (pixel) and averaged to measure blood vessel density per tumor (n=5). Images were analyzed using NIH ImageJ software by color to form a binary image of the tumor blood vessels.

Statistical Analysis:

Statistical analysis was carried out with Graphpad Prism 4 (GraphPad Software, Inc. La Jolla, Calif.). HUVEC proliferation and anti-tumor efficacy in human breast cancer SK-BR-3 xenografts were analyzed by two-way repeated measures (RM) analyses of variance (ANOVA), followed by Bonferroni posttest. On Day 16, anti-tumor efficacy in murine syngeneic tumor model was analyzed by Student's t test (unpaired, two-tailed) within each treatment group, and was analyzed among three different treatments by one-way ANOVA, followed by Bonferroni's multiple comparison test. Blood vessel density was analyzed by Student's t test (unpaired, two-tailed) within each category. Graphs were expressed as the mean values with 95% confidence interval (CI). Differences were considered statistically significant at $P<0.05$.

Results:

Construction and Purification of αHER2-huEndo Fusion Proteins:

We previously demonstrated enhanced anti-tumor activity of an anti-HER2 antibody-mEndo fusion protein, relative to that seen with anti-HER2 antibody and/or murine endostatin delivered alone or in combination. In preparation for potential human use and an effort to reduce antigenicity, the fusion protein was "humanized" through substitution of human endostatin sequences for the murine endostatin fusion domain. The human endostatin (huEndo) gene was cloned from the human collagen, type XVIII, alpha 1 gene by PCR. Clones containing wild-type human endostatin were identified. A point mutation in human endostatin at position 125 (proline to alanine; huEndo-P125A) within a previously mapped angiogenic domain of endostatin had increased endothelial cell binding and enhanced anti-angiogenic activity. A P125A mutation was introduced into human endostatin using site directed mutagenesis. The subcloned huEndo and huEndo-P125A genes were ligated in frame to the carboxyl end of the heavy chain constant domain of human IgG3 and the endostatin heavy chain constant region was then joined to the anti-HER2 variable region derived from the humanized monoclonal antibody 4D5-8 (HER2, trastuzumab; Genentech) in the expression vector (pSV2-his) containing HisD gene for eukaryotic selection. A schematic of the resulting fusion proteins is shown in FIG. 1A.

The anti-HER2 IgG3-huEndo fusion protein constructs were then stably transfected into SP2/0 or P3X63Ag8.653 myeloma cells stably expressing the anti-HER2 kappa light chain in order to assemble the entire anti-HER2 IgG3-huEndo fusion proteins, anti-HER2 IgG3-huEndo (αHER2-huEndo) and anti-HER2 IgG3-huEndo-P125A (αHER2-huEndo-P125A) (FIG. 1A). The αHER2-huEndo fusion proteins were biosynthetically labeled with [$^{35}$S]methionine and analyzed by SDS-PAGE. αHER2-huEndo fusion proteins of the expected molecular weight were secreted as the fully assembled $H_2L_2$ form (FIG. 1B). The secreted [$^{35}$S]methionine-labeled proteins had a molecular weight of ~220 kDa under non-reducing conditions, the size expected for a complete antibody (170 kDa) with two molecules of endostatin (25 kDa each) attached (FIG. 1A). Following reduction, heavy and light chains of the expected molecular weight were observed (85 kDa and 25 kDa, respectively) (FIG. 1B). The endostatin fusion proteins were then purified from culture supernatants using a protein A column.

Binding Ability of Anti-HER2 Human Endostatin Fusion Proteins to HER2 Target Antigen and to HUVECs:

An investigation of whether the endostatin fusion proteins could recognize the HER2 antigen was conducted (FIG. 2). The HER2 expressing human breast cancer cell line, SK-BR-3, and murine mammary tumor cells, EMT6 and EMT6-HER2 were used to test binding to HER2 antigen, using anti-human IgG antibody as a detection antibody, αHER2 IgG3, αHER2-huEndo and αHER2-huEndo-P125A, bound to the HER2+ SKBR3 breast cancer cells and EMT6-HER2 cells (FIGS. 2A and 2B, respectively), while the isotype control antibody (anti-dansyl IgG3) did not bind to SK-BR-3 and EMT6-HER2. αHER2 IgG3, αHER2-huEndo or αHER2-huEndo-P125A did not bind to parental EMT6 cells that did not express any HER2 antigen (FIG. 2C).

To investigate structural integrity of the human endostatin moiety of the fusion proteins, anti-HER2 human endostatin fusion proteins were incubated with SK-BR-3, EMT6-HER2 and EMT6. The human endostatin domain of fusion proteins bound to SK-BR-3 and EMT6-HER2 was detected with biotinylated anti-human endostatin and stained with streptavidin-PE conjugate. αHER2-huEndo and αHER2-huEndo-P125A were both recognized following binding to SK-BR-3 and EMT6-HER2 by the anti-human endostatin detection antibody (FIGS. 2D and 2E), while αHER2 IgG3 and the isotype control antibodies were not detected. Endostatin could be detected using either αHER2-huEndo or αHER2-huEndo-P125A as the primary antibody and both fusion proteins bound to HER2+SK-BR-3 and EMT6-HER2 cells with similar affinity.

To determine whether αHER2-huEndo fusion proteins could bind to endothelial cells, HUVECs were treated with αHER2 IgG3, huEndo, or αHER2-huEndo fusion proteins, and human endostatin domain bound to HUVECs was detected with biotinylated anti-human endostatin and stained with streptavidin-PE conjugate. Binding of human endostatin and αHER2-huEndo fusion proteins to HUVECs was readily detected, while the isotype control, or αHER2 IgG3 binding was not detected (FIG. 2F). Of note αHER2-huEndo-P125A showed slightly greater binding to HUVECs relative to either human endostatin or αHER2-huEndo.

Figure 3A:
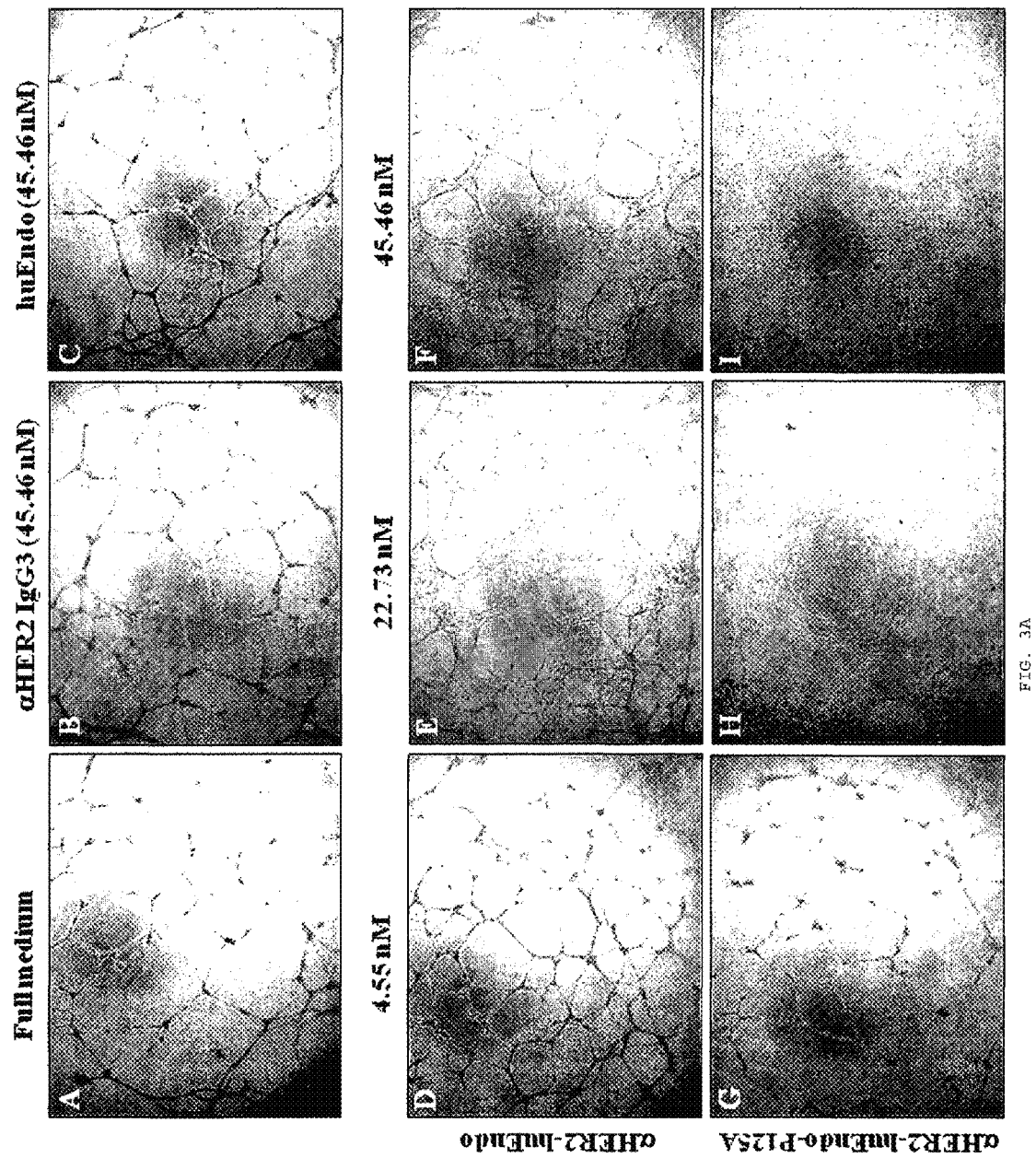
FIGS. 3A and 3B show the effects of anti-HER2 IgG3-huEndo fusion proteins on EC tube formation and EC proliferation.

Inhibition of Endothelial Tube Formation by the αHER2-huEndo Fusion Proteins:

To evaluate anti-angiogenic properties of the human endostatin antibody fusion proteins, the effects of the αHER2-huEndo fusion proteins were tested in an in vitro angiogenesis assay in which human endothelial cells are plated on Matrigel, and spontaneously aggregate and assemble into multicellular capillary-like tubular structures in response to vascular stimuli (e.g. bFGF, VEGF, FBS). Neither parental antibody nor human endostatin alone showed appreciable inhibition of tube formation. In contrast, αHER2-huEndo fusion protein treatment strongly inhibited assembly into tubular structures, with cells remaining dispersed and exhibiting a morphology resembling adherent cells on plastic (scattered phenotype) in a dose dependent fashion (FIG. 3A). The αHER2-huEndo and αHER2-huEndo-P125A fusion proteins (FIGS. 3A(D-I)) showed significantly greater inhibition of HUVEC tube formation compared to αHER2 IgG3 (FIG. 3A(B)) or to human endostatin (FIG. 3A(C)). The increased in vitro anti-angiogenic effect of αHER2-huEndo fusions relative to native endostatin may be due to presentation of endostatin as a dimer.

Inhibition of tubule assembly seen with αHER2-huEndo-P125A (FIGS. 3A(G-I)) was significantly greater than that seen for αHER2-huEndo (FIGS. 3A(D-F)) at comparable concentrations and treatment of HUVEC at 45 nM resulted in complete disruption of tubule formation and extensive morphologic changes (scatter) (FIGS. 3A(H-I)). Mutation of proline to alanine at amino acid position 125 of human endostatin in the fusion protein therefore increased inhibition of tubule formation by endothelial cells compared to either native endostatin (huEndo, FIG. 3A(C)) or wild type endostatin fusion protein αHER2-huEndo (FIGS. 3A(D-F)).

Figure 3B:
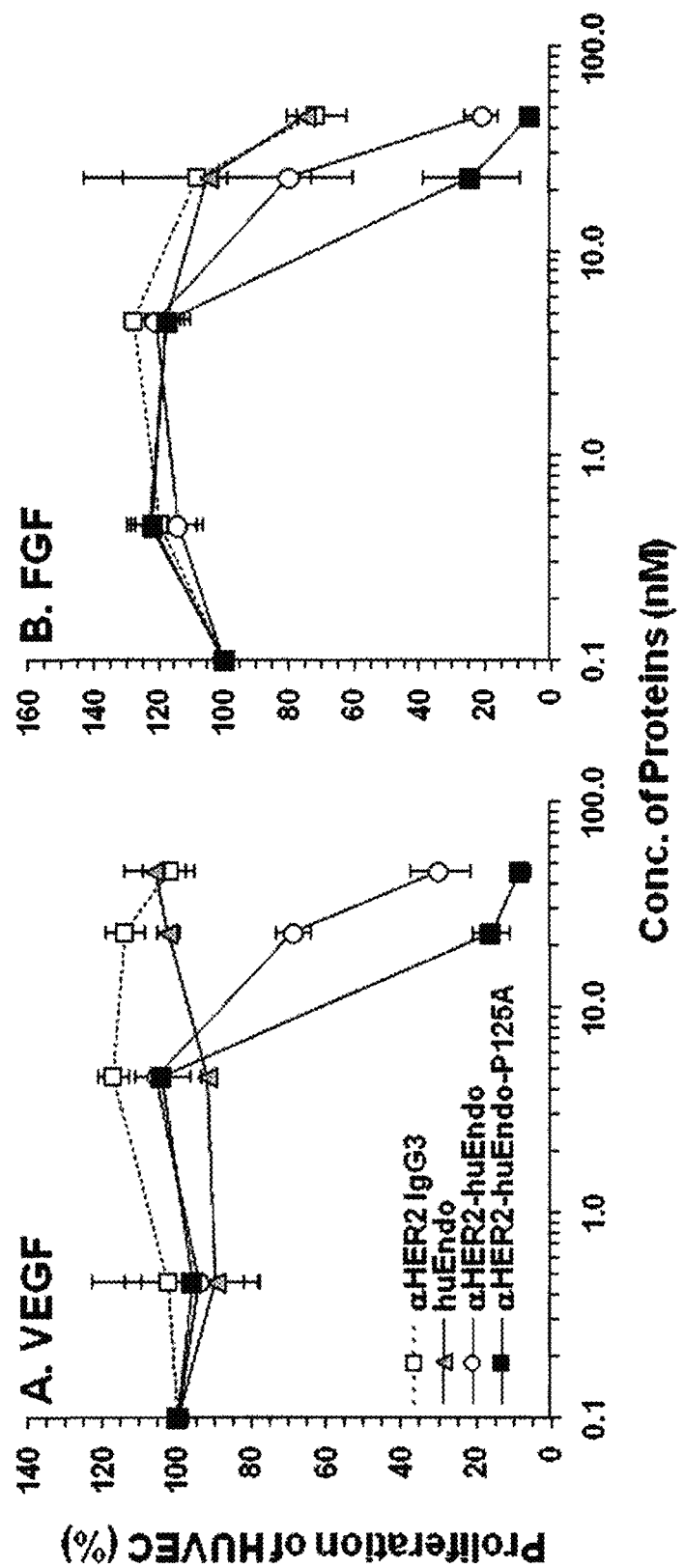

Proliferation of Endothelial Cells by the αHER2-huEndo Fusion Proteins:

The effects of αHER2-huEndo fusion proteins were assessed on endothelial cell (EC) proliferation. HUVECs were exposed to increasing concentrations of the fusion proteins for 72 hrs in the absence or presence of either VEGF or bFGF. Both wild type and mutant antibody-endostatin fusion proteins markedly inhibited endothelial cell proliferation induced by either VEGF (FIG. 3B(A)) or bFGF (FIG. 3B(B)). HUVEC proliferation was more effectively inhibited by αHER2-huEndo-P125A at comparable concentrations than by αHER2-huEndo (p=0.0085 at the presence of VEGF, p=0.0034 at the presence of bFGF) or by endostatin alone (p=0.0003 at the presence of VEGF or bFGF) (FIG. 3B).

Figure 4A:
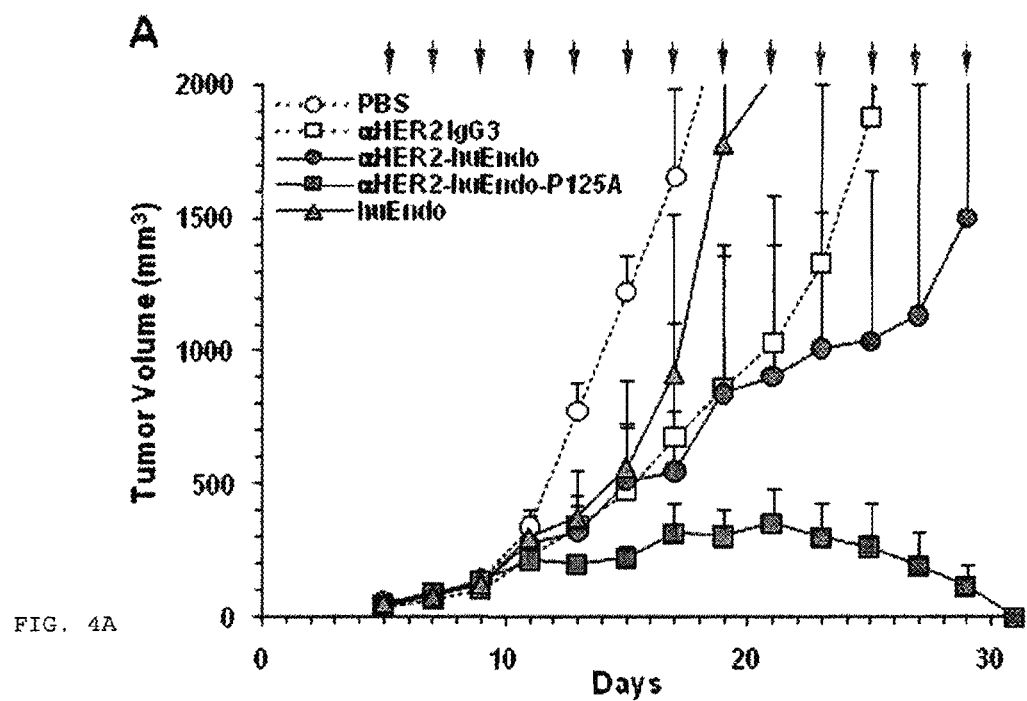
FIGS. 4A and 4B are graphs showing the anti-tumor efficacy of anti-HER2 IgG3-huEndo fusion proteins. SCID mice (n=5) were s.c. inoculated with $2 \times 10^6$ SK-BR-3 on the right flank back on day 0, then the mice were i.v. injected with anti-HER2 IgG3-huEndo fusion proteins (42 μg), anti-HER2 IgG3 (34.9 μg), human endostatin (8 μg), or PBS every other day (indicated with arrow starting on day 5).

Anti-Tumor Efficacy in Human Breast Cancer SK-BR-3 Xenografts:

SK-BR-3 is a HER2-amplified human breast cancer cell line which grows slowly in SCID mice. Trastuzumab, anti-HER2 IgG1, is able to inhibit the growth of human breast cancer SK-BR-3 overexpressing HER2 alone or in combination with chemotherapy. Anti-tumor activity of αHER2-huEndo fusion proteins was assayed against human breast cancer SK-BR-3 xenografts in SCID mice. A representative experiment is shown in FIG. 4. Equimolar doses of protein were injected every other day for 4 weeks (FIG. 4). In FIG. 4A, endostatin and αHER2 IgG3 did not significantly inhibit tumor growth relative to the non-treated group (PBS, p value=0.1504) by day 29, and αHER2 IgG3 very significantly inhibited tumor growth relative to the non-treated group (PBS, p=0.0045), while treatment with αHER2-huEndo and αHER2-huEndo-P125A resulted in markedly greater inhibition of growth (p<0.0001, respectively). Mice treated with αHER2-huEndo-P125A significantly enhanced inhibition of tumor growth compared to those treated with αHER2-huEndo (p=0.0161), human endostatin (p=0.0343), or αHER2 IgG3 (p=0.0253) (FIG. 4A). There was no significant difference in inhibition of growth among the treatments with αHER2-huEndo, human endostatin, or αHER2 IgG3.

Figure 4B:
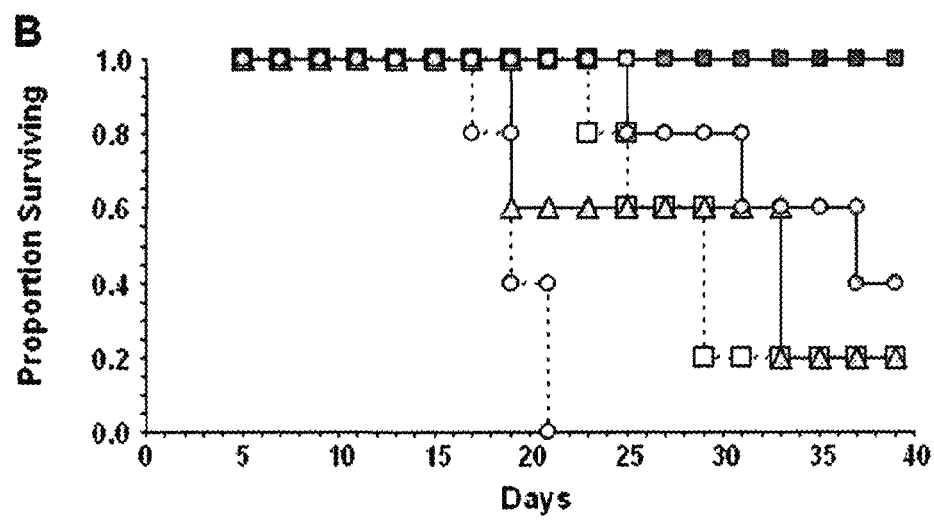

Treatment with αHER2-huEndo-P125A completely eradicated tumors after 30 days and showed the highest degree of inhibition. The proportion of tumor-free survivors was higher for the αHER2-huEndo-P125A group (5 of 5 in the experiment shown compared to PBS (0 of 5), αHER2 IgG3 and human endostatin (1 of 5), and αHER2-huEndo (2 of 5) (FIG. 4B). Mice treated with αHER2-huEndo-P125A showed improved survival relative to those treated with αHER2-huEndo, human endostatin alone, or αHER2 IgG3 alone (FIG. 4B). Similar results were seen in the duplicated experiment of which a representative experiment is shown.

Figures 5A, 5B, 5C, 5D, 5E, 5F:
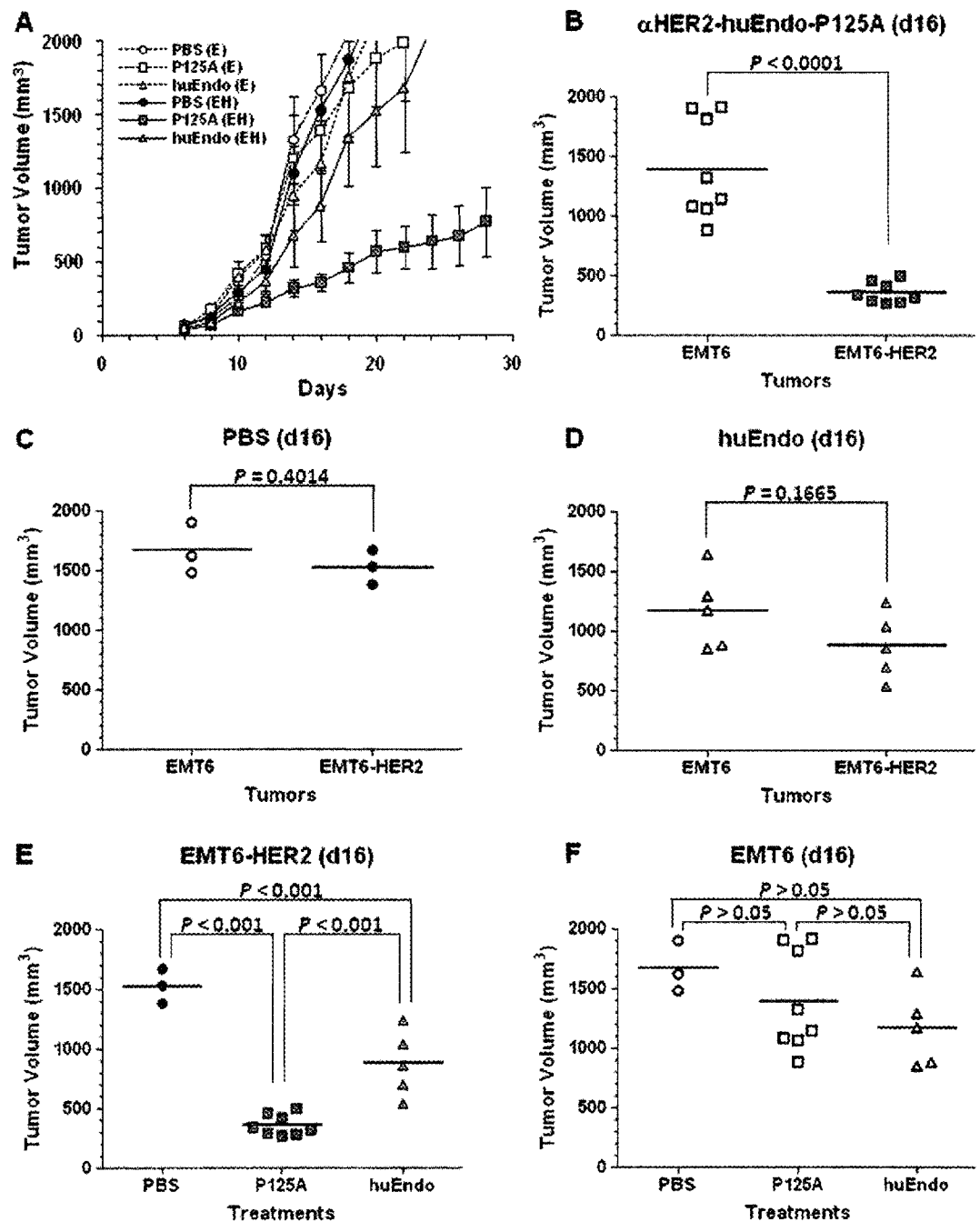
FIGS. 5A to 5F are graphs showing anti-tumor activity of αHER2-huEndo fusion-P125A protein in a syngeneic mouse model. BALB/c mice (n=3-8 per group) were implanted s.c. contralaterally with EMT6 (I-III) and EMT6-HER2 (IV-VI) ($1 \times 10^6$ cells per mouse), followed on day 6 by equimolar injections every other day (11 times) of αHER2-huEndo-P125A (42 μg), human endostatin (8 μg), or PBS.

Anti-Tumor Efficacy Requires Presence of the HER2 Target:

To investigate whether the ability of αHER2-huEndo-P125A fusion protein to specifically target HER2 expressing tumors enhanced efficacy, BALB/c mice were simultaneously implanted with EMT6 and EMT6-HER2 tumors on opposite flanks. Mice were then treated with either αHER2-huEndo-P125A or human endostatin. Equimolar administration of αHER2-huEndo-P125A to mice showed preferential growth inhibition of EMT6-HER2 on day 16, when compared to parental EMT6 implanted on the contralateral flank (FIG. 5A, mean tumor volume of EMT6=1391 mm$^3$, mean tumor volume of EMT6-HER2=360 8 mm$^3$, difference between mean tumor volumes=1030±152.1, 95% CI=703.6 to 1356, p<0.0001). PBS (FIG. 5CA, mean tumor volume of EMT6=1677 mm$^3$, mean tumor volume of EMT6-HER2=1527 mm$^3$, difference between mean tumor volumes=140.7±150.0, 95% CI=−275.7 to 150.0, p=0.4014) and endostatin (FIG. 5D, mean tumor volume of EMT6=1169 mm$^3$, mean tumor volume of EMT6-HER2=877 8 mm$^3$, difference between mean tumor volumes=291.1±191.3, 95% CI=−150.0 to 732.2, p=0.1665) showed no significant difference on preferential inhibition of EMT6-HER2 and EMT6 tumors. Among three different treatments, αHER2-huEndo-P125A (FIG. 5E, p<0.001) inhibited EMT6-HER2 tumor growth more effectively than PBS (FIG. 5E, p<0.001 A), or endostatin (p<0.001,) on day 16. However, there was no significant difference on inhibition of HER2 negative EMT6 parental tumor among the treatments (FIG. 5F, p>0.05). Selective targeting of HER2 expressing tumor was therefore required for maximum efficacy.

Figure 6:
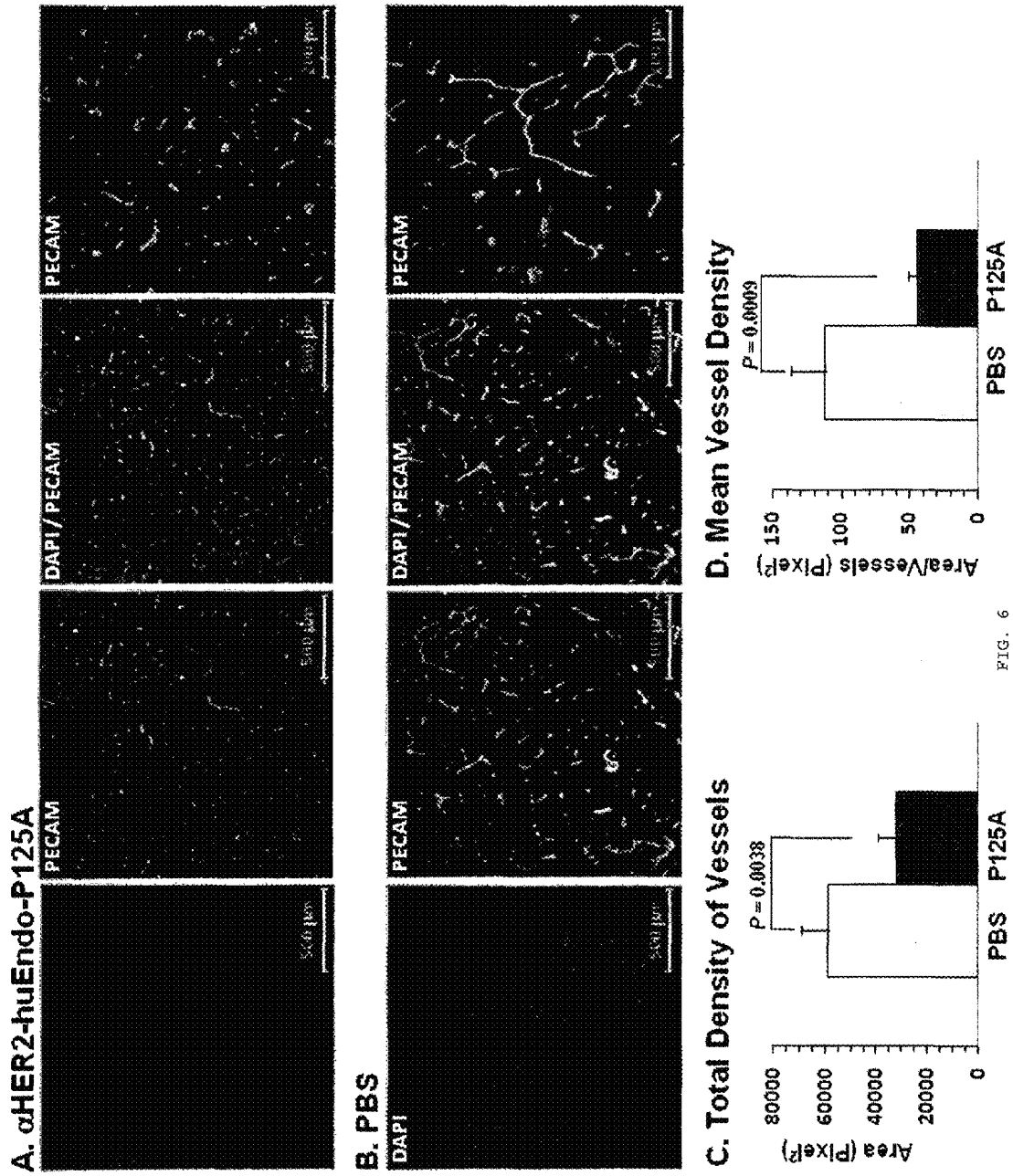
FIG. 6 shows the analysis of tumor vascularity. BALB/c mice (n=4 per group) were implanted s.c. contralaterally with EMT6 and EMT6-HER2 ($1 \times 10^6$ cells per mouse), followed on day 4 by equimolar injections every other day (7 time treatments) of αHER2-huEndo-P125A (42 μg), or PBS. On day 12, two mice were sacrificed for the blood vessel analysis after four treatments. Histologic sections of tumors from the sacrificed mice were analyzed using immunofluorescent staining for PECAM (II-IV, VI-VIII; green color). DAPI (I, III, V, VII; blue color) was used for counter-staining of the nucleus. Representative immunofluorescent staining of EMT6-HER2 tumors treated with PBS (I-IV) or αHER2-huEndo-P125A (V-VIII) is presented. Magnification: 50× (I-III, V-VII) or 100× (IV, VIII). Bars: 500 μm for I-III and V-VII, 200 μm for IV and VIII.
Figure 7:
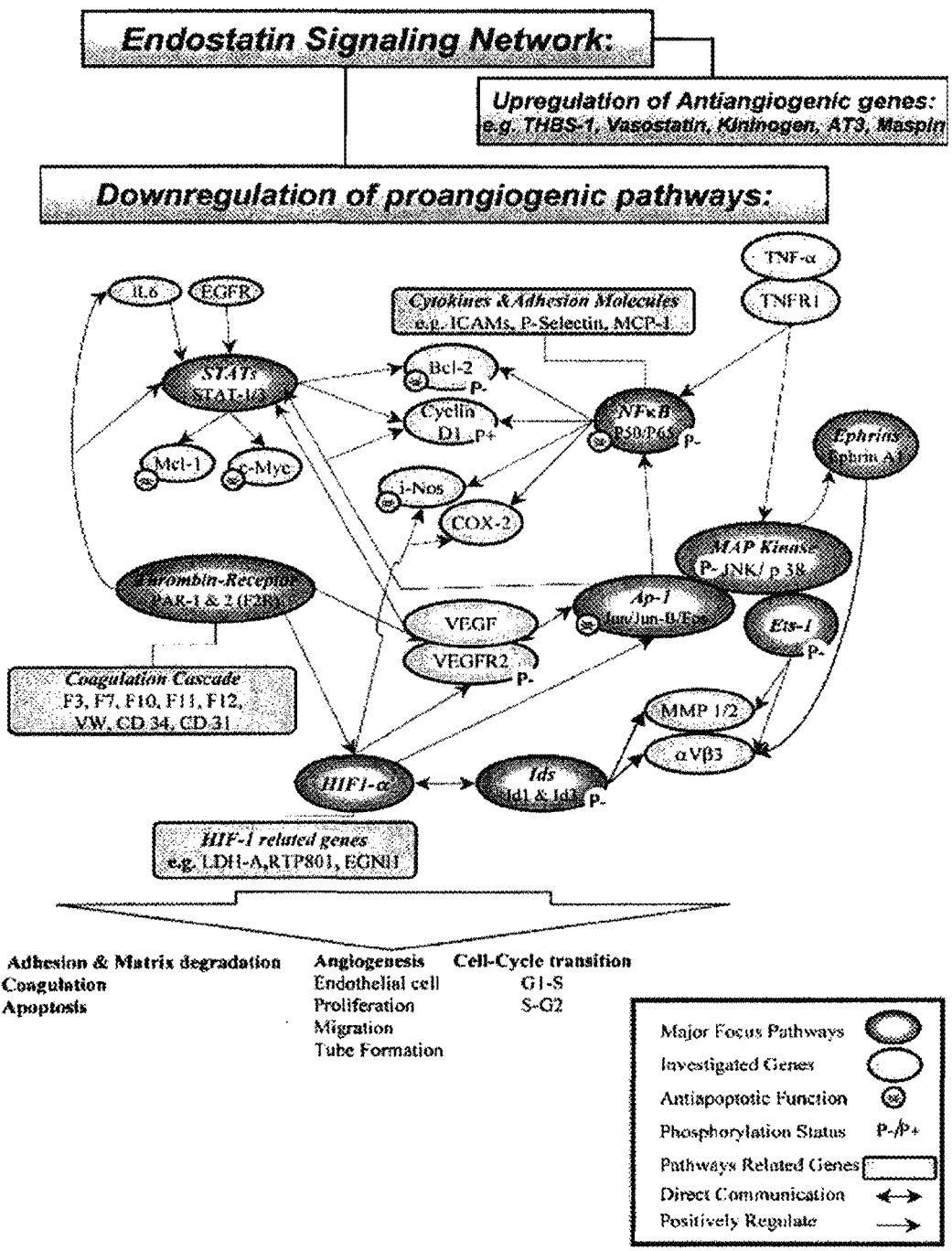
FIG. 7 is a schematic representation showing the endostatin signaling network.

Immunofluorescent Staining of Blood Vessel of Treated Tumor:

To investigate the effects of αHER2-huEndo-P125A fusion protein on tumor angiogenesis, tumors were resected, histologic sections of tumors were derived from treated and untreated mice after 4 or 7 treatments, and tumor microvasculature was visualized using anti-PECAM fluorescence immunostaining (FIG. 6) Immunofluorescent staining of EMT6-HER2 tumors demonstrated that the antibody-endostatin fusion treated group showed thin, short, and fragmented blood vessels on day 12 after 4 treatments (FIG. 6A), compared to those of the PBS treated group (FIG. 6B). The total blood vessel density (Vd) was measured by determining the area that was occupied by vessels. Treatment with αHER2-huEndo-P125A fusion protein caused a statistically significant decrease in total Vd in tumors (FIG. 6C, mean total Vd treated with αHER2-huEndo-P125A fusion=32020 pixel, mean total Vd treated with PBS=58560 pixel, difference between mean total Vd=26540±6574, 95% CI=11380 to 41700, p=0.0038). To investigate average blood vessel area, total Vd was divides by vessel numbers. Tumors treated with endostatin fusion showed an extremely significant reduction of average Vd (FIG. 6D, mean average Vd treated with αHER2-huEndo-P125A fusion=44.07 pixel, mean average Vd treated with PBS=112.1 pixel, difference between mean average Vd=68.05±13.25, 95% CI=37.50 to 98.60, p=0.0009). By day 18 (7 treatments), EMT6-HER2 tumor from one of two mice treated with αHER2-huEndo-P125A had completely regressed and the other in the treated group demonstrated very small tumor without any clearly stainable vessels, while vasculature was readily demonstrated in PBS treated tumors.

Discussion:

Anti-angiogenic therapy with endostatin has been shown to block tumor growth in mice with little or no evidence for emergence of resistance despite multiple cycles of therapy, in a variety of murine models. In several murine models, repeated treatment with endostatin resulted in permanent eradication of tumors. However, Phase I/II studies of human endostatin did not demonstrate the levels of anti-tumor activity seen in murine models, although these clinical trials evidenced that human endostatin is a very safe drug when used at a variety of dose schedules (Hansma A H, Broxterman H J, van der Horst I, et al. *Ann Oncol* 2005; 16(10): 1695-701; Kulke M H, Bergsland E K, Ryan D P, Enzinger P C, et al. *J Clin Oncol* 2006; 24(22):3555-61). We hypothesized that several of the logistical disadvantages of the long-term treatment with high dosages of endostatin could be overcome if the half-life of endostatin could be extended and if endostatin could be specifically targeted to the tumor, to achieve higher local concentrations and greater specificity. In addition, we hypothesized that endostatin might be more effective if delivered as a dimer in the context of an antibody fusion protein. We had demonstrated that an anti-HER2 IgG3-$C_H$3-murine endostatin fusion protein retained anti-angiogenic activity, exhibited prolonged serum half-life and stability, selectively targeted tumors bearing HER2, inhibited blood vessel formation, and inhibited tumor growth more effectively in vivo than either endostatin or anti-HER2 antibody alone or delivered in combination (Cho H M, Rosenblatt J D, Kang Y S, et al. *Mol Cancer Ther* 2005; 4(6):956-67). We demonstrated the ability of such fusions to selectively localize to HER2+ tumors, and noted enhanced efficacy in several murine models including the CT26-HER2, EMT6-HER2 murine tumors which had been engineered to express human HER2, and against SKBR3 xenografts that constitutively express high levels of HER2.

In order to reduce the possible antigenicity of the murine endostatin fusion domain in preparation for human application, we have now constructed two new fusions based on human endostatin and on a mutated form of endostatin with increased anti-angiogenic properties. The αHER2-huEndo and αHER2-huEndo-P125A fusion proteins markedly inhibited endothelial tube formation and proliferation of HUVEC in vitro, and did so more efficiently than human endostatin. The αHER2-huEndo-P125A fusion protein showed greater inhibition of tube formation in vitro than either native endostatin or than wild type αHER2-huEndo fusion. Treatment of established SK-BR-3 xenografts in SCID mice with the αHER2-huEndo-P125A fusion resulted in greater inhibition of growth, compared to αHER2 IgG3, human endostatin, or αHER2-huEndo fusion protein treated mice. The αHER2-huEndo fusion protein specifically targeted tumors expressing HER2 and inhibited tumor growth in syngeneic mice simultaneously implanted with EMT6 and EMT6-HER2. αHER2-huEndo-P125A inhibited EMT6-HER2 tumor growth more effectively than PBS, or human endostatin (p value=0.003). Combining the targeting capability of anti-HER2 antibody with the anti-angiogenic activity of human endostatin presented in a dimer form in the context of a fusion antibody improves the inhibition of endothelial tube formation and proliferation of HUVEC in vitro and enhances anti-tumor activity in vivo.

In the endothelial tube formation experiment, the human endostatin fusion proteins led to profound morphologic changes in HUVEC, and prevented tube formation. Human or murine endostatin treatment inhibited HUVEC assembly into tubular structures in vitro, with cells remain dispersed and exhibit a morphology resembling adherent cells on plastic rather than aggregating into characteristic capillary-like tubes. Dimers or trimers of endostatin stimulated the motility of endothelial cells, but endostatin monomers did not, which demonstrated that endostatin oligomerization was important for the efficient inhibition of tube formation activity. Since the αHER2-huEndo fusion proteins retain two endostatin domains in a fusion protein, they may effectively present endostatin as a dimer, and this may result in more dispersed and scattered morphology of HUVECs seen in these experiments. Dimerization of the endostatin domain of the fusion proteins could further facilitate binding to integrins, perlecan, and glypicans, and further increasing fusion protein activity. The mutant αHER2-huEndo-P125A fusion variant inhibited tube formation of HUVEC in vitro and tumor growth in vivo more effectively than αHER2-huEndo.

Linking endostatin to an antibody may significantly enhance the anti-tumor activity of trastuzumab. Because the overall response rates of HER2+ breast cancers to trastuzumab remain relatively low (15-34%) (Fricke I, et al. *Clin Cancer Res* 2007; 13(16):4840-8; Baselga J, et al. *J Clin Oncol* 1996; 14:737-44; Vogel C L, et al. *J Clin Oncol* 2002; 20(3):719-26; Burstein H J, et al. *J Clin Oncol* 2003; 21(15):2889-95), this approach holds promise for increasing both response rate and duration relative to trastuzumab, and may expand the spectrum of anti-tumor activity of trastuzumab given alone or in combination with other anti-tumor strategies such as other cytotoxic agents (carboplatin, docetaxel), and/or anti-angiogenic drugs (e.g. bevacizumab; anti-VEGF antibody, thrombospondin-1). Since administration of endostatin appears to be quite safe, antibody-endostatin fusion proteins may also be suitable for use in the adjuvant setting as well. Indeed, we have observed marked synergy when the anti-HER2 IgG3-murine endostatin fusion and the anti-VEGF antibody bevacizumab were given in combination to SK-BR-3 xenograft containing mice. This indicates the antibody fusion may be useful when combined with other anti-angiogenic approaches.

In addition to endostatin, other anti-angiogenic domains could also be incorporated into fusions (e.g. angiostatin, tumstatin, etc). Since endostatin is a powerful and global regulator of angiogenic gene expression, we concentrated initial experiments on endostatin as a candidate fusion. Finally, in addition to the HER2 antigenic target, targeting anti-angiogenic proteins using antibody is a versatile approach that could be applied to other tumor targets (such as epidermal growth factor receptor or prostate-specific membrane antigen) through substitution with other antibody specificities/variable domains. This approach could be used to enhance efficacy and utility of antibodies directed to tumor antigens in which parental antibody shows only modest efficacy (e.g. Cetuximab).

Example 2

Chimeric Molecules

Examples of Ig-endostatin chimeric molecules include anti-HER2/neu scFv-Endo, anti-HER2/neu IgG3-$C_H$1-Endo, anti-HER2/neu IgG3-H-Endo, and Endo-anti-HER2/neu IgG3 fusion proteins. In one method to produce antibody fusion proteins, vectors that contained unique restriction sites at the 3' end of the $C_H$1 exon, immediately after the hinge, or at the 3' end of the $C_H$3 exon as well as on the variable domains of both human kappa light chain and IgG3 heavy chain IgG3 were used. Using these constructs, endostatin could be joined to anti-HER2/neu after $C_H$1 of anti-HER2/neu IgG3; and endostatin of Endo-IgG3 could be joined at the amino-terminus of the variable region with flexible linker (Gly$_4$-Ser)$_3$. The Fv genes of anti-HER2/neu heavy (FvH) and light chain (FvL) variable region genes could be cloned by PCR, and the cloned Fv gene fragments joined with a flexible linker (Gly$_4$-Ser)$_3$. Endostatin was joined at the 3' end of the FvL-(Gly$_4$-Ser)$_3$-FvH gene to form scFv-Endo. The constructed fusion genes could be expressed in myeloma cell line SP2/0. For example, transfectomas expressing anti-HER2/neu IgG3-$C_H$3-Endo fusion, endostatin, anti-HER2/neu IgG3, and anti-dansyl IgG3 of unrelated control specificity have been generated. To purify the fusion proteins produced by the host cells, the proteins were isolated from culture medium through protein A affinity chromatogaraphy for $C_H$3-Endo and Endo-IgG3, or using heparin affinity chromatography (which binds to the endostatin moiety) for scFv-Endo, $C_H1$-Endo, and H-Endo which lack a protein A-binding site. For fusion proteins containing both heavy and light chains, size and assembly into $H_2L_2$ form is assessed using SDS-PAGE. Western blotting analysis with rabbit anti-endostatin sera can be used to detect the attached endostatin moiety. Expected characteristics of the fusion proteins are shown below.

| Recombinant Proteins | "Predicted" Properties of Fusion Protein | | | |
|---|---|---|---|---|
| | Tumor Penetration | HER2/neu Binding Ability | Serum Half-Life | Effector Function |
| IgG3 Heavy Chain | ++ | ++++ | +++ | Yes |
| Single Chain Fv-Endo (ScFv-Endo) | ++++ | ++ | + | No |
| IgG3-$C_H$1-Endo ($C_H$1-Endo) | +++ | +++ | ++ | No |
| IgG3H-Endo (H-Endo) | ++ | ++++ | +++ | No |
| IgG3-$C_H$3-Endo ($C_H$3-Endo) | ++ | ++++ | +++ | Yes |
| Endo-IgG3 | ++ | ++++ | +++ | Yes |

Example 3

Serum Stability Studies

To characterize the in vivo pharmacokinetic patterns of the antibody-endostatin fusion protein, mice with/without implanted tumors (CT26 or CT26-HER2/neu) were injected intravenously with [$^{125}$I] labeled anti-HER2/neu IgG3, anti-HER2/neu IgG3-$C_H$3-Endo, endostatin, and a control anti-dansyl IgG3 and clearance of endostatin on fusion measured. [$^{125}$I]-endostatin was rapidly removed from the plasma compartment in mice with/without tumors ($T_{1/2}^2$ elimination: 0.5-3.8 hrs), while the rate of removal of [$^{125}$I] labeled anti-HER2/neu IgG3-$C_H$3-Endo ($T_{1/2}^2$: 40.2-44.0 hrs) was similar to those of [$^{125}$I] labeled anti-HER2/neu IgG3 ($T_{1/2}^2$: 39.9-63.8 hrs) and control anti-dansyl IgG3 ($T_{1/2}^2$: 43.7-46.5 hrs).

To analyze the serum stability of [$^{125}$I] labeled anti-HER2/neu IgG3, anti-HER2/neu IgG3-$C_H$3-Endo, endostatin and anti-dansyl IgG3 plasma samples were TCA-precipitated and counted. 96 hours following injection approximately 90% of the anti-HER2/neu IgG3 and anti-HER2/neu IgG3-$C_H$3-Endo in serum remained intact. Endostatin was rapidly eliminated with little remaining in the circulation by 60 min. For endostatin, approximately 90% was intact 2 min after injection and only 55% of the remaining circulating endostatin remained intact at 60 min. In contrast anti-HER2/neu IgG3-$C_H$3-Endo cleared much more slowly with kinetics resembling anti-HER2/neu IgG3 and anti-dansyl IgG3. Analysis of serum samples by SDS-PAGE confirmed that the anti-HER2/neu IgG3-$C_H$3-Endo in circulation remained intact.

Example 4

Biolocalization Studies

To measure biodistribution and biolocalization of the endostatin fusion protein, purified endostatin fusion protein was labeled with $^{125}$I. 96 hours following an intravenous injection into mice bearing tumors, the radiolocalization indices (the % injected dose [ID]/g in tumor divided by the % ID/g in blood) of anti-HER2/neu IgG3-$C_H$3-Endo and anti-HER2/neu IgG3 were similar. Anti-HER2/neu IgG3-$C_H$3-Endo showed a tumor/blood ratio of 3.76 for CT26-HER2/neu and a 0.50 tumor/blood ratio for CT26; whereas anti-HER2/neu IgG3 showed 2.83 and 0.47 ratios for CT26-HER2/neu and CT26, respectively. No enhanced targeting to tumors was seen for endostatin alone. Therefore, both anti-HER2/neu antibody and anti-HER2/neu antibody-endostatin fusion protein retained the ability to localize to HER2/neu bearing tumors.

In mice simultaneously implanted with CT26 and CT26 expressing HER2/neu (CT26-HER2) tumors on opposite flanks, $^{125}$I-labeled anti-HER2/neu IgG3-endostatin fusion protein and anti-HER2/neu IgG3 preferentially localized to CT26-HER2 tumors. Specific tumor radiolocalization indices of anti-HER2/neu IgG3-endostatin were actually greater than those of anti-HER2/neu IgG3 in several separate experiments. This indicated relative localization of targeted antibody-endostatin fusions to tumor due to binding to HER2/neu target antigen.

| Treatment | Time (Hrs) | CT26 (% ID/g) | CT26-HER2 (% ID/g) | Radiocalization Indices* |
|---|---|---|---|---|
| Anti-HER21 neu IgG3 | 6 | 3.51 ± 1.38 | 3.94 ± 1.83 | 1.12 |
| | 24 | 7.04 ± 3.48 | 14.95 ± 3.48 | 2.12 |
| | 98 | 3.03 ± 0.63 | 7.88 ± 2.18 | 2.60 |
| Anti-HER21 neu IgG3-endostatin | 6 | 1.16 ± 0.38 | 6.20 ± 0.76 | 5.34 |
| | 24 | 1.31 ± 0.60 | 9.72 ± 1.05 | 7.42 |
| | 96 | 0.33 ± 0.05 | 1.17 ± 0.07 | 3.55 |

*Radiolocalization Indices represent the ratios of the % ID/g in CT26-HER2 divided by the % ID/g in CT26.

Example 5

Anti-Tumor Studies

The ability of anti-HER2/neu IgG3-$C_H$3-Endo, anti-HER2/neu IgG3 and endostatin to preventing the growth of CT26 expressing HER2/neu in BALB/c mice was examined BALB/c mice were subcutaneously injected with 1×106 cells and tumor growth measured. On day 7, most of mice developed palpable tumors (about 5 mm in diameter) and the treatment of mice bearing tumors (n=5 per group) initiated every other day by intravenous injection (5 times) of anti-HER2/neu IgG3-$C_H$3-Endo, anti-HER2/neu IgG3, anti-dansyl IgG3, endostatin, or PBS controls. Tumor growth in mice treated with anti-HER2/neu IgG3 or endostatin was reduced relative to anti-dansyl IgG3 or PBS controls. Treatment with anti-HER2/neu IgG3-$C_H$3-Endo resulted in additional reduction in tumor volume. Anti-HER2/neu IgG3-$C_H$3-Endo demonstrated significant growth inhibition (p<0.05) compared with PBS, anti-HER2/neu IgG3 or endostatin administered at two-fold molar excess relative to anti-HER2/neu IgG3-endostatin alone. A ten-fold increase in endostatin alone further increased efficacy.

In mice simultaneously implanted with CT26, and CT26-HER2/neu on opposite flanks, equimolar administration of anti-HER2/neu IgG3-endostatin to mice showed preferential inhibition of CT26-HER2/neu, compared to contralaterally implanted CT26 parental tumor. Anti-HER2/neu IgG3-endostatin inhibited more effectively than endostatin, anti-HER2/neu IgG3 antibody, or the combination of antibody and endostatin (p<0.05).

Whether anti-HER2/neu IgG3-endostatin, endostatin, anti-HER2/neu IgG3 antibody, or the combination of antibody and endostatin would inhibit the growth of the human breast cancer SK-BR-3 in SCID mice was examined SCID mice (n=8 per group) were subcutaneously injected with 1×10⁶ cells of SK-BR-3 and tumor growth measured. By day 15, most mice developed palpable tumors (about 5 mm in diameter) and treatment was initiated every other day with intravenous injection (10 times) of anti-HER2/neu IgG3-$C_H3$-Endo, anti-HER2/neu IgG3, endostatin, or the combination of antibody and endostatin. Mice treated with anti-HER2/neu IgG3-$C_H3$-Endo, endostatin, anti-HER2/neu IgG3 antibody, or the combination of antibody and endostatin all showed inhibition of tumor growth. Administration of anti-HER2/neu IgG3-$C_H3$-Endo consistently resulted in the greater reduction of tumor volume, compared to either anti-HER2/neu antibody alone, endostatin alone, or antibody and endostatin given in combination (p<0.05).

Example 6

Production and Characterization of Anti-HER2/neu IgG3-Endostatin

The anti-HER2/neu antibody-endostatin fusion protein of the expected molecular weight was produced and secreted from the stably transfected Sp2/0 cell lines as the fully assembled $H_2L_2$ form. The secreted ³⁵S-methionine labeled anti-HER2/neu IgG3-endostatin has a molecular weight of approximately 220 kDa under non-reducing conditions, the size expected for a complete antibody (170 kDa) with 2 molecules of endostatin (25 kDa) attached. Following reduction, H and L chains of the expected molecular weight were observed. To confirm that the endostatin moiety was present in the anti-HER2/neu IgG3-endostatin protein, purified anti-HER2/neu IgG3-endostatin and endostatin were resolved under non-reducing conditions. Following Western blotting, anti-HER2/neu IgG3-endostatin was identified at the molecular weight of 220 kDa by both anti-human IgG or anti-endostatin antibody. Following reduction, the predominant heavy chain band from anti-HER2/neu IgG3-endostatin migrated at the expected size of 85 kDa.

Example 7

Antiangiogenic Activity of Anti-HER2/neu IgG3-Endostatin

The ability of endostatin to block VEGF/bFGF-induced angiogenesis in vitro was tested using the chorioallantoic membrane (CAM) assay. Pellets containing Vitrogen and VEGF/bFGF (100 ng and 50 ng/pellet, respectively) and either anti-HER2/neu IgG3 (0.5-10 µg/pellet: 2.95-59 pmol/pellet), anti-HER2/neu IgG3-endostatin (0.5-10 µg/pellet: 2.25-45 pmol/pellet), or endostatin (0.5-10 µg/pellet: 20-400 pmol/pellet) were measured for invasion of new capillaries. Two independent preparations of anti-HER2/neu antibody-endostatin fusion protein were able to suppress the angiogenic response mediated by VEGF/bFGF in a dose-dependent manner with a specific activity similar to that seen with endostatin. In contrast anti-HER2/neu IgG3 showed no anti-angiogenic response. Therefore genetically engineered anti-HER2/neu-IgG3-endostatin maintains the ability to inhibit the angiogenic response mediated by VEGF/bFGF.

Example 8

Serum Clearance and Stability of Anti-HER2/neu IgG3-Endostatin

To characterize the pharmacokinetics of anti-HER2/neu IgG3-endostatin, mice with/without implanted tumors (CT26 or CT26-HER2) were injected intravenously with [¹²⁵I]-anti-HER2/neu IgG3, anti-HER2/neu IgG3-endostatin, endostatin, or a control anti-dansyl IgG3 and clearance of injected radiolabeled proteins measured. Representative results from mice with implanted HER2/neu-expressing CT26 tumors and the pharmacokinetic data for mice in all groups are summarized in Table 1. [¹²⁵I]-endostatin was rapidly removed from the plasma compartment in mice with or without tumors ($T_{1/2}^2$ elimination: 0.5-3.8 hrs), while the clearance rate of [¹²⁵I]-anti-HER2/neu IgG3-endostatin ($T_{1/2}^2$: 40.2-44.0 hrs) was similar to that of [¹²⁵I]-anti-HER2/neu IgG3 ($T_{1/2}^2$: 39.9-63.8 hrs) and anti-dansyl IgG3 ($T_{1/2}^2$: 43.7-46.5 hrs). Therefore endostatin fused with antibody is cleared from the peripheral compartment much more slowly than endostatin alone.

In mice bearing CT26-HER2 tumors (Table 1), the area under the plasma concentration curve (AUC) of anti-HER2/neu IgG3-endostatin was increased by a factor of 56 (13,100% IDmin/ml vs. 233% IDmin/ml) compared to endostatin, as a consequence of both a longer half-life of elimination (69 fold increase: 2,640 min vs. 38 min) and an increased "mean residence time" (MRT) (56 fold increase: 2800 min vs. 50 min). Endostatin was very rapidly removed from serum within 30 min, principally by glomerular filtration and renal clearance, but anti-HER2/neu IgG3-endostatin demonstrated much slower clearance from serum, similar to those of anti-HER2/neu IgG3 and anti-dansyl IgG3.

To analyze the serum stability of [¹²⁵I] labeled anti-HER/neu IgG3, anti-HER2/neu IgG3-$C_H3$-endostatin, endostatin and anti-dansyl IgG3, plasma samples were TCA-precipitated and counted. 96 hours following injection approximately 90% of the anti-HER2/neu IgG3 and anti-HER2/neu IgG3-endostatin in serum remained intact. For endostatin, approximately 90% was intact 2 min after injection and only 55% of the remaining circulating endostatin remained intact at 60 min. In contrast anti-HER2/neu IgG3-endostatin cleared much more slowly with kinetics resembling anti-HER2/neu IgG3 and anti-dansyl IgG3. Analysis of serum samples by SDS-PAGE confirmed that the anti-HER/neu IgG3-endostatin in circulation remained intact. Thus, the antibody moiety of anti-HER2/neu IgG3-endostatin fusion protein renders the genetically fused endostatin much more stable in the blood stream.

Example 9

Biodistribution and Biolocalization of Anti-HER2/neu IgG3-Endostatin

Ninety-six hours following an intravenous injection of mice bearing CT26-HER2 tumors, anti-HER2/neu IgG3 was found mainly in the tumor and blood (5.67 and 2.10% ID/g, respectively). The radiolocalization indices at 96 hours post injection (the % ID/g in tumor divided by the % ID/g in blood) of anti-HER2/neu IgG3-endostatin and anti-HER2/neu IgG3 were similar. Anti-HER2/neu IgG3-endostatin showed a tumor/blood ratio of 3.76 for CT26-HER2 and a 0.50 for CT26, whereas anti-HER2/neu IgG3 showed tumor/blood ratios of 2.83 and 0.47 for CT26-HER2 and CT26, respectively. Therefore, both anti-HER2/neu antibody and anti-HER2/neu antibody-endostatin fusion protein preferentially localized to HER2/neu expressing tumors.

To measure localization of antibody-endostatin fusion proteins to the antigenic target, mice simultaneously implanted with CT26 and CT26-HER2 tumors on opposite flanks were injected intravenously with either ¹²⁵I-labeled anti-HER2/neu IgG3-endostatin fusion protein or ¹²⁵I-labeled anti-HER2/neu antibody (Table 2). The biodistribution and biolocalization of the labeled proteins was examined at different times (6, 24, and 96 hours) after injection of labeled proteins. Anti-HER2/neu IgG3-endostatin fusion protein and anti-HER2/neu IgG3 preferentially localized to CT26-HER2 tumors. Specific tumor radiolocalization indices of anti-HER2/neu IgG3-endostatin were actually greater than those of anti-HER2/neu IgG3 (Table 2). This indicated that the relative localization of targeted antibody-endostatin fusions to tumor was due to binding to the HER2/neu target antigen (Table 2).

Example 10

Anti-Tumor Activities of Anti-HER2/neu IgG3-Endostatin In Vivo

Murine colon adenocarcinoma CT26 cells were transduced with the gene for HER2/neu antigen as previously described. The CT26-HER2 cells have been used in these studies and proliferated at the same rate in vitro as parental CT26 cells. Preliminary experiments revealed that the CT26-HER2 tumors implanted in BALB/c mice grew at the same rate as the parental CT26 tumors (Ref Lab Animal).

The anti-tumor effects of anti-HER2/neu IgG3-endostatin, anti-HER2/neu IgG3 and endostatin on the growth of CT26-HER2 in BALB/c mice were studied. Tumor growth in mice treated with anti-HER2/neu IgG3 or endostatin was reduced relative to an isotype control anti-dansyl IgG3 or PBS control. Treatment with anti-HER2/neu IgG3-endostatin resulted in additional reduction in tumor volume. Anti-HER2/neu IgG3-endostatin demonstrated significantly better growth inhibition when compared to PBS, anti-HER2/neu IgG3 or endostatin administered. Genetic fusion of endostatin to the anti-HER2/neu IgG3 initially appeared to inhibit tumor growth more efficiently than either anti-HER2/neu IgG3 or endostatin alone.

To confirm the preliminary experiments, mice were simultaneously implanted with CT26, and CT26-HER2 on opposite flanks. Administration of anti-HER2/neu IgG3-endostatin showed preferential inhibition of CT26-HER2 growth, compared to contralaterally implanted CT26 parental tumor. Anti-HER2/neu IgG3-endostatin inhibited more effectively than endostatin, anti-HER2/neu IgG3 antibody, or the combination of antibody and endostatin p<0.05).

Herceptin, anti-HER2/neu IgG1, was able to inhibit the growth of SK-BR-3 breast carcinoma cells, which overexpress HER2/neu. It was next determined whether anti-HER2/neu IgG3-endostatin, endostatin, anti-HER2/neu IgG3 antibody, or both antibody and endostatin in combination would inhibit the growth of human breast cancer SK-BR-3 xenografts in SCID mice. SK-BR-3 was implanted on the flank of SCID mice. The treatment was repeated 10 times. Administration of anti-HER2/neu IgG3-endostatin resulted in a greater reduction of tumor volume, compared to either anti-HER2/neu antibody alone, endostatin alone, or antibody and endostatin given in combination (p<0.05).

Example 11

Blood Vessel Formation in CT26-HER2 Tumors Treated with the Anti-HER2/neu IgG3-Endostatin Fusion Protein To better understand the mechanism of anti-tumor activity of the anti-HER2/neu IgG3-endostatin fusion protein, blood vessel formation in tumors was analyzed. Mice were simultaneously implanted with CT26 and CT26-HER2 tumors on opposite flanks and allowed to grow until the tumor diameter was 4-6 mm at which time the mice were intravenously treated with either anti-HER2/neu IgG3-endostatin fusion proteins or PBS. CT26-HER2 tumors grew slower in mice treated with anti-HER2/neu IgG3-endostatin compared to the others with kinetics similar to those above. After the fifth treatments, the tumors were removed and cryosections of tumors were immunohistochemically stained for endothelial cells with anti-PECAM-1 antibody to visualize the blood vessel formation of these tumors. The parental CT26 tumor tissue and the untreated CT26-HER2 tumor tissue appeared to have more vessels than CT26-HER2 treated with endostatin fusion proteins.

To distinguish the blood vessel formation, the tumor sections were stained with rat anti-mouse anti-PECAM antibody, detected with anti-rat IgG-Alexa 594, and then analyzed through confocal microscope. Confocal microscopic analysis for these tumors revealed striking differences in the vasculature between CT26-HER2 tumors treated with anti-HER2/neu IgG3-endostatin and the others, which may explain the altered tumor growth observed above. Images composed of 14-21 digital microscopic images showed that blood vessels in the parental CT26 tumors with/without endostatin fusion treatments and in PBS-treated CT26-HER2 tumors appeared more organized and branched than the blood vessels in the CT26-HER2 tumors treated with anti-HER2/neu IgG3-endostatin.

The alterations in vasculature were quantified by measuring the blood vessel density. The blood vessel density was measured by determining the area that was occupied by vessels, which provided the amount of vascular area within each tumor. Using this measure, the HER2/neu expressing tumors with endostatin fusion treatments had significantly less vascular area (16%) than did the untreated CT26-HER2 tumors (Table 3).

Example 12

Angiogenic Effects of VEGF Ischemic/Non-Ischemic Tissues

Antiangiogenic effects of the antibody-endostatin fusion proteins will be investigated using animal hindlimb models of therapeutic angiogenesis. Rat or rabbit hindlimb ischemia models are available. The ischemic levels in the rabbit model can be manipulated as maximal, severe, or moderate ischemic conditions.

Rabbit Hindlimb Ischemia Model:

The normal distribution of arteries and capillaries 1 h after surgery (iliac tie and femoral excision), flow through the iliac and femoral arteries was eliminated indicating ischemia. Although there had been significant collateral development and return of flow to the limb, flow through the femoral artery and its associated vessels was still absent. Significant inflammation, necrosis, or tissue loss was not detected despite the severe early ischemia indicating that the muscle was significantly reperfused. In contrast, the VEGF-treated limb recovered full flow to the distal branches of the femoral artery. Quantitation of these vessels from the original angiography revealed >10-fold more collateral vessels with external diameter >100 μm in the treated limbs. The generation of new vessels in the VEGF treated limbs could involve combinations of vasculogenesis, angiogenesis, and arteriogenesis.

Angiogenic Effects of VEGF in Non-Ischemia Model:

Neovascularization of non-ischemic tissues has been examined at the rat subcutaneous peritoneal fat pad and mouse ear flap. In both case sutures were tied into the tissues and 2×10$^9$ pfu of Ad-CMV-VEGF or Ad-β-Gal were injected around the sutures. Tissues were analyzed after 3-weeks. New vessels were clearly visible in both tissues injected with Ad-CMV-VEGF but not with the β-gal. The VEGF injected tissues also contained a visible red blush indicative of leaky vessels. These results showed that VEGF can activate angiogenesis/vasculogenesis in non-ischemic tissue.

Example 13

Combination Treatments with Other Antiangiogenic Strategies

PDGF Blockade:

Herceptin has been approved for the treatment of advanced breast cancer and Gleevec (STI57, imatinib, Novartis Pharma AG) has been approved for chronic myelogenous leukemia and gastrointestinal stromal tumors. Imatinib disrupts the association of pericytes with neovasculature in tumors through effects on PDGFR. While endostatin inhibits early blood vessel formation, imatinib may affect maturation by effects on pericytes. Initially MCF7 and MCF7-HER2 tumors subcutaneously implanted on the left and right flank, respectively, will be treated with a combination of anti-HER2 IgG3-huEndo and fusion proteins and imatinib. Imatinib (50 mg/kg) will be administered orally twice a day. The blood vessel formation and tumor growth in tumors will be examined as outlined supra.

VEGF Blockade:

A humanized anti-VEGF antibody (bevacizumab, AVASTIN™, rhuMAb-VEGF; Genentech) has been approved for use in combination with chemotherapy in a phase III trial in metastatic colon carcinoma. AVASTIN™ has been reported to have clinical benefit of 17% (complete and partial responses plus stable disease 6 months) in phase II trials in breast cancer. AVASTIN™ also has activity in renal cell carcinoma, and has been reported to augment taxane activity in a phase III breast cancer trial. AVASTIN™ binds and neutralizes all of the major isoforms of VEGF-A, decreases vascular volume, microvascular density, interstitial fluid pressure and the number of viable, circulating endothelial cells. Combining fusion proteins with AVASTIN™ may augment activity of both approaches. SK-BR-3, or MCF7 and MCF7-HER2 tumors in SCID mice will be treated in combination with AVASTIN™ (50 μg/injection) and anti-HER2 antibody-huEndo fusion proteins (10, 50, and 250 μg/injection, i.v., q.o.d.) or human endostatin, or antibody alone.

Metronomic Therapy:

Proliferating endothelial cells forming new blood vessels within tumors are sensitive to the cytotoxic effects of many chemotherapeutics. Conventional chemotherapeutic regimes with maximum tolerable doses require extended rest periods which allow repair of the endothelial compartment. However, "metronomic" therapy (i.e. administration of continuous low-doses) may sustain antiangiogenic effects. MCF7/MCF7-HER2 tumors will be treated in SCID mice in combination with various concentrations of anti-HER2 antibody-huEndo fusion proteins (10, 50, and 250 μg/injection, i.v., q.o.d.) and low dose cyclophosphamide (CTX, 25 mg/kg/day, p.o.), 79-80 or alone. Repeated administration of low dose taxanes (paclitaxel or docetaxel), using "metronomic" scheduling for the treatment of cancers will also be tested.

Example 14

Construction, Purification, and Characterization of Anti-EGFR

Figure 16:
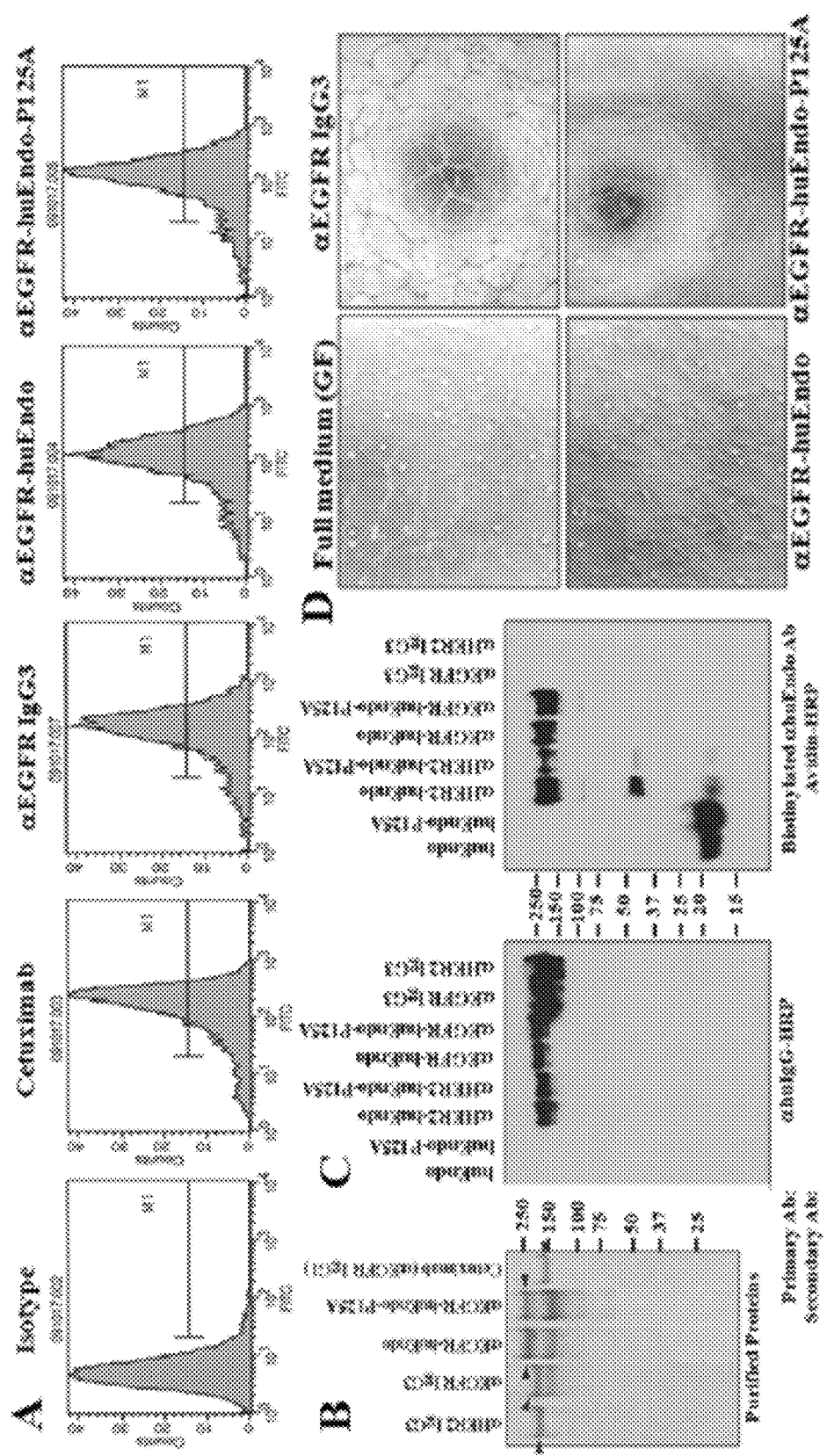
FIG. 16. A. To test binding to EGFR antigen, EGFR+ A431 tumor cells were incubated with antibodies and bound antibodies were detected by anti-human IgG-FITC. B. Purified αEGFR-huEndo fusion proteins (arrows) detected with Coomassie blue staining. C. To identify human endostatin on the fusion proteins, the fusion proteins were detected by western blotting with a biotinylated anti-human endostatin antibody/avidin-HRP and anti-human IgG-HRP. D. Effects of anti-EGFR-huEndo fusion proteins on EC tube formation. HUVECs were resuspended endothelial cell growth medium and treated as indicated before plating onto the Matrigel-coated plates. Following 16 hr of incubation, tube formation was observed through an inverted photomicroscope. Tube formation with media alone and αEGFR IgG3 (45.46 nM) were compared to those with αEGFR-huEndo-P125A (45.46 nM).

IgG3-huEndo Fusion Proteins:

We obtained publically available amino acid sequences of Cetuximab (disclosed in Patent Publication No. WO2008083949, which is incorporated herein by reference in its entirety). The DNA sequences of the heavy and light chains were deduced using the Vector NTI program and DNA sequences were synthesized. The heavy and light chain variable region genes were cloned into pUC57 vector (EcoRV site). The anti-EGFR heavy chain variable region gene fragment (EcoRV-NheI) was cloned into the EcoRV-NheI site of the human IgG3 and human IgG3-huEndo-P125A expression vectors and the anti-EGFR light chain variable region gene fragment (EcoRV-SalI) was cloned into the EcoRV-SalI site of the human kappa expression vector. Anti-EGFR IgG3 (αEGFR IgG3), anti-EGFR IgG3-huEndo (αEGFR-huEndo) or anti-EGFR IgG3-huEndo-P125A (αEGFR-huEndo-P125A) fusion genes were co-transfected into B cell myeloma, SP2/0 or P3 cells, by electroporation. αEGFR IgG3, αEGFR-huEndo and αEGFR-huEndo-P125A fusion proteins were synthesized and purified (FIG. 16). Binding of αEGFR IgG3, cetuximab, αEGFR-huEndo, and αEGFR-huEndo-P125A fusions to EGFR on epidermoid carcinoma A431 cells were confirmed by flow cytometry (FIG. 16A). The purified fusion protein has a molecular weight of 220 kDa under nonreducing conditions (FIG. 16B). We confirmed the presence of endostatin in the fusion proteins by western blotting with a biotinylated anti-human endostatin antibody/avidin-HRP and anti-human IgG-HRP (FIG. 16C). αEGFR-huEndo and αEGFR-huEndo-P125A were identified by both anti-human IgG and anti-endostatin antibody (FIG. 16C). αEGFR-huEndo fusion proteins inhibited VEGF and bFGF induced endothelial cell tube formation in vitro, more efficiently than endostatin alone, or parental αEGFR IgG3 (FIG. 16D).

Example 15

Effects on Vasculogenic Mimicry

Figure 8:
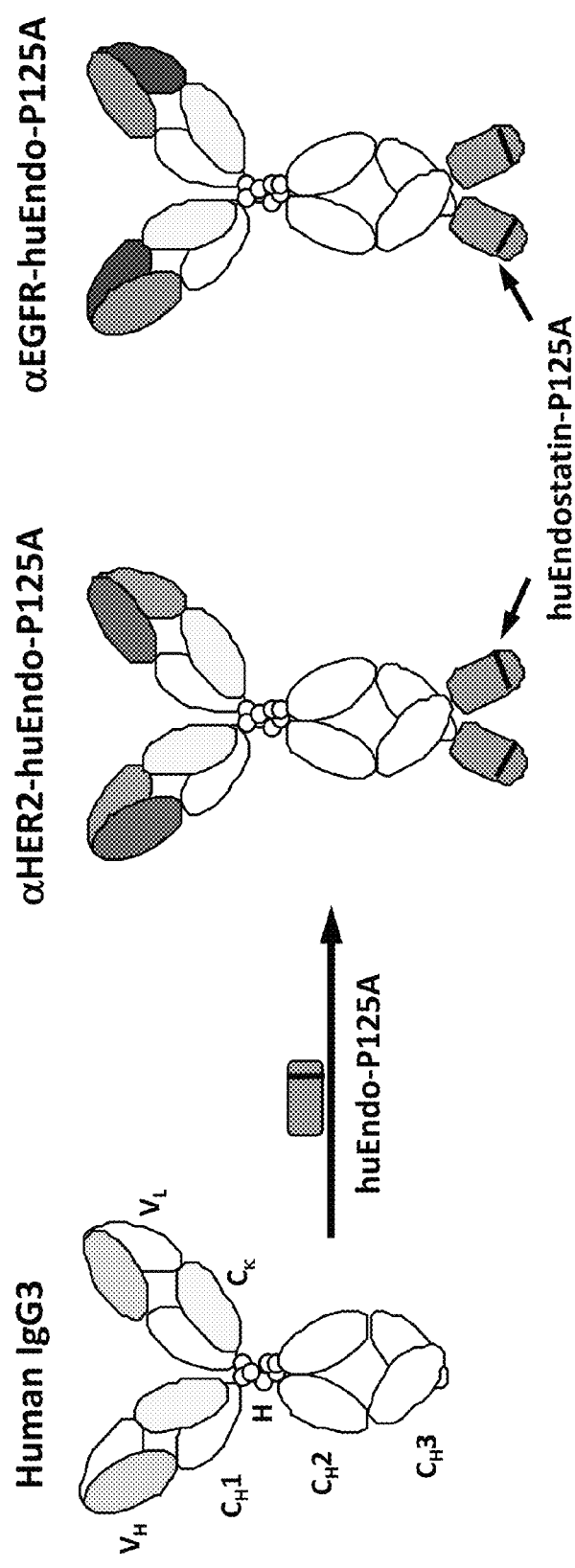
FIG. 8. Schematic diagram of human IgG3-human mutant endostatin fusion proteins. Human mutant endostatin at 125 (Proline to Alanine: P125A) is represented as huEndo-P125A, anti-HER2 IgG3-human mutant endostatin as αHER2-huEndo-P125A, and anti-EGFR IgG3-human mutant endostatin as αEGFR-huEndo-P125A.
Figure 9:
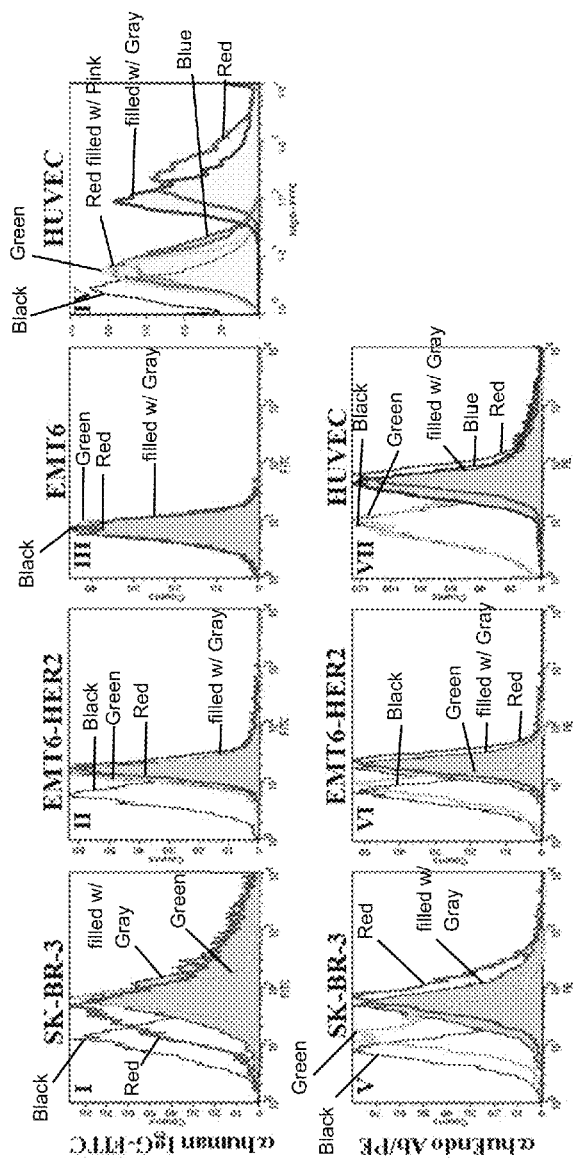
FIG. 9. (A) Binding of anti-HER2 human endostatin fusion proteins to HER2 antigen and HUVECs, and recognition by anti-human endostatin antibody. Human breast cancer cells, SK-BR-3 (I, V), murine mammary tumor cells, engineered to express HER2, EMT6-HER2 (II, VI) and EMT6 (III), or human umbilical vein endothelial cells (HUVECs) (IV, VII) were incubated with αHER2-huEndo (filled with gray), αHER2-huEndo-P125A (red line), αHER2 IgG3 (green line), human endostatin (blue line), human endostatin-P125A (red line filled with pink), or isotype control (anti-dansyl IgG3, black line). The bound fusion proteins were identified with either anti-human IgG-FITC conjugated (I-IV), or with biotinylated anti-human endostatin antibody and secondarily stained with a streptavidin-PE conjugate (V-VII). (B) Serum clearance of human endostatin fusion proteins following intravenous administration to mice. αHER2-huEndo (open circle), αHER2-huEndo-P125 (filled circle), huEndo (open triangle), and huEndo-P125A (filled triangle) were injected via tail vein of BALB/c mice (n=3). At the indicated time points, serum samples were assayed by an ELISA which detects human endostatin. The data are presented as the mean±95% C.I. A representative experiment is shown.
Figure 9:
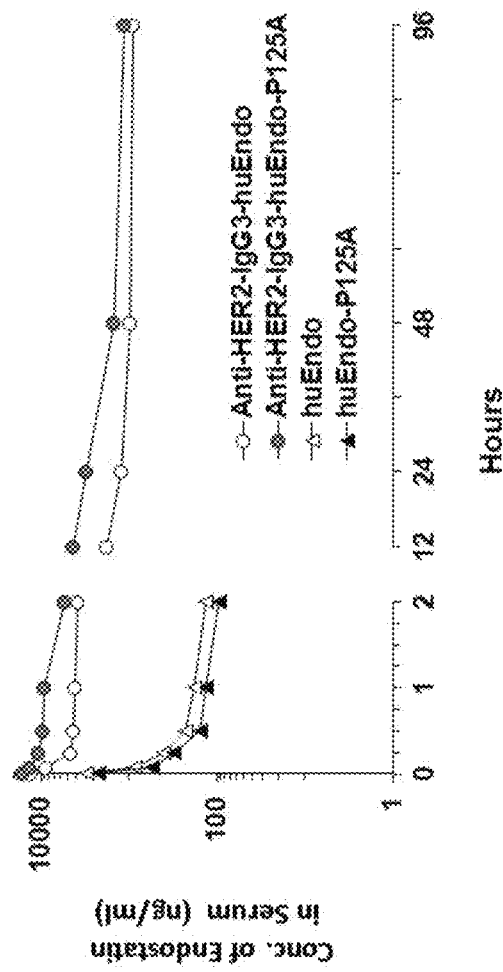

This example describes inhibition of vasculogenic mimicry. In these experiments, we tested two antibody-human mutant endostatin fusions (αHER2-huEndo-P125A and αEGFR-huEndo-P125A) with different antibody specificities for use in the treatment of human tumors expressing the corresponding targets (FIG. 8). αHER2-huEndo-P125A has enhanced antiangiogenic properties, relative to those seen with wild type endostatin in the fusion molecule. Enhanced antiangiogenic properties were initially noted using a fusion with anti-HER2 specificity and endostatin-P125A. The anti-HER2 IgG3-Endostatin-P125A fusion protein (αHER2-huEndo-P125A) demonstrates strong binding to HER2 through the antibody domain, and binding to HUVEC (human umbilical vein endothelial cells) through the endostatin domain (FIG. 9A). The administration of the αHER2-huEndo-P125A protein to mice in vivo demonstrated a significantly prolonged half-life compared to either human endostatin (huEndo) or huEndo-P125A (FIG. 9B).

Figure 10:
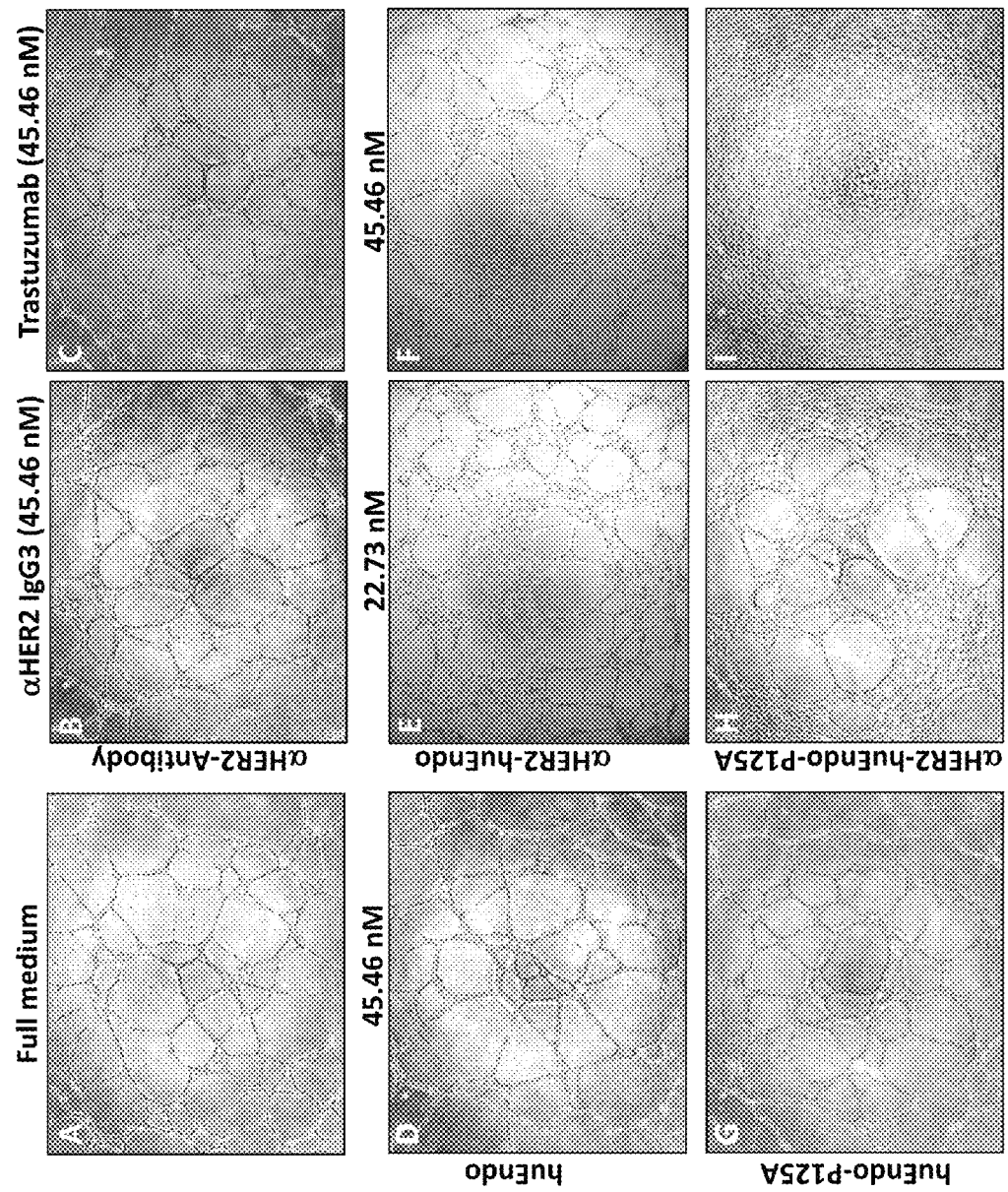
FIG. 10. Effects of anti-HER2 IgG3-huEndo fusion proteins on HUVEC tube formation. HUVECs were resuspended in endothelial cell growth medium and treated as indicated before plating onto the Matrigel-coated plates. Following 16 hr of incubation, tube formation was observed through an inverted photomicroscope. Tube formation with media alone (A), 45.46 nM αHER2 IgG3 (B), 45.46 nM trastuzumab (C), 45.46 nM huEndo (D), and 45.46 nM huEndo-P125A (G) were compared to those with 22.73 and 45.46 nM αHER2-huEndo (E-F) and 22.73 and 45.46 nM αHER2-huEndo-P125A (H-I).

We tested for the antiangiogenic properties of αHER2-huEndo-P125A in vitro using an endothelial cell tube formation assay. HUVECs were suspended in endothelial cell growth medium (EGM) and plated on matrigel coated plates with EGM. Following sixteen hours of incubation we assayed for tube formation quantitatively using a microscope (FIG. 10). Neither huEndo nor huEndo-P125A used alone, showed significant effects on tube formation (a surrogate assay for angiogenesis). Neither trastuzumab nor parental anti-HER2 IgG3 (αHER2 IgG3) antibody had any effects on tubule formation in contrast to anti-HER2 IgG3-endostatin fusion using wild type endostatin (αHER2-huEndo) which significantly inhibited angiogenesis. However, αHER2-huEndo-P125A had significantly greater inhibitory affects on angiogenesis, resulting in complete abrogation of tube formation at a concentration of 45.46 nM. Hence, the fusion protein incorporating huEndo-P125A had significantly greater effects than either a wild type endostatin fusion or than mutant endostatin (huEndo-P125A) alone. This is an unexpected finding.

Figure 11:
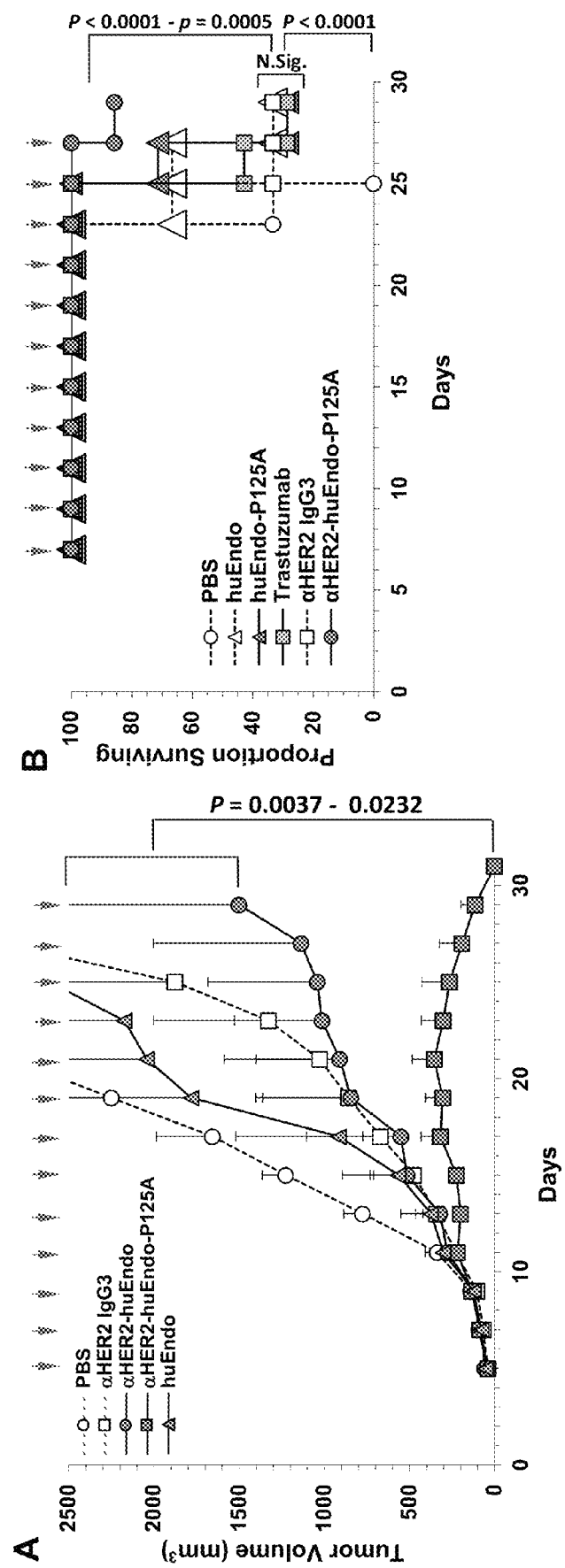
FIG. 11. (A) Anti-tumor efficacy of anti-HER2 IgG3-huEndo fusion proteins. SCID mice (n=5) were implanted s.c. with 2×10⁶ SK-BR-3 on day 0, then i.v. injected with αHER2-huEndo fusion proteins (42 μg), αHER2 IgG3 (34 μg), huEndo (8 μg), or PBS every other day (indicated with arrows) starting on day 5. Tumor growth was measured as described above. The values represent mean±95% CI of tumor volume (mm³) of 5 mice. Experiments were repeated three times with similar results. A representative experiment is shown. (B) Survival of mice per treatment group. αHER2-huEndo-P125A (42 μg), huEndo (8 μg), huEndo-P125A (8 μg), αHER2 IgG3 (34 μg), trastuzuman (30 μg), or PBS every other day (indicated with arrows) starting on day 6. Mice with greater than 2500 mm³ tumor volume were euthanized. The proportion surviving in each mouse group (%) is indicated. N. Sig.: not significant. (This is separate experiment from that shown in FIG. 11A.)

The in vitro effects on angiogenesis were then recapitulated in vivo using a SKBR3 xenograft model for HER2+ breast cancer grown in SCID mice. Although wild type αHER2-huEndo had greater activity than antibody or endostatin administered alone (or combined), use of the αHER2-huEndo-P125A fusion administered repeatedly intravenously over a 30 day period resulted in complete elimination of tumor growth which was statistically superior as compared to wild type fusion alone (FIG. 11). Hence, the αHER2-huEndo-P125A fusion had unexpectedly greater effects against breast cancer xenograft growth in vivo, than either a parental antibody or antibody endostatin fusion with wild type endostatin.

Figure 12:
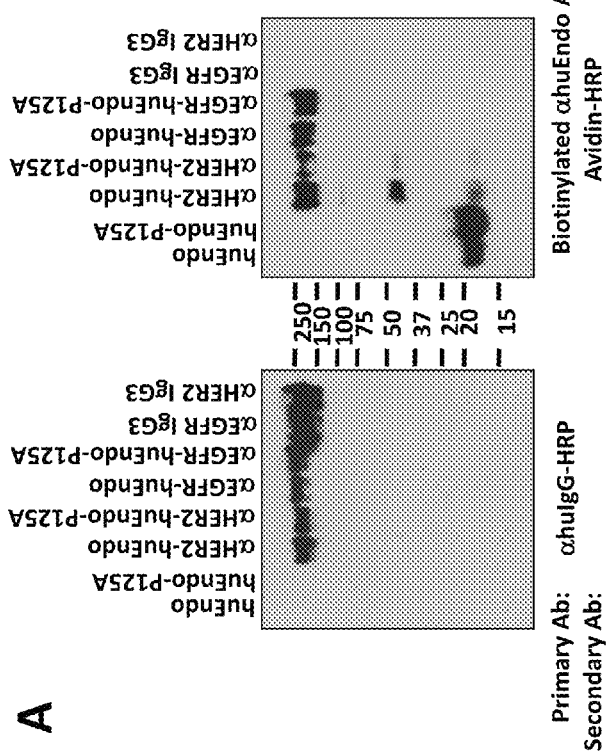
FIG. 12. Recognition by anti-human endostatin antibody and binding of anti-EGFR human endostatin fusion proteins to EGFR antigen. (A) To identify human endostatin on the fusion proteins, the fusion proteins were detected by western blotting with a biotinylated anti-human endostatin antibody/avidin-HRP and anti-human IgG-HRP. (B) To test binding to EGFR antigen, EGFR+ A431 tumor cells were incubated with antibodies and bound antibodies were detected by anti-human IgG-FITC for detection of the human IgG domain and a biotinylated anti-human endostatin antibody/avidin-FITC for detection of the endostatin domain.
Figure 12:
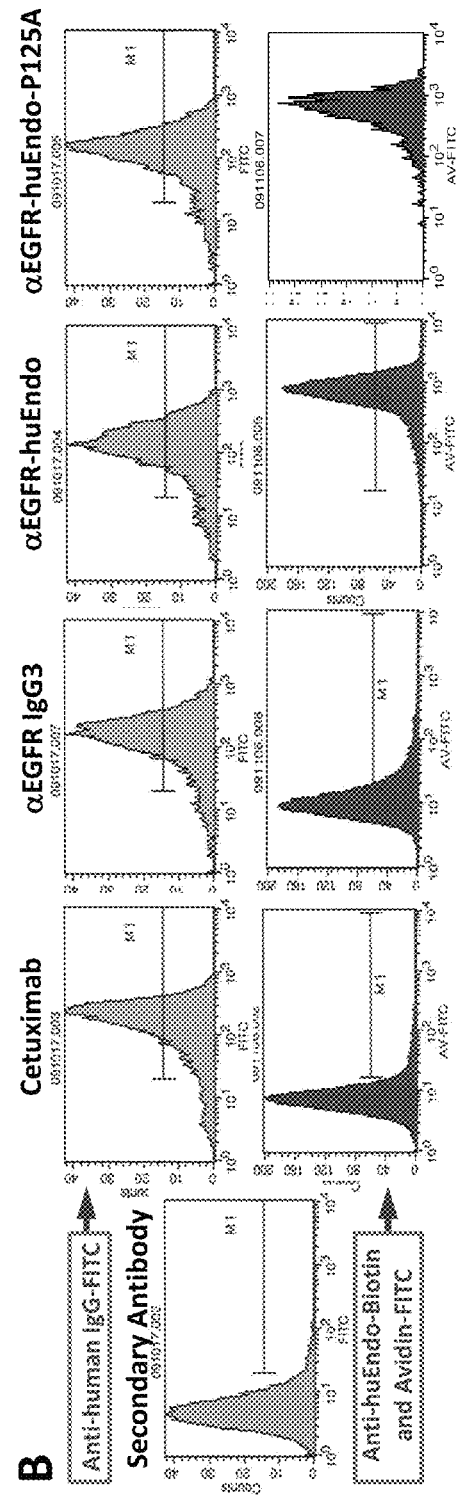

We developed additional novel fusion molecules incorporating an anti-EGFR antibody domain. EGFR was chosen as a target due to the high prevalence of EGFR expression among a variety of human solid tumors including human colon, lung, head and neck, ovarian, squamous cell carcinoma, bladder, and other tumors. In addition EGFR is expressed on the surface of triple negative breast cancers, for which anti-HER2 reagents are inactive. In clinical practice the use of anti-EGFR antibodies alone is minimally effective in all of the aforementioned tumors, while cetuximab, an anti-EGFR antibody, has been combined with either chemotherapy or radiation in a variety of clinical settings with modest incremental response. We linked the mutant endostatin-P125A domain to an anti-EGFR antibody in an effort to target EGFR+ tumors. The anti-EGFR IgG3 fusions with wild type endostatin (αEGFR-huEndo) or endostatin-P125A (αEGFR-huEndo-P125A) were constructed as shown in FIG. 1 substituting anti-EGFR sequences for anti-HER2 sequences. The anti-EGFR fusion proteins retained anti-EGFR specificity, (FIG. 12B), and correct folding of the endostatin domain as demonstrated by protein gel and western blotting (FIG. 12A). Anti-EGFR specificity was demonstrated by flow cytometry, and anti-endostatin antibodies recognized both wild type and mutant endostatin-P125A domains within the fusions by western blot, or by flow cytometry (FIGS. 12A, B).

Figure 13A:
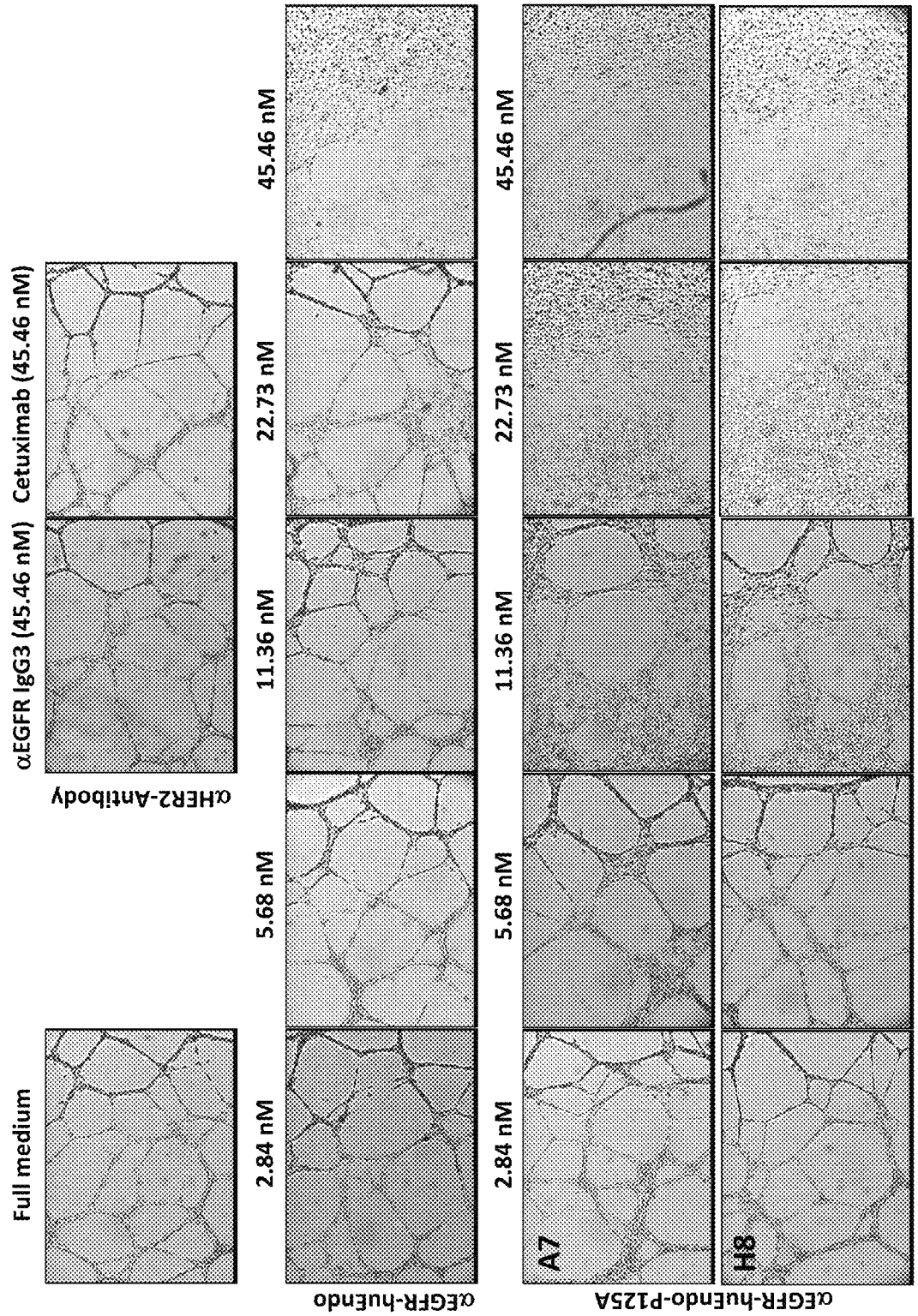
FIG. 13. Effects of antibody-human endostatin fusion proteins on HUVEC tube formation. (A and B) Effects of anti-EGFR IgG3-human endostatin (αEGFR-huEndo) fusion proteins on EC tube formation: HUVECs were resuspended in endothelial cell growth medium and treated as indicated before plating onto the Matrigel-coated plates. Following 16 hr of incubation, tube formation was observed through an inverted photomicroscope. (A) Tube formation with media alone and 45.46 nM αEGFR IgG3 were compared to those with 2.84-45.46 nM αEGFR-huEndo and αEGFR-huEndo-P125A (two preparation A7 and H8). (B) Quantitation of 'tube' formation: iTF₅₀ is represented as the 50% inhibition of tube formation on treated cells vs. on controls. Each completed 'circle' was counted as 'one' tubular structure. (C) Effects of anti-HER2 IgG3-human endostatin (αHER2-huEndo) fusion proteins on EC tube formation: (C) Tube formation with αHER2-huEndo and αHER2-huEndo-P125A were compared at the concentrations of 2.05-136.38 nM. Tube formation was quantified as described in FIG. 13B.
Figure 13B:
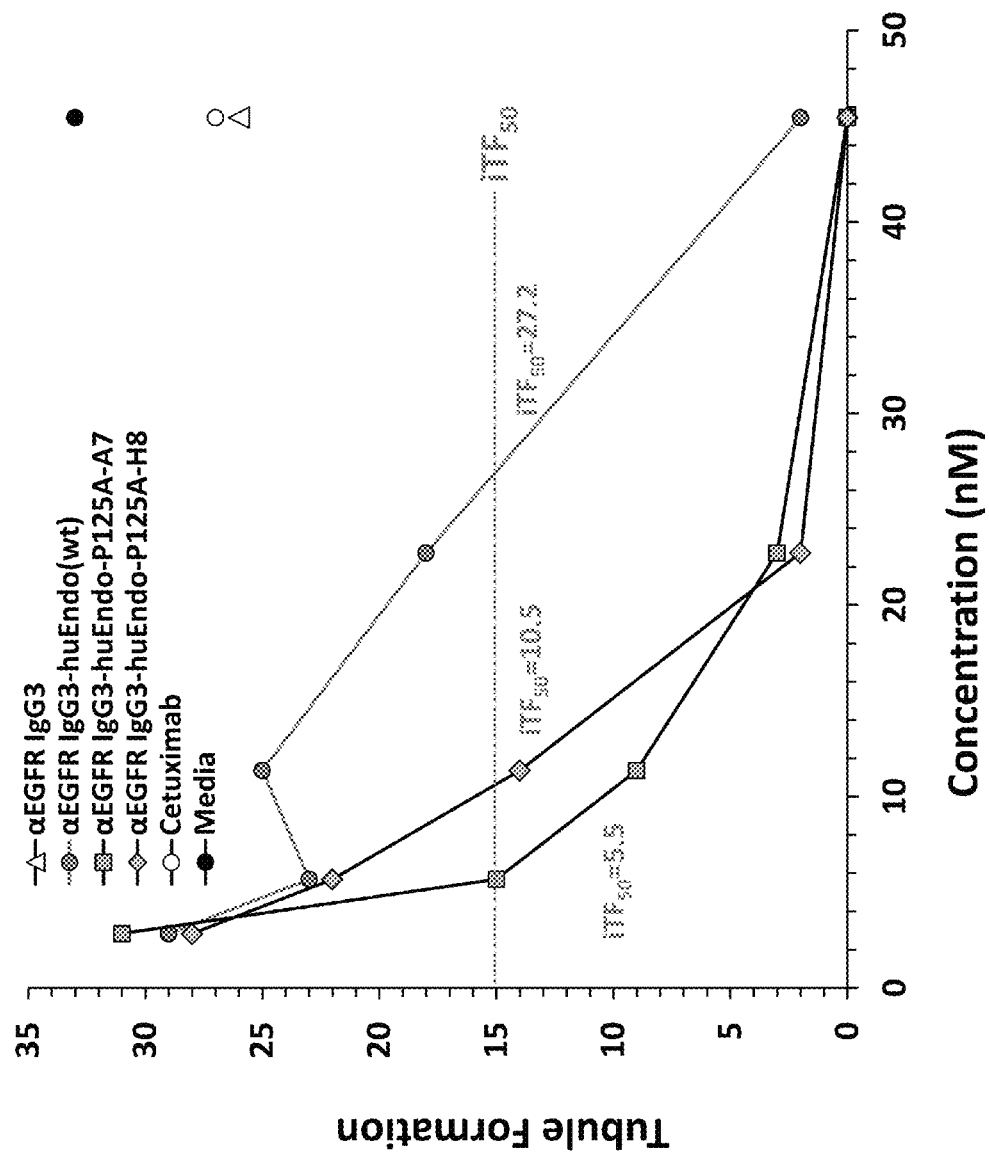
Figure 13C:
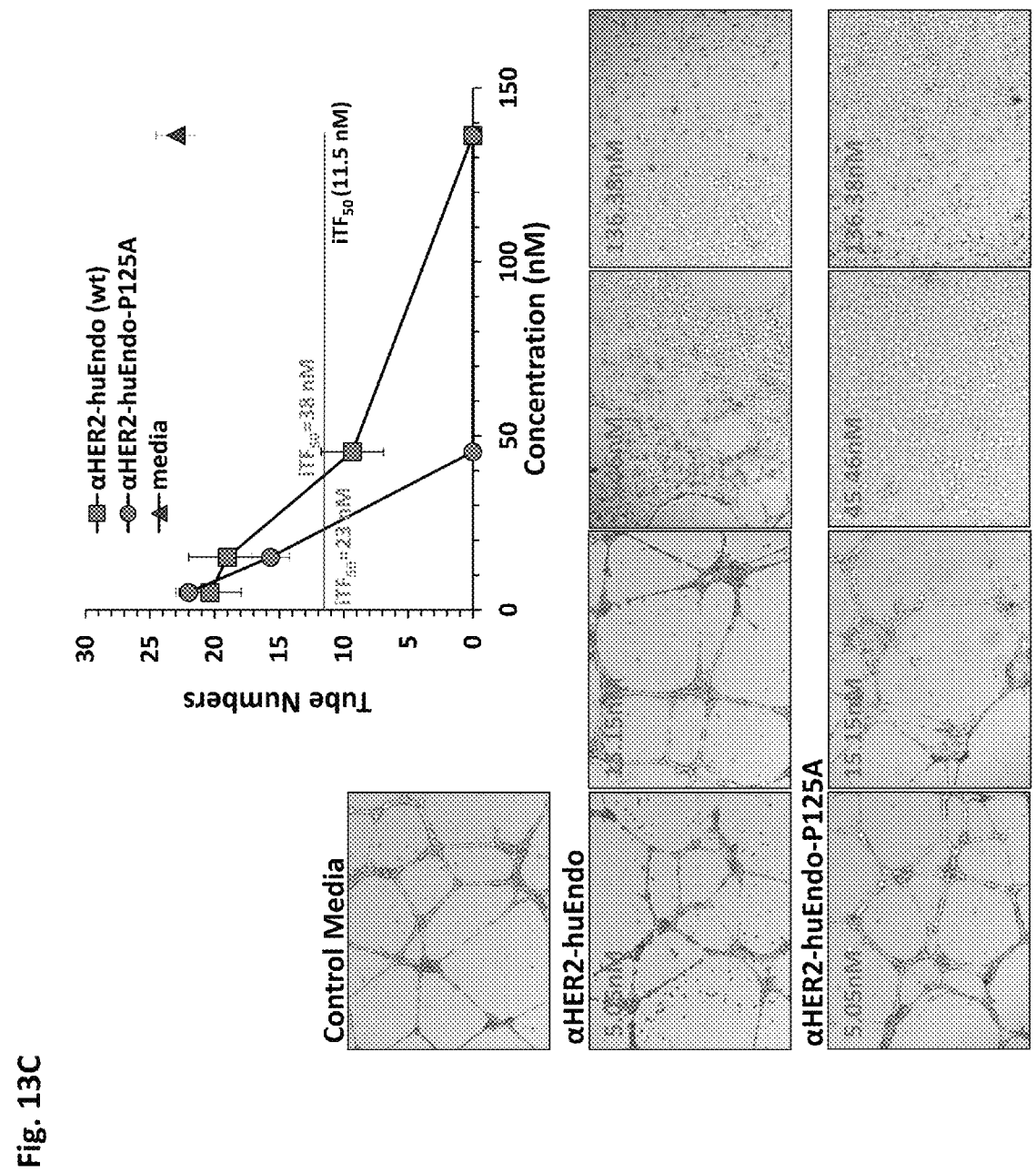

We next tested for effects on endothelial tube formation using HUVEC as shown in FIG. 13. Human endostatin-P125A (huEndo-P125A) had minimal effects on tubule formation. In contrast increasing doses of anti-EGFR IgG3-human endostatin (αEGFR-huEndo) fusion showed marked inhibition of tube formation, and near complete abrogation of tube formation at the highest concentrations used. Anti-EGFR IgG3-human endostatin-P125A (αEGFR-huEndo-P125A) fusion resulted in significant inhibition of tube formation, which was significantly more potent than that seen with wild type endostatin fusion (αEGFR-huEndo) at all concentrations tested (FIGS. 13A, B). No inhibition of tube formation was seen with cetuximab or using media controls. In addition, no inhibition of tube formation was seen with a control anti-EGFR IgG3 (αEGFR IgG3) antibody. This once again indicated a significantly greater antiangiogenic effect of the presently claimed αEGFR-huEndo-P125A fusion. This was quantitated using a quantitative assay for an inhibition of tube formation, in which we compared anti-EGFR IgG3-wild type endostatin (αEGFR-huEndo) fusion to anti-EGFR IgG3-human endostatin-P125A (αEGFR-huEndo-P125A) fusion. Wild type endostatin fusion showed 50% inhibition of tube formation at a concentration of 27.2 nM, while two different preparations of anti-EGFR IgG3-human endostatin-P125A fusion demonstrated 50% inhibition at concentrations of 10.5 and 5.5 nM, respectively (FIG. 13B). A comparison of anti-HER2 IgG3-huEndo using a wild type endostatin (αHER2-huEndo) fusion domain to anti-HER2 IgG3-huEndo-P125A using a mutant endostatin-P125A domain (αHER2-huEndo-P125A) shows enhanced antiangiogenic activity of the mutant endostatin-P125A fusion (FIG. 13C). The markedly increased anti-angiogenic activity of the αEGFR-huEndo-P125A fusion was unexpected.

A variety of investigators have reported on the formation of blood vessel like structures in vitro, so-called 'vasculogenic mimicry', using several human tumors including human breast cancer and uveal melanoma, as well as human ovarian cancer cultured using angiogenic media on matrigel. Human triple negative breast cancer (TNBC), as well as human melanoma and other solid tumors appear to demonstrate unusual plasticity in vitro and are able to form tube-like structures mimicking the vasculogenic tubular structures formed by endothelial cells in vitro. This phenomenon, known as 'vasculogenic mimicry', has been correlated with more aggressive behavior in vivo especially in the setting of uveal melanoma and HER2+ breast cancer. A variety of tumors have been demonstrated in vivo to form vessel-like channels which may serve as conduits for nutrients, as well as red blood cells, and may actually anastomose with blood vessels, which actually serve to support tumor growth. Hence, we tested if inhibition of vasculogenic mimicry is useful in targeting tumor growth in vivo.

Figure 14A:
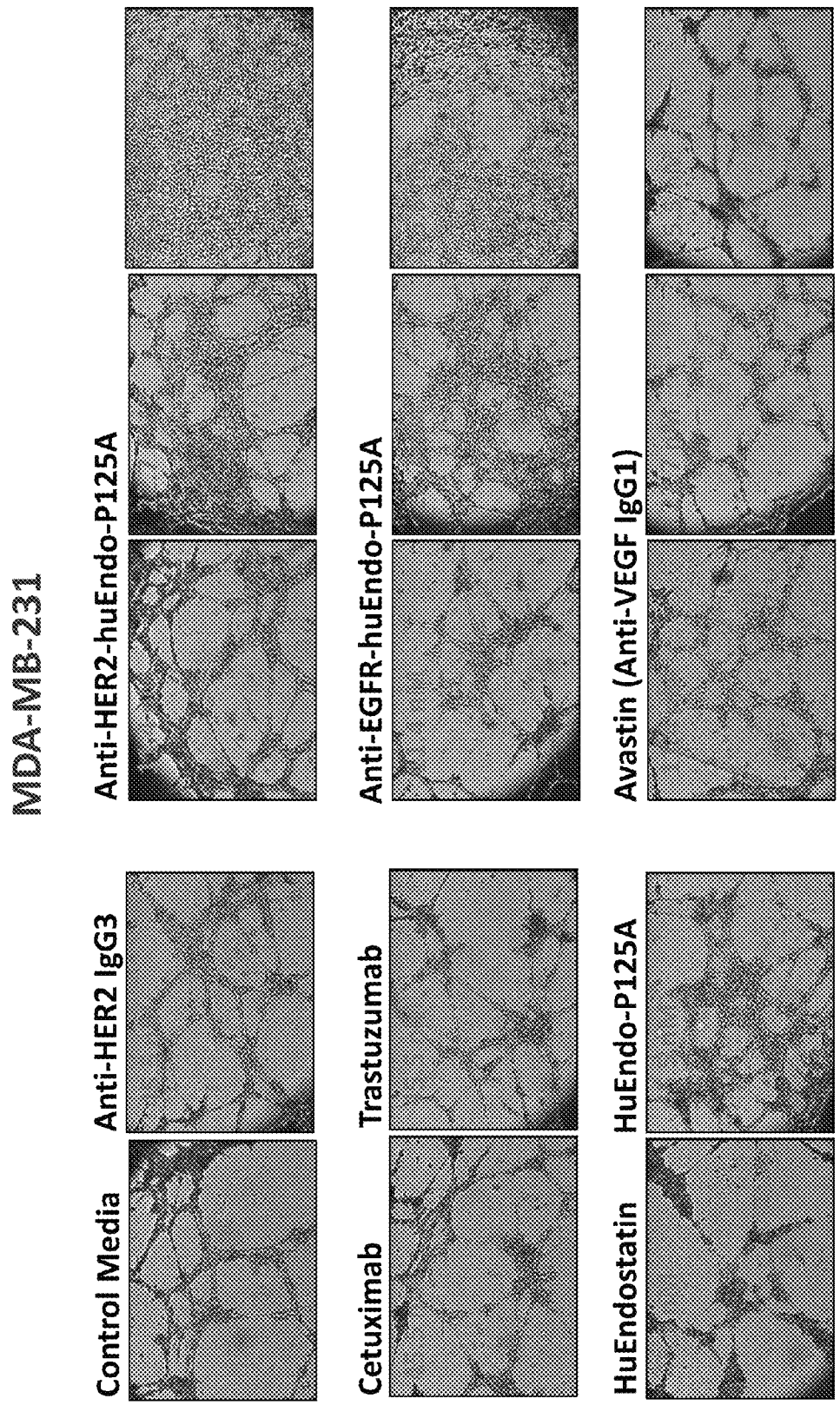
FIG. 14. Effects of antibody-human endostatin fusion proteins on vasculogenic mimicry. (A) Human triple negative breast cancer cells, MDA-MB-231, were resuspended in endothelial cell growth medium and treated as indicated before plating onto Matrigel-coated plates. Following 16 hr of incubation, tube formation was observed through an inverted photomicroscope. Vasculogenic mimicry with media alone, control antibodies (45.5 nM), human endostatin (huEndo, 45.5 or 454.6 nM), and human endostatin-P125A (huEndo-P125A, 45.5 or 454.6 nM), and αEGFR IgG3 (45.5 nM) were compared to those with αHER2-huEndo-P125A (11.4-45.5 nM) and αEGFR-huEndo-P125A (11.4-45.5 nM). (B and C) Tube formation by human ovarian cancer cells, SKOV3 (B) and PEO-1 (C). Experiments were performed as described above in FIG. 14A. (D) Tube formation by human uveal melanoma cells, MUM-2B, was tested as shown above in FIG. 14A.

We tested a triple negative breast cancer cell (TNBC) line, MDA-MB-231, for the ability to form vascular-like structures in vitro. As demonstrated in FIG. 14A, MDA-MB-231 cells form tube-like structures on endothelial cell growth media (EGM) in matrigel. Tube formation was not inhibited by human endostatin, human mutant endostatin-P125A, cetuximab, trastuzumab, or anti-HER2 IgG3 antibody. In contrast, when MDA-MB-231 cells were exposed to increasing concentrations of the presently claimed antibody-human endostatin-P125A fusions (αHER2-huEndo-P125A or αEGFR-huEndo-P125A), dose dependent inhibition of tube formation was observed. Tube formation was completely abrogated a concentration of 45.5 nM. In contrast, commercially available Avastin, an anti-VEGF IgG1 had no effects on tube formation (FIG. 14A). The unusually potent effect of antibody-endostatin-P125A fusions (αHER2-huEndo-P125A or αEGFR-huEndo-P125A) on vasculogenic mimicry was totally unexpected. Since endostatin and endostatin-P125A were not known to directly affect 'vasculogenic mimicry,' nor known to directly interact with tumor cells, the results obtained using the antibody-endostatin-P125A fusions in inhibiting 'vasculogenic mimicry' by tumor cells were completely unexpected.

Figure 14B:
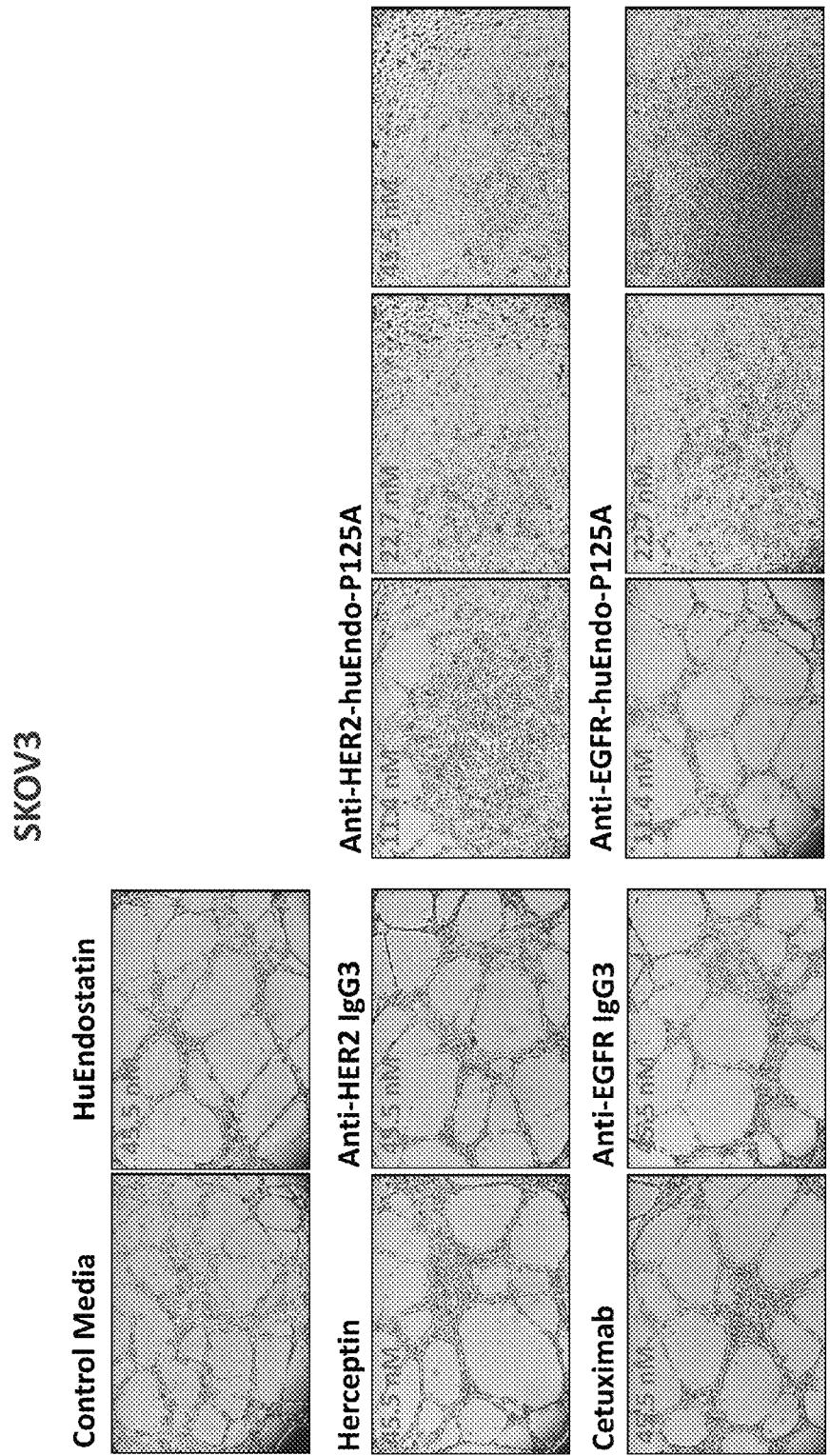
Figure 14C:
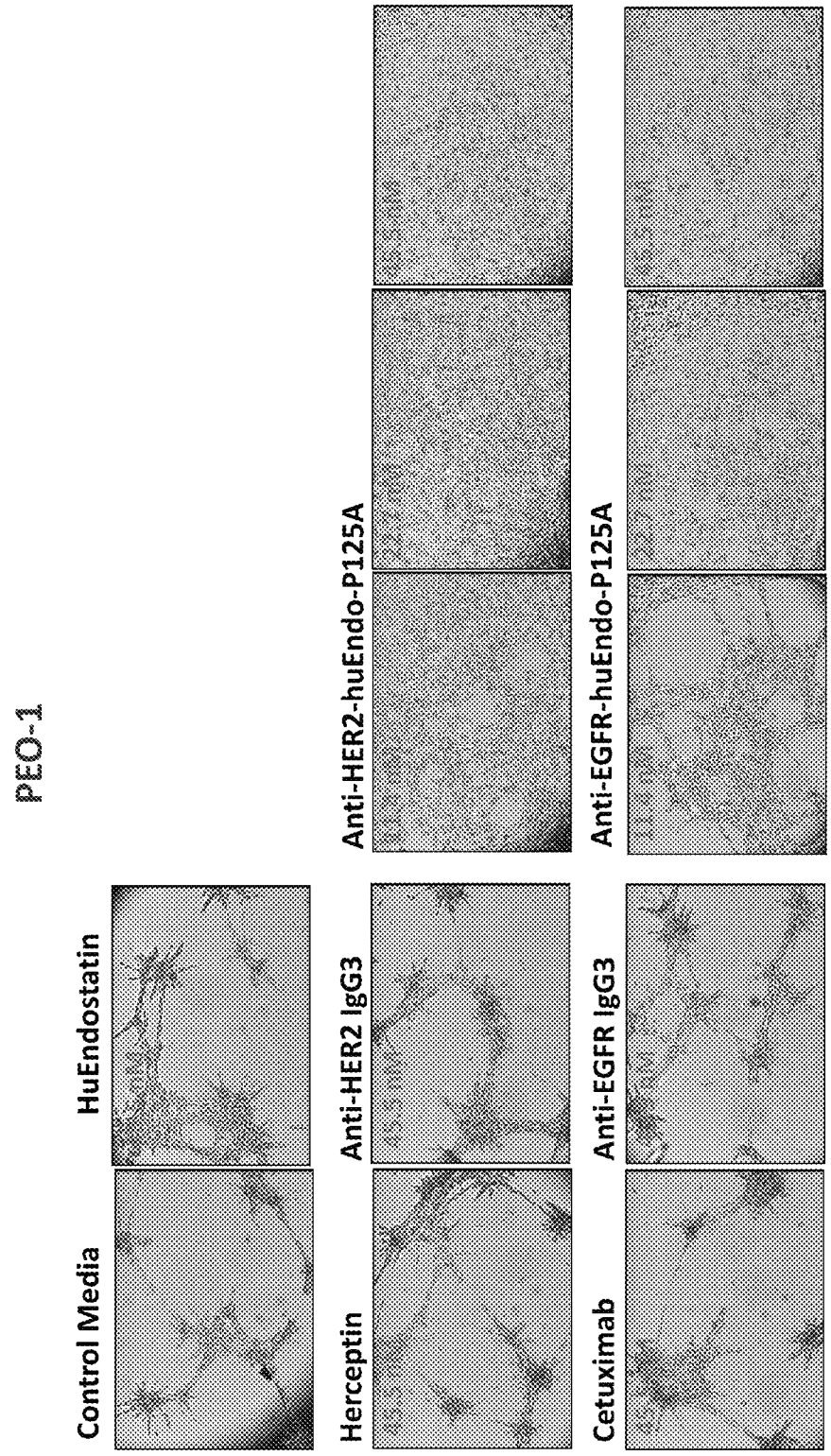

Similar experiments were performed with SKOV3 and with PEO-1, both HER2+ ovarian cancer cell lines (FIG. 14B). These cell lines also formed tubes in vitro, and exhibited similar vasculogenic mimicry. Tube formation by either SKOV3 or PEO-1 was completely inhibited using either anti-HER2 IgG3-human endostatin-P125A (αHER2-huEndo-P125A) fusion protein or anti-EGFR IgG3-human endostatin-P125A (αEGFR-huEndo-P125A) fusion in dose dependent fashion (FIGS. 14B, 14C). As before, direct effects of the antibody-endostatin-P125A fusions on vsaculogenic mimicry by ovarian cancer cells were completely unexpected. Since aggressiveness and progress in ovarian cancer has been correlated to ability to engage in vasculogenic mimicry, the observed effects on vasculogenic mimicry are likely to have clinical significance.

Figure 14D:
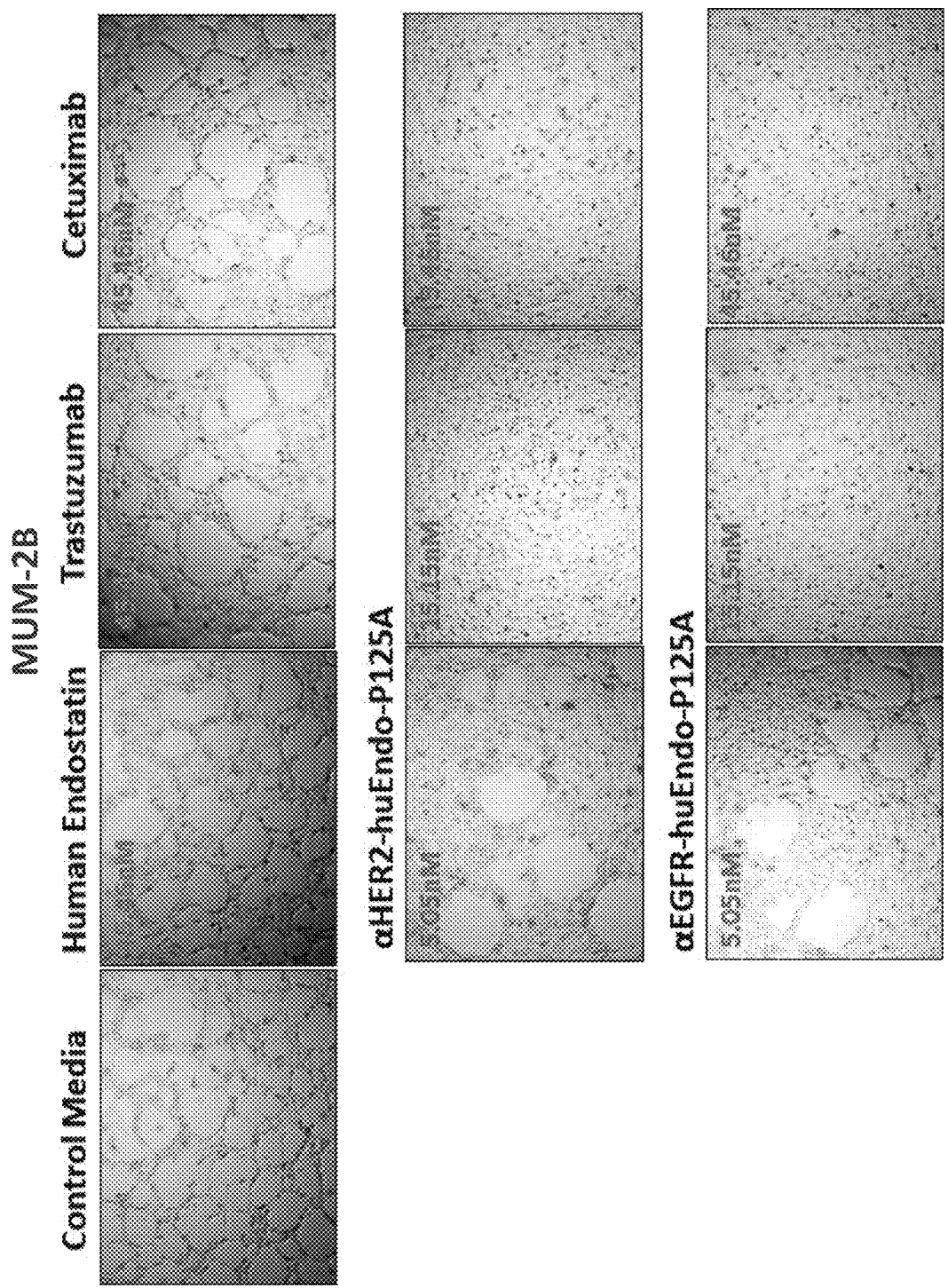

In addition to the aforementioned cell lines, we also tested the ability of the endostatin fusions to inhibit vasculogemic mimicry by human uveal melanoma cells. The uveal melanoma cell line MUM-2B formed tube-like structures in vitro. Both the anti-HER2 IgG3-huEndo-P125A (αHER2-huEndo-P125A) and anti-EGFR IgG3-huEndo-P125A (αEGFR-huEndo-P125A) fusions markedly reduced tube formation as compared to endostatin, cetuximab, or trastuzumab, respectively (FIG. 14D).

Figure 15:
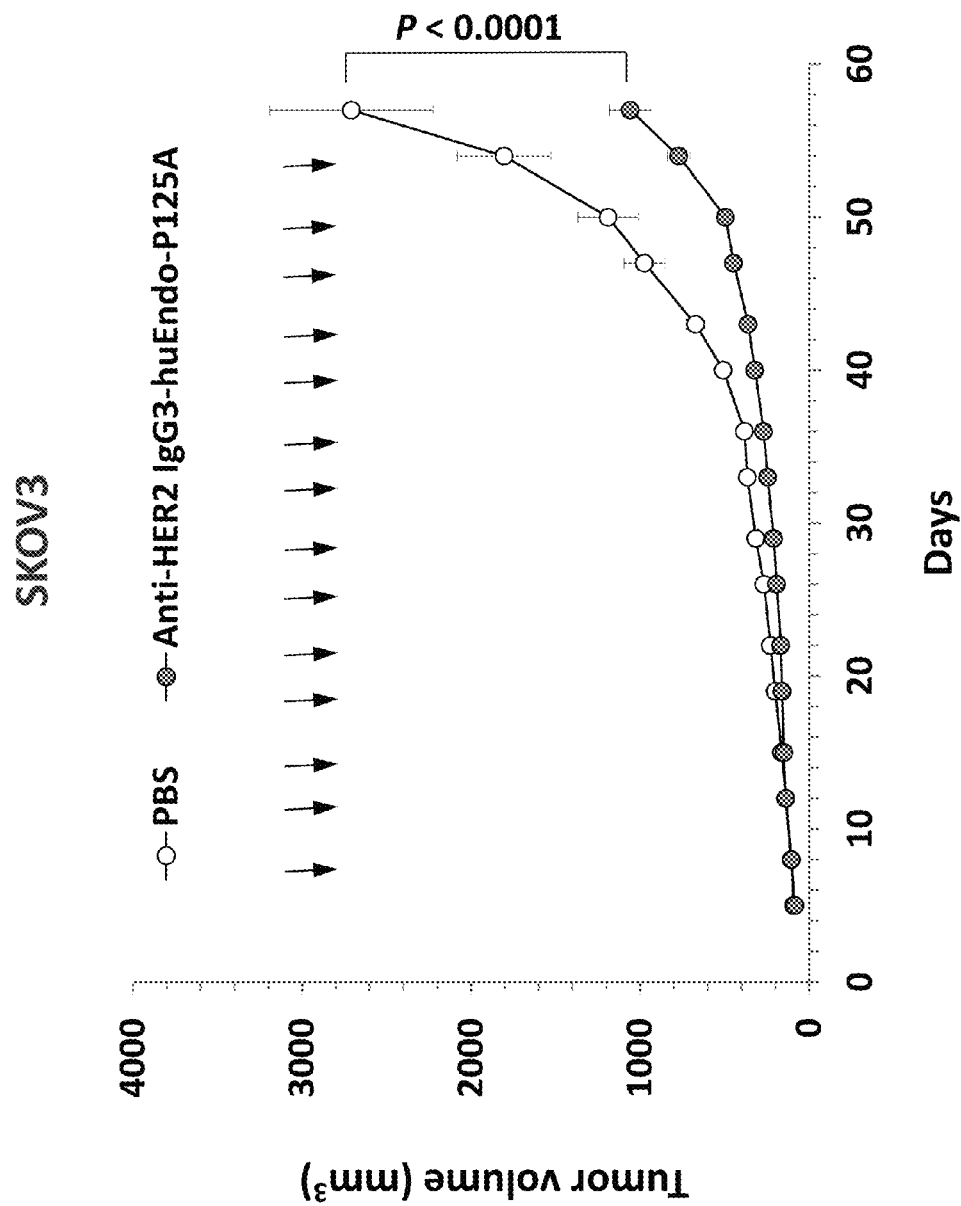
FIG. 15. Antitumor efficacy of αHER2 IgG3-huEndo-P125A fusion protein on human ovarian cancer xenografts, SKOV3. NSG mice (n=5-9) were implanted s.c. with SKOV3 (10⁶ cells), then i.v. injected with αHER2 IgG3-huEndo-P125A fusion protein (42 μg), or PBS twice a week (arrows) starting on day 8. Tumor growth was measured and the values represent mean±SEM of tumor volume (mm³) of 5-9 mice.

Finally, we investigated anti-tumor efficacy in human ovarian cancer SKOV3 xenografts (FIG. 15). SKOV3 is a HER2-amplified human ovarian cancer cell line which grows slowly as a xenograft in NSG mice. We assayed for anti-tumor activity of presently claimed αHER2-huEndo-P125A fusion protein against SKOV3 xenografts in NSG mice. In FIG. 15, αHER2-huEndo-P125A fusion proteins were injected twice a week (FIG. 15). αHER2-huEndo-P125A fusion protein significantly inhibited tumor growth relative to the non-treated group (PBS, p<0.0001). This demonstrated anti-tumor efficacy against HER2+ human ovarian tumors.

The data provided herein demonstrates that anti-HER2-huEndo-P125A and anti-EGFR-huEndo-P125A inhibited both normal endothelial angiogenesis and also of tumor cell vasculogenic mimicry. The dual inhibition of angiogenesis and vasculogenic mimicry is expected to result in improved anti tumor efficacy.

The data presented in the present application and herein shows that the difficulties experienced in treatment of cancer can surprisingly be overcome by the presently claimed compositions and chimeric fusion molecules. These results are unexpected.

Other Embodiments

It is to be understood that while the invention has been described in conjunction with the detailed description thereof, the foregoing description is intended to illustrate and not limit the scope of the invention. Other aspects, advantages, and modifications are within the scope of the following claims.

All references cited herein, are incorporated by reference in their entirety.

What is claimed is:

1. A method comprising the steps of:
   a) obtaining a biopsy sample of a tumor from a subject;
   b) contacting the biopsy sample with a chimeric fusion molecule comprising an anti-tumor antigen binding domain from an anti-HER2 antibody or anti-EGFR antibody and at least one human endostatin protein or fragment thereof, wherein the at least one human endostatin protein or fragment thereof comprises a proline to alanine amino acid substitution at position 125 of human endostatin, and
   (c) detecting vasculogenic mimicry in the biopsy sample.

2. The method of claim 1, comprising a further step of determining if the tumor cells exhibit vasculogenic mimicry between steps a) and b).

3. The method of claim 1, further comprising (d) administering the chimeric fusion molecule to the subject.

4. The method of claim 1, wherein the antigen binding domain specifically binds one or more tumor antigens.

5. The method of claim 1, wherein the human endostatin protein or fragment thereof comprises one or more NGR motifs (Asn-Gly-Arg) and/or RGD (Arg-Gly-Asp) motifs.

6. The method of claim 5, wherein the one or more NGR motifs (Asn-Gly-Arg) and RGD (Arg-Gly-Asp) motifs are located at the amino (NH$_2$—) terminal, and/or carboxy terminal (COOH—) and/or amino acid positions 93-133 of human endostatin protein or fragment thereof.

7. The method of claim 5, wherein the one or more NGR motifs (Asn-Gly-Arg) and RGD (Arg-Gly-Asp) motifs are located at amino acid positions 126-128 following the proline or alanine at position 125 of the human endostatin protein or fragment thereof.

8. The method of claim 3, wherein the chimeric fusion protein is administered to the subject in combination with and/or in separate treatments, with one or more of: cetuximab, sunitinib, sorafenib, celebrex, MTOR inhibitors, AKT inhibitors, P13K inhibitors, bevacizumab (Avastin), signal transduction inhibitors, tamoxifen, toremifen, raloxifene, droloxifene, iodoxyfene, megestrol acetate, anastrozole, letrazole, borazole, exemestane, flutamide, nilutamide, bicalutamide, cyproterone acetate, goserelin acetate, leuprolide, finasteride, herceptin, methotrexate, 5-fluorouracil, cytosine arabinoside, doxorubicin, daunomycin, epirubicin, idarubicin, mitomycin-C, dactinomycin, mithramycin, cisplatin, carboplatin, melphalan, chlorambucil, busulphan, cyclophosphamide, ifosfamide, nitrosoureas, thiotephan, vincristine, taxol, taxotere, etoposide, teniposide, amsacrine, irinotecan, topotecan, an epothilone; a tyrosine kinase inhibitor, Iressa or OSI-774; an angiogenesis inhibitor; an EGF inhibitor; a VEGF inhibitor; a CDK inhibitor; a Her1/2 inhibitor; or monoclonal antibodies directed against growth factor receptors.

9. The method of claim 3, wherein the chimeric fusion protein is administered to the subject in combination with and/or in separate treatments with one or more antibodies or compounds selected from the group consisting of cetuximab, sunitinib, sorafenib, celebrex, MTOR inhibitors, AKT inhibitors, P13K inhibitors, bevacizumab (Avastin), signal transduction inhibitors, anti-PDL1, anti-CTLA4, anti-EGFR antibodies, and anti-HER2 antibodies.

10. The method of claim 3, wherein the chimeric fusion protein is administered to the subject in combination with and/or in separate treatments with one or more anti-angiogenic factors selected from the group consisting of sunitinib, sorafenib, and angiostatin.

* * * * *

UNITED STATES PATENT AND TRADEMARK OFFICE
CERTIFICATE OF CORRECTION

PATENT NO. : 9,611,313 B2
APPLICATION NO. : 14/254333
DATED : April 4, 2017
INVENTOR(S) : Seung-Uon Shin et al.

Page 1 of 1

It is certified that error appears in the above-identified patent and that said Letters Patent is hereby corrected as shown below:

In the Specification

Column 1, Line 15, please insert:
--Statement of Government Interest
This invention was made with government support under grant number W81XWH-05-1-0351 awarded by the United States Army Medical Research Materiel Command. The government has certain rights in the invention.--

Signed and Sealed this
Fifteenth Day of September, 2020

Andrei Iancu
*Director of the United States Patent and Trademark Office*